United States Patent [19]

Snow et al.

[11] Patent Number: 5,760,191

[45] Date of Patent: *Jun. 2, 1998

[54] MACROCYCLIC COMPLEXING AGENTS AND TARGETING IMMUNOREAGENTS USEFUL IN THERAPEUTIC AND DIAGNOSTIC COMPOSITIONS AND METHODS

[75] Inventors: Robert A. Snow, West Chester; Daniel J. Delecki, Upper Merion; Chandra R. Shah, Frazer, all of Pa.

[73] Assignee: Nycomed Imaging AS, Norway

[ * ] Notice: The term of this patent shall not extend beyond the expiration date of Pat. No. 5,707,603.

[21] Appl. No.: 392,614

[22] Filed: Feb. 22, 1995

Related U.S. Application Data

[63] Continuation of Ser. No. 13,859, Feb. 5, 1993, abandoned.

[51] Int. Cl.[6] .................. C07F 5/00; C07F 13/00; C07D 225/00; C07D 262/22
[52] U.S. Cl. .................. 534/10; 534/14; 534/15; 534/16; 540/465; 540/469; 540/474
[58] Field of Search .................. 424/9.34, 9.341, 424/9.35, 9.351, 9.361, 9.362, 1.65; 540/465, 469, 472; 534/10, 14, 15, 16

[56] References Cited

U.S. PATENT DOCUMENTS

| | | | |
|---|---|---|---|
| 5,204,448 | 4/1993 | Subramanian | 530/391.5 |
| 5,271,927 | 12/1993 | Parker et al. | 424/9 |
| 5,559,214 | 9/1996 | Delecki et al. | 534/10 |
| 5,571,897 | 11/1996 | Takalo et al. | 534/15 |

FOREIGN PATENT DOCUMENTS 9208494  5/1992  WIPO ................ A61K 47/48

*Primary Examiner*—John Kight
*Assistant Examiner*—Lara C. Kelley
*Attorney, Agent, or Firm*—Fish & Richardson P.C.

[57] ABSTRACT

A metal chelate comprising a compound having the following formula and one or more metal ions which metal ions are a radionucleotide or a paramagnetic metal ion:

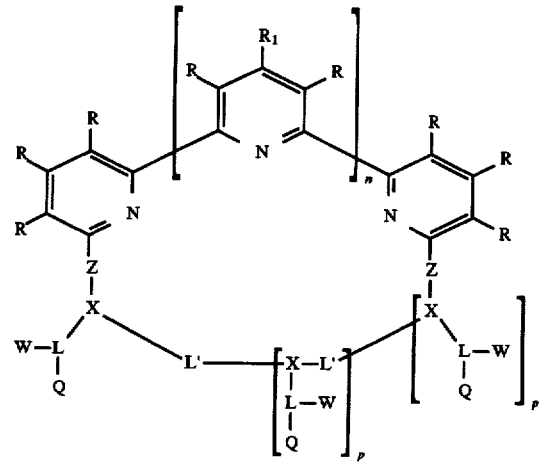

17 Claims, No Drawings

MACROCYCLIC COMPLEXING AGENTS AND TARGETING IMMUNOREAGENTS USEFUL IN THERAPEUTIC AND DIAGNOSTIC COMPOSITIONS AND METHODS

This application is a continuation of Ser. No. 08/013,859, filed Feb. 5, 1993, now abandoned.

FIELD OF THE INVENTION

The present invention relates to novel macrocyclic completing agents as well as to novel immunoreagents, preferably targeting radioactive immunoreagents, which comprise the novel complexing agents, and which find particular utility in therapeutic and diagnostic imaging compositions and methods.

BACKGROUND OF THE INVENTION

Prior to 1980, the targeting of tumor-bearing sites by radioimmunoglobulin had been demonstrated by a number of laboratories at different institutions (S.E. Order et al., "Use of Isotopic Immunoglobulin in Therapy," *Cancer Research* 40, 3001-7 (August 1980)). By 1980 it was demonstrated that tumors would concentrate radiolabeled-antibodies to tumor associated antigens and that such radiolabeled reagents (targeting radioactive immunoreagents) allowed both diagnostic imaging of tumors, e.g., by gamma camera imaging (radioimmunoscintigraphy) and positron tomography, and therapeutic treatment, i.e., reduction in tumor size.

Early targeting with radiolabeled immunoreagents was carried out with radioactive iodine. However, as noted by Scheinberg et al., "Tumor Imaging with Radioactive Metal Chelates Conjugated to Monoclonal Antibodies," *Science* 215, No. 19, 1511-13 (March 1982), iodine isotopes pose several problems, particularly with respect to scanning of tumor images. Of the three commonly available isotopic forms, only $^{123}$I has the appropriate emission characteristics for imaging and a short enough half-life to be safely used diagnostically. The gamma radiation of $^{125}$I is too weak for imaging. $^{131}$I has often been used but is undesirable because of its long half-life and high energy gamma and cytotoxic beta radiations. Moreover, rapid metabolism of radioiodinated antibodies allows incorporation of the iodine into the thyroid and active excretion of the iodine by the stomach and urinary tract. This dispersion of the radioactive iodine hinders imaging of specific tumors, since the tumors are hidden by background radiation.

In addition to tumor targeting with radioactive antibodies for diagnostic imaging and therapeutic treatment, similar targeting has been accomplished for diagnostic imaging of infarcts, specifically, myocardial infarcts, using antibodies to canine cardiac myosin [Khaw et al., "Myocardial Infarct Imaging of Antibodies to Canine Cardiac Myosin Indium-111-Diethylenetriamine Pentaacetic Acid," *Science* 209, 295-7 (July 1980)], and for imaging atherosclerosis by targeting atherosclerotic plaques. The same disadvantages in the use of radioactive iodine exist for diagnostic infarct imaging as for tumor imaging and therapeutic treatment.

It is known that $^{111}$In can be complexed with polyaminocarboxylic acids such as ethylene diaminetetraacetic acid (EDTA) and diethylenetriaminepentaacetic acid (DTPA). However, the covalent linkage of proteins (antibodies) to these complexing agents, accomplished by acylation with activated carbonyls, aromatic diazonium coupling, or bromoacetylation, is inefficient, even though the isocyanatobenzyl derivatives described by Brechbiel et al. ["Synthesis of 1-(p-Isothiocyanatobenzyl) Derivatives of DTPA and EDTA. Antibody Labeling and Tumor Imaging Studies," *Inorg. Chem.* 25, 2772-81 (1986)] were created to facilitate covalent attachment of proteins with the complexing agents.

Recently, research efforts have been directed to improved antibodies (Ab's), e.g., monoclonal, specific antibodies for specific targeting, as well as to antibodies that complex or bind directly with radionuclides, and to preferred radionuclides and combinations thereof with antibodies and complexing agents. Some attempts have been made towards improving complexing agents.

Nonetheless, EDTA and especially DTPA and derivatives thereof have remained the prevalent complexing agents to covalently bind antibody and coordinately complex metallic radionuclides. However, the inadequacies of DTPA have been noted, for example, by Parker et al. ["Implementation of Macrocycle Conjugated Antibodies for Tumor Targeting," *Pure and Appl. Chem.*, 61, No. 9, 1637-41 (1989): "Conventionally the metal radionuclide has been complexed by an acyclic chelate (e.g. EDTA or DTPA) which is covalently linked to the antibody. None of the chelates is adequate because the metal tends to dissociate in vivo. . . ."] and by Cox et al., ["Synthesis of a Kinetically Stable Yttrium-90 Labelled Macrocycle-Antibody Conjugate," *J. Chem. Soc., Chem. Commun.* 797-8 (1989): "Yttrium-90 is an attractive isotope for therapy . . . but its clinical use will be very limited because of bone marrow toxicity, resulting from acid-promoted release of $^{90}$Y from an antibody linked chelate such as diethylenetriamine-pentaacetic acid (DTPA)"].

Previous attempts to develop improved complexing agents have provided materials which have their own shortcomings. For example, Craig et al., "Towards Tumor Imaging with Indium-111 Labelled Macrocycle-Antibody Conjugates," *J. Chem. Soc. Chem. Commun.*, 794-6 (1989), describe macrocyclic hexacoordinating ligands but state that "The limiting feature of this approach is that $^{111}$In labelling of the macrocycle is required before antibody conjugation. Indium binding by (4) is insufficiently fast at 37° C. for efficient radiolabeling . . . . Other tribasic triazamacrocyclic ligands were screened therefore for their ability to bind indium rapidly under mild conditions (20° C., pH 5, <1 h), yet still form a kinetically stable complex in vivo . . . . However, only (6) proved effective when the ligand concentration was 10 µM, and under these conditions a 96% radiolabeling yield was determined (30 min, pH 5, 20° C.)."

Nevertheless, thirty minutes is still unsatisfactory. It would be highly desirable to have complexing agents superior to EDTA and DTPA which would coordinately bind preferred radionuclides such as In, Y, Sc, Ga, Ge, etc. within a few minutes, i.e., in less than about 5 minutes, immediately prior to administration of the reagent to the patient, especially when a short-lived radionuclide must necessarily be generated from a longer-lived radionuclide at the time of treatment of the patient.

It should be noted that complexes of yttrium, a preferred radionuclide for therapy, tend to be less stable than those of indium [(Mather et al., "Labelling Monoclonal Antibodies with Yttrium 90," *Eur. J. Nucl. Med.* 15, 307-312 (1989)] with respect to conventional complexes. Mather et al. teach that biodistribution studies in cancer patients using radiolabeled antibodies have suggested that the in vivo stability of yttrium-labeled antibodies is not as great as that of their $^{111}$In-labelled counterparts and that these findings are supported by other recent publications in the field.

When chelating agents are covalently bonded to proteins (such as Ab's), the proteins usually are capable of accepting far more than one molecule of the chelating agent because they contain a host of amine and sulfhydryl groups through which the chelating agents are bound. It is often very important to determine how many chelating sites are bound to each protein molecule. The most convenient way to accomplish this is by spectrophotometric means. However, many prior art chelating agents and metal chelates thereof have spectral absorptions that overlap with those of useful proteins, or have spectral absorbances with wavelengths and intensities that vary with changes in the microenvironment of the chelating agent and of the metal chelates thereof such as occurs when a chelating agent or chelate is attached to a protein. An analytical determination of the number of chelating or chelated sites per molecule of protein cannot be made unequivocally by spectrophotometry since the overlapping and shifting spectral absorptions mask each other. It would thus be highly desirable to obtain chelating agents for conjugation to proteins whose spectrophotometric absorptions, and whose metal chelate spectrophotometric absorptions, do not overlap with those of the proteins to which the chelating agents are chemically bonded and which are not susceptible to changes in absorbance wavelength and intensity with a change in microenvironment.

Another problem with some prior art compositions is that the chelator must be activated by a reducing agent before forming the radionuclide chelate. If the protein conjugates are to be formed prior to formation of the radionuclide chelate, then the reducing agent employed for activating the complexing agent can degrade the protein. For example, the preferred chelating agents currently used for complexing technetium (Tc) and rhenium (Re) complex to the metals via sulfur-containing groups which must be reduced with a reducing agent (dithiothreitol) to activate the chelator before forming the radionuclide chelate. If the protein conjugate containing disulfide bonds is formed prior to reduction, then the reducing agent can degrade the protein. It would be highly desirable to have chelating agents capable of forming conjugates with proteins before complexing with radionuclides.

In summary, the various commercially available radiolabeled antibodies and chelating agents employed for making immunoreactive conjugates by covalently bonding a chelating agent to the immunoreactive protein, as well as radionuclide complexes thereof for use in diagnostic imaging and targeted therapeutics, suffer from one or more of the following disadvantages: 1) destruction or excretion of the reagent due to rapid catabolism or metabolism; 2) inefficient covalent bonding of the radioactive component with protein in conjugate preparation; 3) slow complexation with metals; 4) unstable metal complexation, e.g., with respect to temperature, time or pH; 5) inability to form conjugates and remain stable in storage until metal complexation is desired; 6) inability to spectrophotometrically analyze the radionuclide complex reagent; and 7) inability to complex without activation steps that degrade protein.

In a recently filed patent application (see PCT/US91/08253; WO92/08494), co-workers have disclosed targeting radioactive immunoreagents which effectively solve most of the problems of the prior art discussed above. The targeting radioactive immunoreagents of that patent application comprise a metal radionuclide ion, a complexing agent which is a derivative of a pyridine, bipyridine, terpyridine, quaterpyridine, quinquepyridine, sexipyridine or phenanthroline, and an immunoreactive group covalently bonded through a protein reactive group to the complexing agent.

More particularly, the complexing agents of that application have the general structure A-I

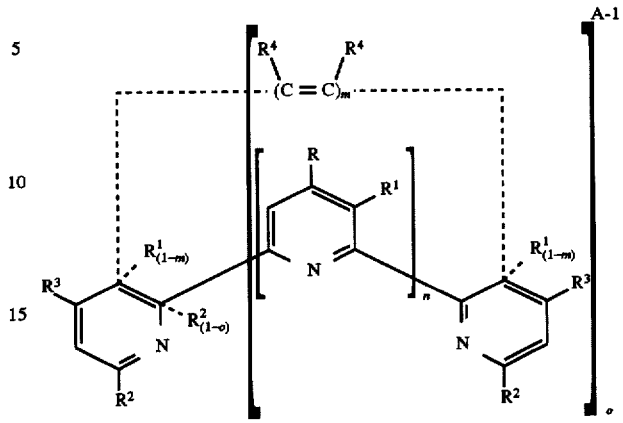

wherein
R represents hydrogen, alkyl, alkoxy, alkylthio, alkylamino, alkylformamido, aryl, aryloxy, heterocyclyl or a protein reactive group;

$R^1$ represents hydrogen, alkyl, alkoxy, alkylthio, alkylamino, alkylformamido, aryl, aryloxy, $R^2$ represents hydroxy, carboxy, hydroxyalkyl, thioalkyl, carbonyliminodiacetic acid, methyleneiminodiacetic acid, methylenethioethyleneiminodiacetic acid, carboxyalkythioalkyl, hydrazinylidenediacetic acid, or a salt of such acids, or two $R^2$ groups, taken together, represent the atoms necessary to complete a macrocyclic ring structure containing at least one heteroatom coordinating site and at least one, preferably two, alkylene groups forming part of the ring structure;

$R^3$ represents hydrogen, alkyl, alkoxy, alkylthio, alkylamino, alkylformamido, aryl, aryloxy, heterocyclyl or a protein reactive group;

$R^4$ represents hydrogen or a protein reactive group;
n is 0, 1, 2, 3 or 4;
o is 0 or 1;
m is 0 or 1;
provided that at least one of n and m is 0 and at least one of R, $R^1$, $R^3$ and $R^4$ is a protein reactive group.

While a significant advance over the prior art, the chelators of structure A-I, particularly the macrocyclic oligo-2, 6-pyridyl moieties therein, by virtue of the protein reactive group being attached either directly to a pyridine ring at a 3-, 4- or 5- position of the ring or, indirectly, to a group that is attached to a pyridine ring at a 3-, 4- or 5-position of said ring, may have substituent electron density donating or electron density withdrawing properties that affect electron distribution at the, pyridyl chelating site in a metal complex. Properties of the chelators and of the metal chelates thereof which may be affected by changes in electron distribution at such a pyridyl chelating site include rate of metal binding by the chelator, strength of chelate to metal binding, and spectroscopic properties such as ultraviolet and visible light wavelength and absorbance, as well as fluorescent and phosphorescent emission wavelengths and intensities. Similarly, in immunoconjugates comprising chelators of structure A-I, the attachment of an immunoreactive group by reaction of a reactive group on the immunoreactive moiety with the protein reactive group of structure A-I results in a change in the electron configuration in (i.e., a change in the chemical bonds of) the protein reactive group, such as occurs, for example, in a change from an isothiocyanate group to a thiourea group during reaction with an amine group on an immunoreactive group such as an antibody. This change in the nature of the substituent attached either directly to a pyridine ring at a 3-, 4- or 5- position of the ring or, indirectly, to a group that is attached to a pyridine ring at a 3-, 4- or 5-position of said ring, can change the electron distribution at the chelating site of the pyridine ring and can thus affect the metal binding and spectroscopic properties of the chelate. Thus, it would be desirable to provide chelators that retain the advantages of the oligo-2,6-pyridyl chelators of structure A-I, the pyridine groups of which are not subject to alterations in electron density caused by reaction of the protein reactive group.

In addition, for metal binding and spectroscopic properties of the macrocyclic chelating agents such as those described in structure A-I and of metal complexes thereof to be only minimally subject to changes in the microenvironment experienced by the chelating site, such as would occur when a protein reactive group reacts with a reactive site on a protein and which results in the protein occupying space that would otherwise be occupied by solvent molecules such as water, (i.e., in order to enhance the stability of the metal chelate) it is desirable that groups peripheral to the macrocyclic oligo-2,6-pyridine moiety have the ability to coordinate with or supply electron density to the metal ion and thus mask the effects of a change in microenvironment. Such coordination can be either through a primary coordination array of ligand electron density such as obtains when ligands are directly bonded to available metal ion (for example, at octahedral geometric sites of metal ion coordination), or through an outer, secondary array of coordination electron density which is further removed than the primary coordination array from, but still interacts with, the metal ion.

This invention provides oligo-2,6-pyridinyl-containing macrocyclic complexing agents having a protein reactive group attached to the complexing agent at a position other than directly to the 3-, 4-, or 5-position of a pyridine ring of the oligo-2,6-pyridyl-containing component or indirectly through a substituent to a 3-, 4-, or 5- position of a pyridine ring of the oligo-2,6-pyridyl-containing component.

This invention further provides such oligo-2,6-pyridinyl-containing macrocyclic complexing agents wherein the protein reactive group is attached to the complexing agent by a linking group comprising a group of 1, 2, or 3 carbon atoms attached to the macrocyclic ring, at least one carbon atom of which is attached to a heteroatom which can participate in the chelation of a metal ion chelated by the oligo-2,6-pyridinyl-containing macrocyclic portion of the chelating agent.

SUMMARY OF THE INVENTION

In accordance with the present invention, there are provided novel, oligo-2,6-pyridinyl-containing macrocyclic complexing agents each having a single protein reactive group attached to the complexing agent at a position other than directly to the 3-, 4-, or 5-position of a pyridine ring of the oligo-2,6-pyridyl-containing component or indirectly through a substituent to a 3-, 4-, or 5-position of a pyridine ring of the oligo-2,6-pyridyl-containing component by an extra-ring linking group comprising a group of 1, 2, or 3 carbon 25 atoms at least one of which is attached to a heteroatom which can participate in the chelation of a metal ion by the oligo-2,6-pyridinyl-containing macrocyclic portion of the chelating agent.

The novel complexing (or chelating) agents have the advantage that they do not require chemical modification directly at a 3-, 4-, or 5-position of a pyridine ring of the oligo-2,6-pyridine moiety or indirectly at a substituent at a 3-, 4-, or 5-position of a pyridine ring of the oligo-2,6-pyridine moiety to introduce a protein reactive group, which modification can otherwise cause a perturbation of the electron distibution at the pyridyl chelating site and which perturbation can change as a result of the protein reactive group reacting with a protein. Another advantage is that the chelating ability of the oligo-2,6-pyridine moiety of the macrocylic chelator can be modified by appropriate introduction of non-protein reactive group substituents at one or more of the 3-, 4-, or 5-positions of the pyridine rings of the oligo-2,6-pyridine moiety. The effect of this modification is not changed when a protein reactive group in another part of the molecule reacts with a protein.

More particularly, the present invention provides novel completing agents having the structure I:

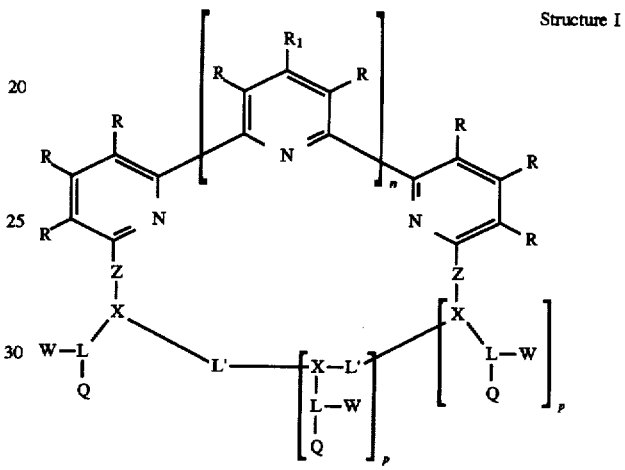

Structure I wherein each R and $R_1$ is independently selected from hydrogen, alkyl, alkoxy, hydroxyalkyl, alkoxyalkyl, hydroxyalkyloxy, alkoxyalkyloxy, alkylthio, alkylthioalkyl, alkylthioalkyloxy, hydroxyalkylthio, hydroxyalkylthioalkyl, hydroxyalkylthioalkyloxy, N,N-dialkylamino, N-(hydroxyalkyl)-N-alkylamino, N,N-bis(hydroxyalkyl)amino, N,N-dialkylaminoalkyl, N-(hydroxyalkyl)-N-alkylaminoalkyl, N,N-bis(hydroxyalkyl)aminoalkyl, alkylformamido, formamidoalkyl, aryl, alkylaryl, alkoxyaryl, hydroxyalkylaryl, alkoxyalkylaryl, hydroxyalkyloxyaryl, alkoxyalkyloxyaryl, alkylthioaryl, hydroxyalkylthioaryl, hydroxyalkylthioalkylaryl, hydroxyalkylthioalkyloxyaryl, aralkyl, aralkyloxy, alkoxyaralkyl, alkoxyaralkyloxy, aryloxy, alkylaryloxy, alkoxyaryloxy, and heterocyclyl;

each Q is independently selected from hydrogen, alkyl, hydroxyl, carboxyl, carboxyalkyl, hydroxyalkyl, alkylthioalkyl, sulfhydryl, thioalkyl, alkoxy, alkylthio, alkylamino, aminoalkyl, aminoalkylaminoalkyl, hydroxyalkylaminoalkyl, hydroxylaminoalkyl, hydroxamido, formamidoalkyl, alkylformamido, aryl, including substituted aryl, aryloxy, heterocyclyl, carbonyliminodiacetic acid, methyleneiminodiacetic acid, methylenethioethyleneiminodiacetic acid, carboxyalkylthioalkyl, a residue of ethylenediaminetetraacetic acid (EDTA), a residue of diethylenetriaminepentaacetic acid (DTPA), hydrazinylidenediacetic acid, and a salt of any of the foregoing acids;

each Z is independently selected from a heteroatom with a valence of two, a heteroatom with a valence of three, an alkylene group, an alkylene group bonded to a heteroatom having a valence of two, and an alkylene group bonded to a heteroatom having a valence of three;

each X is independently selected from nitrogen and a residue of an alkylene group;

each W is independently selected from hydrogen and a substituent that comprises a protein reactive group;

each L' is independently selected from a chemical bond and an intra-ring linking group;

each L is independently selected from a residue of an alkylene group and an extra-ring linking group;

n is 1, 2, 3 or 4; and each p is independently 0, 1, 2, 3 or 4;

provided that only one W is a protein reactive group;the L bonded to the W that is a protein reactive group contains 1, 2, or 3 carbon atoms and connects X to a heteroatom capable of participating in the chelation of a metal ion; and when X is a nitrogen and a heteroatom of Z is bonded to X, the heteroatom of Z is also nitrogen.

This invention also provides metal chelates, sometimes hereinafter referred to as complexes or as metal complexes, comprising complexing agents having the foregoing structure I bound to one or more metal ions.

In another embodiment, this invention provides a targeting immunoreagent comprising a metal ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

In another embodiment, this invention provides a targeting radioactive immunoreagent comprising a metal radionuclide ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

In another embodiment, this invention provides a targeting paramagnetic immunoreagent comprising a paramagnetic metal ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

In another embodiment, this invention provides a targeting fluorescent immunoreagent comprising a fluorescent metal ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

This invention also provides therapeutic and diagnostic compositions comprising the above-described targeting radioactive immunoreagents.

This invention also provides diagnostic compositions comprising the above-described targeting paramagnetic immunoreagents.

This invention also provides diagnostic compositions comprising the above-described targeting fluorescent immunoreagents.

This invention further provides a method for diagnostic imaging a site in a patient comprising a) administering to the patient an effective amount of the above-described radioactive immunoreagent capable of targeting the site in a pharmaceutically acceptable carrier therefor, and b) imagewise activating a radiation-sensitive element or device, such as, for example, a film or electronic sensor, with the radiation emitted from the targeted site.

This invention further provides a method for diagnostic imaging a site in a patient comprising a) administering to the patient an effective amount of the above-described paramagnetic immunoreagent capable of targeting the site in a pharmaceutically acceptable carrier therefor, and b) imagewise activating a nuclear magnetic resonance detection sensor element or device which is sensitive to a change in one or more nuclear magnetic relaxation properties of an isotope such as a proton at the site of the patient while exposed to a controlled magnetic field environment such as, for example, a magnetic field in a magnetic resonance imaging instrument, which change is induced by the paramagnetic metal ion of the immunoreagent.

This invention further provides a method for treating a disease site in a patient comprising administering to the patient or a specimen from the patient an effective amount of a therapeutic composition comprising the above-described radioactive immunoreagent capable of targeting the site and a pharmaceutically acceptable carrier therefor.

This invention further provides a method for diagnostic imaging a site in a specimen comprising a) administering to the specimen an effective amount of a fluorescent composition comprising the above-described fluorescent immunoreagent capable of targeting a site in the specimen, b) irradiating the specimen with light, and c) imagewise activating a fluorescence emission sensor element or device, such as, for example, a film or electronic sensor, with the fluorescent light emitted from the targeted site.

It is an advantageous feature of this invention that the targeting immunoreagents of this invention are not rapidly metabolized and do not deleteriously disperse.

It is another advantageous feature that the described complexes efficiently attach to proteins and other biological molecules.

Yet another advantageous feature of this invention is that the described complexes exhibit photometric emissions which have a low signal to noise ratio, good energy emission characteristics, and which are readily subject to spectrophotometric analysis.

Additionally, protein conjugates of the complexing agents can be formed and stored until metal complexation is desired, and complexation can be accomplished without activation steps that degrade protein.

Moreover, the complexing agents rapidly complex with metals, and the resulting chelates exhibit excellent stability with respect to time, temperature and pH.

Other advantageous features of this invention will become readily apparent upon reference to the following description of the preferred embodiments and specific examples.

DESCRIPTION OF PREFERRED EMBODIMENTS

The description which follows primarily concerns the novel complexing agents of the invention and their metal complexes, as well as usage of the targeting immunoreagents of the invention in therapeutic and diagnostic imaging compositions and methods. In addition, the complexing agents, metal chelates of complexing agents, and targeting radioactive immunoreagents of the invention are useful as diagnostic reagents, for example, as radioimmunoelectrophoresis reagents.

The complexing agents of this invention comprise a macrocyclic oligo-2,6-pyridine-containing ring which is a derivative of a terpyridine, or a quaterpyridine, or a quinquepyridine or a sexipyridine and which has the structural formula I recited in the Summary above.

Each R and $R_1$ in formula I independently is selected from:

hydrogen;

straight or branched chain or cyclic saturated alkyl, preferably containing from 1 to about 20 carbon atoms, such as methyl, ethyl, propyl, isopropyl, butyl, s-butyl, t-butyl, 2-ethylhexyl, decyl, hexadecyl, octadecyl, cyclohexyl, cyclopropyl, etc.;

alkoxy, the alkyl portion of which contains from 1 to about 20 carbon atoms as described above for alkyl;

hydroxyalkyl, the alkylene portion of which is a straight or branched chain or cyclic alkylene group, preferably containing from 1 to about 20 carbon atoms, such as methylene, ethylene, propylene, isopropylene, butylene, s-butylene, t-butylene, 2-ethylhexylene, decylene, hexadecylene, octadecylene, cyclohexylene, cyclohexanedimethylene, cyclopropylene, etc.;

alkoxyalkyl, the alkyl portion of which contains from 1 to about 20 carbon atoms as described above for alkyl, and the alkylene portion of which is a straight or branched chain or cyclic alkylene group which contains from 1 to about 20 carbon atoms as described above for alkylene;

hydroxyalkyloxy, the alkylene portion of which is a straight or branched chain or cyclic alkylene group which contains from 2 to about 20 carbon atoms as described above for alkylene, and the oxygen atoms of which are separated by at least two carbon atoms;

alkoxyalkyloxy, the alkyl portion of which contains from 1 to about 20 carbon atoms as described above for alkyl, and the alkylene portion of which contains from 2 to about 20 carbon atoms as described above for alkylene, and the oxygen atoms of which are separated by at least two carbon atoms;

alkylthio, the alkyl portion of which contains from 1 to about 20 carbon atoms as described above for alkyl;

alkylthioalkyl, the alkyl portion of which contains from 1 to about 20 carbon atoms as described above for alkyl, and the alkylene portion of which is a residue of an alkyl group which contains from 1 to about carbon atoms as described above for alkylene;

alkylthioalkyloxy, the alkyl portion of which contains from 1 to about 20 carbon atoms as described abovr for alkyl, and the alkylene portion of which contains from 2 to about 20 carbon atoms as described above for alkylene, and the oxygen and sulfur atoms of which are separated by at least two carbon atoms;

hydroxyalkylthio, the alkylene portion of which contains from 2 to about 20 carbon atoms as described above for alkylene, and the oxygen and sulfur atoms of which are separated by at least two carbon atoms;

hydroxyalkylthioalkyl, the alkylene of the hydroxyalkyl portion of which contains from 2 to about 20 carbon atoms as described above for alkylene, the sulfur and oxygen atoms of which are separated by at least two carbon atoms, and the alkylene of the thioalkyl portion of which independently contains from 1 to about 20 carbon atoms as described above for alkylene;

hydroxyalkylthioalkyloxy, the alkylene portions of which independently contain from 2 to about 20 carbon atoms as described above for alkylene and the sulfur and oxygen atoms of which are separated by at least two carbon atoms;

N,N-dialkylamino, each alkyl portion of which independently contains from 1 to about 20 carbon atoms as described above for alkyl;

N-hydroxyalkyl-N-alkylamino, the alkylene of the N-hydroxyalkyl portion of which contains from 2 to about carbon atoms as described above for alkylene, the oxygen and nitrogen atoms of which are separated by at least two carbon atoms, and the N-alkyl portion of which contains from 1 to about 20 carbon atoms as described for alkyl above;

N,N-bis(hydroxyalkyl)amino, the alkylene of each N-hydroxyalkyl portion of which contains from 2 to about 20 carbon atoms as described above for alkylene and the oxygen and nitrogen atoms of which are separated by at least two carbon atoms;

N,N-dialkylaminoalkyl, the alkyl of each of the N,N-alkyl portions of which independently contains from 1 to about 20 carbon atoms as described above for alkyl, and the alkylene portion of which contains from 2 to about 20 carbon atoms as described above for alkylene;

N-hydroxyalkyl-N-alkylaminoalkyl, the alkylene of the N-hydroxyalkyl portion of which contains from 2 to about 20 carbon atoms as described above for alkylene, the oxygen and nitrogen atoms of which are separated by at least two carbon atoms, the alkyl of the N-alkylamino portion of which contains from 1 to about 20 carbon atoms as described above for alkyl, and the alkylene portion of which contains from 2 to about 20 carbon atoms as described above for alkylene;

N,N-bis(hydroxyalkyl)aminoalkyl, the alkylene of each hydroxyalkyl portion of which independently contains from 2 to about 20 carbon atoms as described above for alkylene, the oxygen and nitrogen atoms of which are separated by at least two carbon atoms, and the alkylene of the aminoalkyl portion of which contains from 1 to about 20 carbon atoms as described above for alkylene;

alkylformamido, the alkyl portion of which contains from 1 to about 20 carbon atoms as described above for alkyl;

formamidoalkyl, the alkylene portion of which contains from 1 to about 20 carbon atoms as described above for alkylene;

unsubstituted and substituted aryl, the aryl portion of which preferably contains from about 6 to 24 carbon atoms, such as phenyl, naphthyl, and phenanthryl, and the substituents of which are preferably selected from alkyl, nitro, halogen (such as chloro, bromo, and iodo), N,N-dialkylamino as defined above, alkoxy as defined above, alkylthio as defined above, carboxy, sulfonato, hydroxyalkyl as defined above, and alkoxyalkyl as defined above, for example, nitrophenyl, chlorophenyl, phenoxyphenyl, N-hexadecyl-N-methylaminophenyl, N-methyl-N-octadecylaminophenyl, 4-methoxy-3-iodophenyl, 4-methoxy-3-(N,N-dimethyl)phenyl, methylthiophenyl, carboxyphenyl, and sulfonatophenyl;

alkylaryl, the alkyl portion of which contains from 1 to about 20 carbon atoms as described above for alkyl, and the arylene portion of which is the residue of an aryl group containing from 6 to 24 carbon atoms as described above, such as alkylphenyl, for example, tolyl, xylyl and ethylphenyl;

alkoxylaryl, the alkyl portion of which contains from 1 to about 20 carbon atoms as described above for alkyl and the arylene portion of which contains from 6 to about 24 carbon atoms as described above for arylene, for example, methoxyphenyl, methylenedioxyphenyl, methoxyethoxyphenyl, and dimethoxyphenyl;

hydroxyalkylaryl, the alkylene of which contains from 1 to about 20 carbon atoms as described above for alkylene and the arylene portion of which contains from 6 to about 24 carbon atoms as described for arylene above, for example, hydroxyethylphenyl, bis(hydroxymethyl)phenyl, dihydroxycyclohexylphenyl, and hydroxymethylanthracenyl;

alkoxyalkylaryl, the alkyl portion of which contains from 1 to about 20 carbon atoms as described above for alkyl, the alkylene portion of which contains from 1 to about 20 carbon atoms as described above for alkylene, and the arylene portion of which contains from 6 to about 24 carbon atoms as described above for arylene, for example, 4-(2-methoxyethoxy)ethylphenyl, t-butoxypropylnaphthyl, and 2-(2,3-dimethoxypropoxy)-ethylphenyl;

hydroxyalkyloxyaryl, the alkylene portion of which contains from 2 to about 20 carbon atoms as described above for alkylene, the oxygen atoms of which are separated by at least two carbon atoms, and the arylene portion of which contains from 6 to about 24 carbon atoms as described above for arylene, for example, 4-(2-hydroxyethoxy)phenyl, and 5-hydroxypropoxy-3,4-methylenedioxyphenyl;

alkoxyalkyloxyaryl, the alkyl portion of which contains from 1 to about 20 carbon atoms as described above for alkyl, the alkylene portion of which contains from 2 to about 20 carbon atoms as described above for alkylene, the oxygen atoms of which are separated by at least two carbon atoms, and the arylene portion of which contains from 6 to about 24 carbon atoms as described above for arylene, for example, 4-(2-ethoxyethoxy)phenyl, methoxyethoxynaphthyl, methoxyethoxyphenyl, 3,4-bis(2-methoxyethoxy)phenyl, and 4-poly(ethylene oxidyl)phenyl, the poly(ethylene oxidyl) portion of which contains from 2 to 100 recurring units of ethylene oxide;

alkylthioaryl, the alkyl portion of which contains from 1 to about 20 carbon atoms as described above for alkyl, and the arylene portion of which contains from 6 to about 24 carbon atoms as described above for arylene, for example, methylthiophenyl, and 4-(2-ethylthio)phenyl;

hydroxyalkylthioaryl, the alkylene portion of which contains from 2 to about 20 carbon atoms as described above for alkylene, the oxygen and sulfur atoms of which are separated by at least two carbon atoms, and the arylene portion of which contains from 6 to about 24 carbon atoms as described above for arylene, for example, 2-hydroxyethylthiophenyl, 2,3-dihydroxypropylthiophenyl, and 4-(2,3-dihydroxypropyl)thio-3-methoxyphenyl;

hydroxyalkylthioalkylaryl, the hydroxyalkylthio portion of which contains an alkylene group having from 2 to about 20 carbon atoms as described above for alkylene, the oxygen and sulfur atoms of which are separated by at least two carbon atoms, the alkylene of the thioalkylaryl portion of which contains from 1 to about 20 carbon atoms as described above for alkylene, and the arylene portion of which contains from 6 to about 24 carbon atoms as described above for arylene, for example, (2-hydroxyethyl)thiomethylphenyl, 2-(2,3-dihydroxypropyl)thioethylphenyl, and 4-[(2,3-dihydroxypropyl)thiomethyl]phenyl;

hydroxyalkylthioalkyloxyaryl, each alkylene portion of which independently contains from 2 to about 20 carbon atoms as described above for alkylene, the oxygen and sulfur atoms of which are separated by at least two carbon atoms, and the arylene portion of which contains from 6 to about 24 carbon atoms as described above for arylene, for example, 4-[2-(2-hydroxyethyl)thioethoxy]phenyl, and 4,5-bis[2-(2-hydroxyethyl)thioethoxy]naphthyl;

aralkyl, the alkylene portion of which contains from 1 to about 20 carbon atoms as described above for alkylene and the aryl portion of which contains from about 6 to 24 carbon atoms as described above for aryl, for example, benzyl, trimethylbenzyl; and 9-(10-methyl)anthracenyl;

aralkyloxy, the alkylene portion of which contains from 1 to about 20 carbon atoms as described above for alkylene, and the aryl portion of which contains from about 6 to 24 carbon atoms as described above for aryl, for example, benzyloxy, methylenedioxybenzyloxy, 2-(methylenedioxyphenyl)ethoxy and phenylethoxy;

alkoxyaralkyl, the alkylene portion of which contains from 1 to about 20 carbon atoms as described for alkylene above, the alkyl portion of which contains from 1 to about 20 carbon atoms as described above for alkyl, and the arylene portion of which contains from about 6 to 24 carbon atoms as described above for arylene, for example, 3-(2,3-dimethoxypropoxy)benzyl, methoxybenzyl, and 4-poly(ethylene oxidyl)benzyl, the poly(ethylene oxidyl) portion of which contains from 2 to 100 recurring units of ethylene oxide;

alkoxyaralkyloxy, the alkyl portion of which contains from 1 to about 20 carbon atoms as described above for alkyl, the alkylene portion of which contains from 1 to about 20 carbon atoms as described above for alkylene, and the arylene portion of which contains from about 6 to 24 carbon atoms as described above for arylene, for example, 3-(2,3-dimethoxypropoxy)benzyloxy, methoxybenzyloxy, and 4-poly(ethylene oxidyl)benzyloxy, the poly(ethylene oxidyl) portion of which contains from 2 to 100 recurring units of ethylene oxide;

aryloxy, the aryl portion of which contains from 6 to about 24 carbon atoms as described above for aryl, such as phenoxy, nitrophenoxy, bromophenoxy, carboxyphenoxy, and sulfonatophenoxy;

alkylaryloxy, the alkyl portion of which contains from 1 to about 20 carbon atoms as described above for alkyl, and the arylene portion of which contains from about 6 to 24 carbon atoms as described above for arylene, for example, methylphenoxy, cyclohexylphenoxy, and butylphenoxy;

alkoxyaryloxy, the alkyl portion of which contains from 1 to about 20 carbon atoms as described above for alkyl, and the arylene portion of which contains from about 6 to 24 carbon atoms as described above for arylene, for example, methoxyphenoxy and 4-poly(ethylene oxidyl)phenoxy, the poly(ethylene oxidyl) portion of which contains from 2 to 100 recurring units of ethylene oxide; and substituted or unsubstituted heterocyclyl, containing from 5 to about 36 total nuclear carbon and heteroatoms and preferably comprising one ore more rings comprised of 5 or 6 nuclear carbon and heteroatoms such as N, S, P or O, for example, pyridyl, methylpyridyl, N-morpholino, dimethylaminopyridyl, methoxypropylpyridyl, oxazolyl, imidazolyl, pyrazolyl, quinolyl, thiazinyl, furanyl, pyranyl, and dimethylphosphazinyl.

In presently especially preferred embodiments, R is hydrogen and $R_1$ is a phenyl or a 4-alkoxyphenyl group.

Each Q in the above formula is independently selected from hydrogen, alkyl, alkoxy, hydroxyalkyl, alkylthioalkyl, alkylthio, alkylamino, hydroxyalkylaminoalkyl, formamidoalkyl, alkylformamido, aryl, including substituted aryl, aryloxy, and heterocyclyl, each of the foregoing preferably being as defined above for R and $R_1$; hydroxamido; hydroxylaminoalkyl, the alkyl portion of which contains from 1 to about 20 carbon atoms as described above for alkyl; aminoalkylaminoalkyl, the alkylene of the aminoalkylamino portion of which contains from 2 to about 20 carbon atoms as described above for alkylene and the other alkylene portion of which contains from 1 to about 20 carbon atoms as described above for alkylene; aminoalkyl, the alkylene portion of which contains from 1 to about 20 carbon atoms as described above for alkylene; thioalkyl, the alkylene portion of which contains from 1 to about 20 carbon atoms as described above for alkylene; sulfhydryl; hydroxyl; carboxyl; carboxyalkyl, the alkylene portion of which contains from 1 to about 20 carbon atoms as described above for alkylene; carboxyalkylthioalkyl, the alkylene portions of which contains from 1 to about 20 carbon atoms as described above for alkylene; carbonyliminodiacetic acid; methyleneiminodiacetic acid; methylenethioethyleneiminodiacetic acid; hydrazinylidenediacetic acid; a residue of ethylenediaminetetraacetic acid (EDTA); a residue of diethylenetriaminepentaacetic acid (DTPA); and a salt of any of the foregoing acids.

Each Z in Structure I is independently selected from a heteroatom with a valence of two, such as oxygen and sulfur; a heteroatom with a valence of three, such as nitrogen, an alkylene group containing 1 to 20 carbon atoms, for example, methylene, ethylene, propylene, isopropylene, isobutylene, etc.; an alkylene group containing 1 to 20 carbon atoms as described above bonded to a heteroatom having a valence of two, such as oxygen and sulfur; and an alkylene group containing 1 to 20 carbon atoms as described above bonded to a heteroatom having a valence of three such as nitrogen.

Each X in Structure I is independently selected from nitrogen and a residue of an alkylene group containing 1 to 20 carbon atoms, for example, methylene, ethylene, propylene, isopropylene, isobutylene, etc.

Each W in Structure I is independently selected from hydrogen and a substituent that comprises a protein reactive group;

each L' is independently selected from a chemical bond and an intra-ring linking group;

each L is independently selected from a residue of an alkylene group containing 1 to 20 carbon atoms as described above and an extra-ring linking group;

n is 1, 2, 3 or 4; and each p is independently 0, 1, 2, 3 and 4;

provided that only one W is a protein reactive group; the L bonded to the W that is a protein reactive group contains 1, 2, or 3 carbon atoms and connects X to a heteroatom capable of participating in the chelation of a metal ion; and when X is a nitrogen and a heteroatom of Z is bonded to X, the heteroatom of Z is also nitrogen.

The term "residue" is used herein in the context of a chemical entity comprising, for example, a ligand, or an alkyl group, or a chelating group, or a radioactive agent, or a linking group, or a protein reactive group, or an immunoreactive group, or an immunoreactive material, or an immunoreactive protein, or an antibody, or an antibody fragment, or a cross-linking agent such as a heterobifunctional cross-linking agent and is defined as that portion of a chemical entity which exclusively remains when one or more chemical bonds of which the chemical entity is otherwise comprised when considered as an independent chemical entity, is altered, modified, or replaced to comprise one or more covalent bonds to one or more other chemical entities. For example, in one aspect, a linking group between an immunoreactive group and a chelating agent comprises the residue of a protein reactive group of the chelating agent and the residue of the reactive group on the immunoreactive group with which the protein reactive group reacted. In this regard, when a protein reactive group such as an isothiocyanato group (i.e., an —N=C=S) on a chelating agent reacts with a reactive group such as an amine group (i.e., an $H_2N$—) on an immunoreactive group to form a thioureylene group [i.e., an —NH—C(=S)—HN—] linking the chelating agent with the immunoreactive group, the thioureylene group is a linking group comprising the residue of the protein reactive group and the residue of the amine group.

L' in Structure I refers to a chemical bond or a divalent "intra-ring linking group", one valence of which is attached to an X and the other valence of which is attached to either another X or to a Z. As such, when either valence of L' is attached to an alkylene group, L' can be a chemical bond, an alkylene group of 1 to 10 carbon atoms as described above for an alkylene group of R and $R_1$, or a part of an arylene group of 6 to 20 carbon atoms such as, for example, phenylene and others as described above for an arylene group of R and $R_1$ above. In addition, the alkylene group can be interrupted with one or more heteroatoms selected from oxygen, sulfur, and selenium, such as, for example, oxygen in ethyleneoxyethylene, sulfur in ethylenethioethylene, ethylenethio, thioethylene, ethylenethioethylenethio and ethylenedithioethylene, and selenium as ethyleneselenoethylene, or with heteroatom-containing groups such as carbonyl, sulfonyl and sulfinyl. The alkylene group can also be interrupted with a substituted or unsubstituted heterocyclic group, preferably containing rings comprised of 5 or 6 nuclear carbon and heteroatoms such as N, S, Se, P or O, for example, pyridyl, methylpyridyl, (N-carboxymethyl)morpholino, dimethylaminopyridyl, methoxypropylpyridyl, oxazolyl, imidazolyl, pyrazolyl, quinolyl, thiazinyl, furanyl, pyranyl, and methylphosphazinyl.

When both valences of L' are attached to heteroatoms, L' can be a chemical bond which links two nitrogen atoms, an alkylene group of 2 to 10 carbon atoms as described for an alkylene group of R and $R_1$ above, or a part of an arylene group of 6 to 20 carbon atoms such as, for example, phenylene and others as described for an arylene group of R and $R_1$ above. In addition, the alkylene group can be interrupted with one or more heteroatoms selected from oxygen, sulfur, and selenium, such as, for example, oxygen in ethyleneoxyethylene, sulfur in ethylenethioethylene, ethylenethio, thioethylene, ethylenethioethylenethio and ethylenedithioethylene, and selenium in ethyleneselenoethylene, or with heteroatom-containing groups such as carbonyl, sulfonyl and sulfinyl. The alkylene group can also be interrupted with a substituted or unsubstituted heterocylylic group, preferably containing rings comprised of 5 or 6 nuclear carbon and heteroatoms such as N, S, Se, P or O, for example, pyridyl, methylpyridyl, (N-carboxymethyl)morpholino, dimethylaminopyridyl, methoxypropylpyridyl, oxazolyl, imidazolyl, pyrazolyl, quinolyl, thiazinyl, furanyl, pyranyl, and methylphosphazinyl.

L in Structure I refers to a residue of an alkylene group or to a trivalent "extra-ring linking group", one valence of which is attached to an X, one valence of which is attached to a W, and the third valence of which is attached to a Q. When W is a protein reactive group, X is connected by L to a heteroatom such as oxygen, nitrogen, or sulfur, the oxygen of which is in an ether, ester, carbonyl, sulfoxyl, sulfonyl, phosphonyl, sulfonate, phosphate, or carboxyate group, the nitrogen of which is in an amide, amine, hydroxylamine, hydrazine, urea, thiourea, nitrile or imine group, and the sulfur of which is in a sulfhydryl, thioether, thiocarbonyl or disulfide group, which heteroatom is capable of participating in the chelation of a metal ion, and wherein L is a group that contains 1, 2, or 3 carbon atoms such as, for example, the residue of an alkylene group containing from 1 to 3 linearly bonded carbon atoms, i.e., methylene, ethylene, and propylene, and such as, for example, the residue of groups such as carbonylmethyl, ethyloxy, propyloxy, ethylamido, ethylthio, ethylamino, and propylthio. In addition, when L is ethylene or propylene, from 2 to about 100 of such ethylene groups, propylene groups, or combinations of ethylene and propylene groups can be tandemly linked by heteroatoms, each linking heteroatom being independently selected from oxygen, sulfur, and selenium, such as, for example, oxygen in ethyleneoxyethylene, propyleneoxypropylene, ethyleneoxypropylene, poly(ethyleneoxy)ethylene wherein the polymer contains from 2 to about 100 ethylene units, poly(propyleneoxy)propylene wherein the polymer contains from 2 to about 100 propylene units, poly(ethyleneoxy-co-propyleneoxy)ethylene, poly(ethyleneoxy-co-propyleneoxy)propylene, poly(propyleneoxy-co-ethyleneoxy)ethylene, and poly(propyleneoxy-co-ethyleneoxy)propylene wherein each polymer contains from 2 to about 100 ethylene and propylene units, sulfur in ethylenethioethylene, ethylenethiopropylene, propylenethioethylene, ethylenethioethylenethioethylene, and ethylenedithioethylene, and selenium in ethyleneselenoethylene and propyleneselenopropylene, or combinations such as ethyleneoxyethylenethioethylene, propyleneoxyethyleneselenoethylene, and the like.

Furthermore, from 2 to about 100 of such ethylene groups, propylene groups, or combinations of ethylene and propylene groups can be tandemly linked by combinations of heteroatom linking groups as described above and heteroatom-containing linking groups such as carbonyl, sulfonyl and sulfinyl, oxycarbonyl, and carbonyloxy. In addition, from 2 to about 100 of such ethylene groups, propylene groups, or combinations of ethylene and propylene groups can be tandemly linked by combinations of heteroatom linking groups as described above, heteroatom-containing linking groups as described above, and substituted or unsubstituted heterocyclic linking groups, which heterocyclic linking groups preferably contain rings comprised of 5 or 6 nuclear carbon and heteroatoms such as N, S, Se, P or O, for example, pyridylene, methylpyridylene, morpholinoene, dimethylaminopyridylene, methoxypropylpyridylene, oxazolylene, imidazolylene, pyrazolylene, quinolylene, thiazinylene, furanylene, pyranylene, and methylphosphazinylene.

The trivalent extra-ring linking group of L can be selected from a nitrogen atom; a nitrogen atom covalently linked to a methylene, ethylene or propylene group or combinations of ethylene and propylene groups as described for residues of the alkylene group of L above; an amino acid linkage, i.e., a

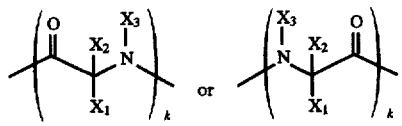

group wherein k=1 and $X_1$ and $X_2$ comprise the components of a naturally occurring amino acid or the optical enantiomer thereof such as alanine, glycine, serine, lysine, tyrosine, phenylalanine, glutamic acid, aspartic acid, and the like and $X_3$ is as described below, or $X_1$, $X_2$, $X_3$ independently are H, alkyl containing from 1 to 10, preferably 1 to 6, carbon atoms such as methyl, ethyl and propyl, and methylene, ethylene or propylene groups or combinations of ethylene or propylene groups as described for residue of the alkylene group of L above; or a peptide linkage, i.e., a

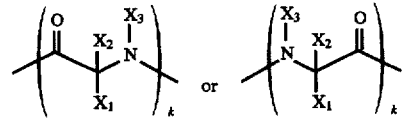

group wherein k>1 and each X independently is represented by a group as described for $X_1$, $X_2$, $X_3$ above. Especially preferred extra-ring linking groups include the residues of ethylene and propylene groups as described above.

As used herein, "protein reactive group" refers to a group W in Structure I which can react with a reactive functional group typically found on or introduced into a protein, especially an immunoreactive protein, to form a linking group between the complexing agent and the protein. However, it is specifically contemplated that a protein reactive group can be used to conjugate a complexing agent of this invention to a non-protein biomolecule as well as to a non-biological molecule such as a synthetic chemical substance (for example, a drug) that is of interest, for example, for the purposes of detection of such a molecule in a mixture which may contain such a synthetic chemical substance and which substance contains a group that is reactive with the protein reactive group. Thus, the protein reactive groups useful in the practice of this invention include those groups which can react with any molecule, preferably a biological molecule (such as a protein, a carbohydrate, a nucleic acid, and a lipid) containing a reactive group to form a linking group between the complexing agent and the molecule. Preferably the molecule is a protein, and preferred reactive groups on such protein molecule include amine groups and sulfhydryl groups. Especially preferred biological molecules contain an immunoreactive group as described hereinbelow.

The protein reactive groups useful in the practice of this invention also include those groups which can react with any biological molecule that is chemically modified, for example, by oxidation, by reduction, or by covalent bond formation such as by amide bond formation with another chemical species such as, for example, an amine, an amino acid, a substituted amine, or a substituted amino acid, to introduce a reactive group into the biological molecule, to form a linking group between the complexing agent and the chemically modified biological molecule.

The protein reactive groups useful in the practice of this invention also include those groups which comprise a portion of a specific receptor-ligand interactive group. For example, in the complexing agent of structure I, W can comprise an oligonucleotide group as a receptor portion of a receptor-ligand interactive group. The complementary oligonucleotide attached to a biological molecule is then a ligand portion of the receptor-ligand interactive group. Said ligand will bind to the receptor to form a linking group between the complexing agent and the biological molecule.

Preferred protein reactive groups can be selected from, but are not limited to, groups that will react directly with an amine group such as a lysine epsilon amine group or a terminal amine group in a peptide or with a sulfhydryl group such as a cysteine sulfhydryl group commonly found on a protein or other biological molecule. Examples of such protein reactive groups include active halogen-containing groups such as chloromethylphenyl groups, chloromethylcarbonyl groups, and iodomethylcarbonyl groups; activated 2-leaving-group-substituted ethylsulfonyl and ethylcarbonyl groups such as 2-chloroethylsulfonyl groups and 2-chloroethylcarbonyl groups; vinylsulfonyl groups; vinylcarbonyl groups; oxiranyl groups; isocyanato groups; isothiocyanato groups; aldehydo groups; aziridyl groups; succinimidoxycarbonyl groups; activated acyl groups such as carboxylic acid halide groups; anhydride groups; thioester groups; carbonates such as nitrophenylcarbonates; sulfonic acid esters; phosphoramidates; cyanuric monochlorides and cyanuric dichlorides; and other groups known to be useful in conventional photographic gelatin hardening agents.

The above listed protein reactive groups can react with a protein or other biological molecule which is chemically modified to contain reactive amine groups and sulfhydryl groups. Amine groups can be introduced by well known techniques such as, for example, nitration of a phenyl group followed by reduction, by conversion of a primary amide to an amine with nitrous acid, by conversion of a hydroxyl group of an alcohol into a sulfonic acid ester followed by displacement with an azide group and subsequent reduction to an amine, and the like. Sulfhydryl groups can be introduced by well known techniques such as, for example, by conversion of a hydroxyl group of an alcohol into a sulfonic acid ester followed by displacement with sodium sulfide, by dehydrative amide bond formation between an amine group of a protein and a carboxylic acid group of an acetylated cysteine using a carbodiimide reagent followed by treatment with hydroxylamine, and the like.

In addition, when a protein or other biological molecule can be chemically modified such as by partial oxidation to introduce an aldehyde group or a carboxylic acid group, a preferred "protein reactive group" can be selected from amino, aminoalkyl, aminoaryl, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms as described for R and $R_1$ above, and the aryl portions of the protein reactive group can contain from about 6 to about 24 carbon atoms as described for R and $R_1$ above.

An additional preferred protein reactive group can comprise a residue of a crosslinking agent. A useful crosslinking agent can react with a functional group such as, for example, an amine or sulfhydryl or carboxylic acid group or aldehyde group found in W of Structure I above and with a functional group such as, for example, an amine or sulfhydryl or carboxylic acid group or aldehyde group found in a protein or a biological molecule or in a chemically modified protein or biological molecule such as described above. The residues of certain useful crosslinking agents, such as, for example, difunctional gelatin hardeners, bisepoxides and bisisocyanates become a part of, i.e., a linking group in, a protein-complexing agent conjugate or a biological molecule-complexing agent conjugate which is formed as a result of the crosslinking reaction of such a crosslinking protein reactive group with a complexing agent and also with a protein or also with a biological molecule, respectively.

Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated herein by reference in its entirety, and the dication ethers of U.S. Pat. No. 4,877,724, the disclosure of which is hereby incorporated herein by reference in its entirety. With these crosslinking agents, one of the reactants must have a carboxyl group and the other an amine or sulfhydryl group. The crosslinking agent first reacts selectively with the carboxyl group, preferably a carboxyl group on a protein, then is split out during reaction of the "activated" carboxyl group with an amine, preferably an amine group of W in Structure I, to form an amide linkage between the protein or biological molecule and a complexing agent of this invention, thus covalently bonding the two moieties. An advantage of this approach is that crosslinking of like molecules, e.g., complexing agents with complexing agents, can be avoided, whereas the reaction of difunctional crosslinking agents is nonselective so that unwanted crosslinked molecules can be obtained.

Additional preferred protein reactive groups include semicarbazido; thiocarbazido; thiosemicarbazido; isocyanato and isothiocyanato; vinyl sulfonylalkyloxy, the alkylene group of which preferably contains from 2 to 10 carbon atoms and is as described for R and $R_1$ above; vinyl sulfonylalkylpoly(oxyalkyl)oxy, the alkylene group of the sulfonylalkyl portion of which preferably contains from 2 to 10 carbon atoms and is as described for R and $R_1$ above, the alkylene group of the polyoxyalkyl portion preferably contains from 2 to 10 carbon atoms and is as described for R and $R_1$ above, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; amidatoalkyloxy, the alkylene group of which preferably contains from 1 to 10 carbon atoms and is as described for R and $R_1$ above; hydrazidoalkyloxy, the alkylene group of which preferably contains from 1 to 10 carbon atoms and is as described for R and Ri above; azidocarbonylalkyloxy, the alkylene group of which preferably contains from 1 to 10 carbon atoms and is as described for R and $R_1$ above; aryloxycarbonyloxyalkyloxy, the alkylene group of which preferably contains from 2 to 10 carbon atoms and is as described for R and $R_1$ above, and the aryl group of which is as described for R and $R_1$ above; aryloxycarbonyl(polyoxyalkyl)oxy, the aryl group of which is as described for R and $R_1$ above, and the alkylene group of the polyoxyalkyl portion preferably contains from 2 to 10 carbon atoms and is as described for R and $R_1$ above, such poly(oxyalkyl)

portion preferably comprising a poly(oxyethylene) group or a poly(oxyethylene)-co-poly(oxypropylene) copolymer group, and the polymer contains from 2 to about 100 monomeric oxyalkylene units; triazines such as 4,6-dichloro-2-triazinylamino, 4,6-dichloro-2-triazinyloxy, 4,6-dichlorotriazinyl-2-oxy(polyalkyloxy), 4-alkoxy-6-chloro-2-triazinyloxy, and 4-alkoxy-6-chloro-2-triazinyl (polyoxyalkyl)oxy, the alkyl groups of the alkoxy portions preferably each containing from 2 to 10 carbon atoms and being as described for R and $R_1$ above, and the alkylene groups of the polyoxyalkyl portions preferably each containing from 2 to 10 carbon atoms and being as described for R and $R_1$ above, such a poly(oxyalkyl) portion preferably comprising a poly(oxyethylene) group or a poly (oxyethylene)-co-poly(oxypropylene) copolymer group, in which the polymer contains from 2 to about 100 monomeric oxyalkylene units; formylalkyl, the alkyl group of which preferably contains from 1 to 10 carbon atoms and is as described for R and $R_1$ above; aminoalkyl, the alkyl group of which preferably contains from 1 to 10 carbon atoms and is as described for R and $R_1$ above; active esters, for example, succinimidoxycarbonyl; active anhydrides and mixed anhydrides; active carbonates such as arylcarbonatoaryl, alkylcarbonatoaryl, arylcarbonatoalkyl, and alkylcarbonatoalkyl, the alkyl groups of which preferably contain from 2 to 10 carbon atoms and are as described for R and $R_1$ above, and the aryl groups of which are preferably comprised of a six membered ring containing electron withdrawing substituents such as, for example, nitro and halogen, and optionally containing water solubilizing groups such as a sulfonate salt; sulfhydryl; sulfhydrylalkyl, the alkyl group of which preferably contains from 1 to 10 carbon atoms and is as described for R and $R_1$ above; thioalkylcarbonylaminoalkyloxy, the alkylene group of the thioalkylcarbonyl portion preferably containing from 1 to 10 carbon atoms and being as described for R and $R_1$ above, and the alkylene group of the aminoalkyloxy portion preferably containing from 2 to 10 carbon atoms and being as described for R and $R_1$ above; maleimidoalkylcarbonylaminoalkyloxy, the alkylene group of the maleimidoalkylcarbonyl portion preferably containing from 1 to 10 carbon atoms and being as described for R and $R_1$ above, and the alkylene group of the aminoalkyloxy portion preferably containing from 2 to 10 carbon atoms and being as described for R and $R_1$ above; azido; iodoalkylcarbonylamino, the alkylene group of which contains from 1 to 10 carbon atoms and is as described for R and $R_1$ above; amidatoalkylamino, the alkylene group of which contains from 1 to 10 carbon atoms and is as described for R and $R_1$ above; and amidatoarylalkylamino, the alkylene group of which contains from 1 to 10 carbon atoms and is as described for R and $R_1$ above, and the aryl group of which is as described for R and $R_1$ above.

Especially preferred protein reactive groups include sulfhydryl, amino, isothiocyanato and arylcarbonatoalkyl.

Preferred classes of complexing agents according to the invention include macrocyclic terpyridines having structure II:

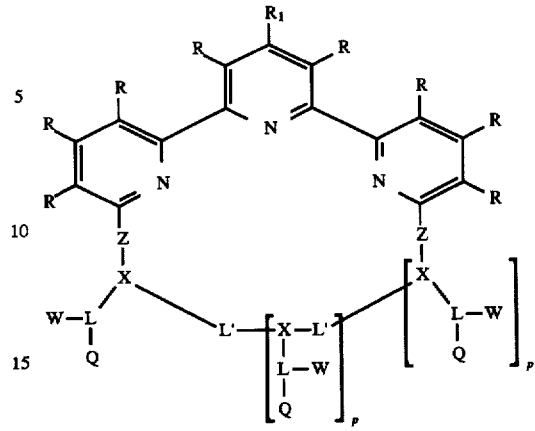

Structure II wherein R, $R_1$, Z, L, L', Q, W and p are as described above for Structure I.

An especially preferred class of complexing agents according to the invention includes macrocyclic terpyridines having structure III:

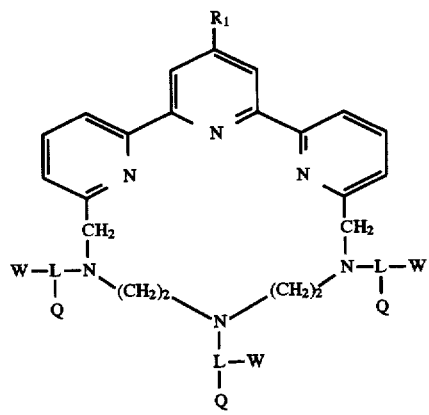

Structure III wherein $R_1$, L, Q, and W are as described above for Structure I.

Specific examples of preferred complexing agents according to the invention include:

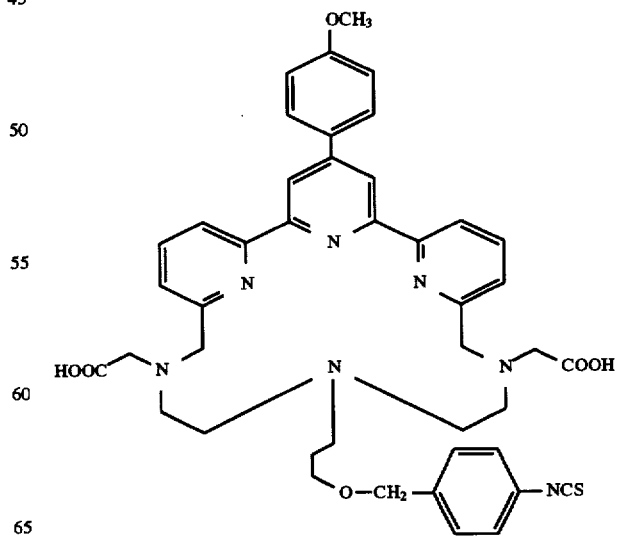

21
-continued
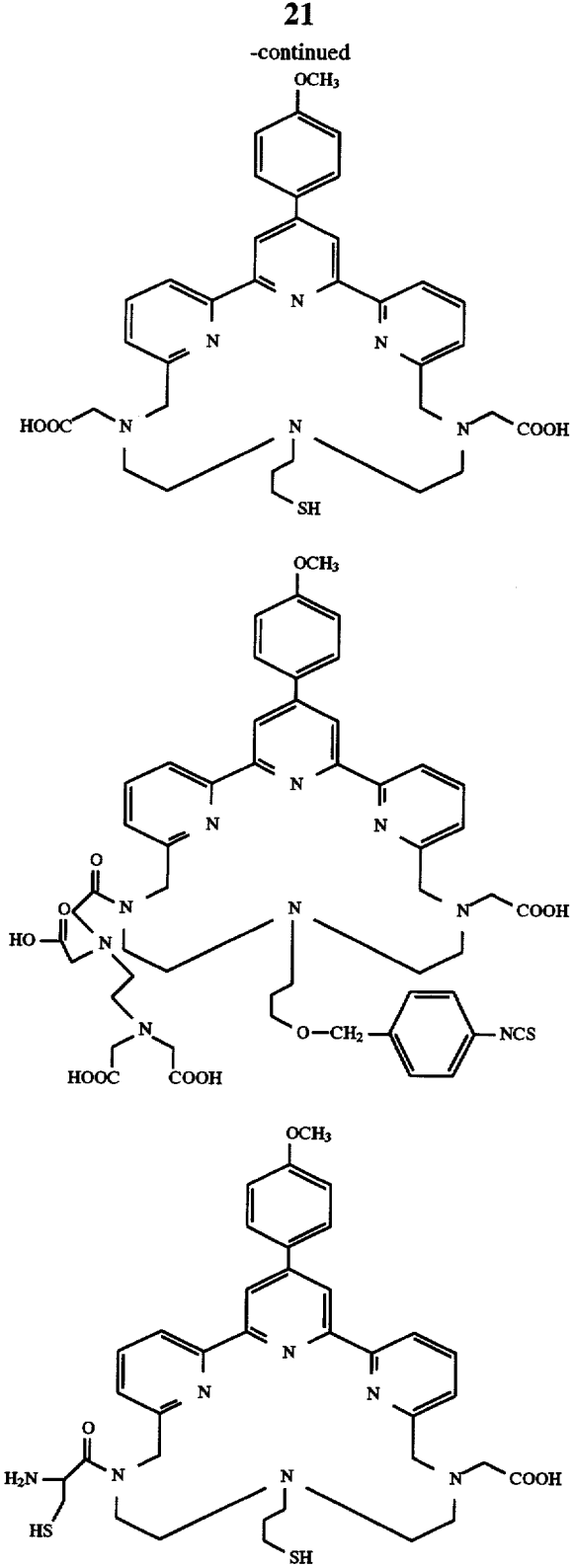
22
-continued
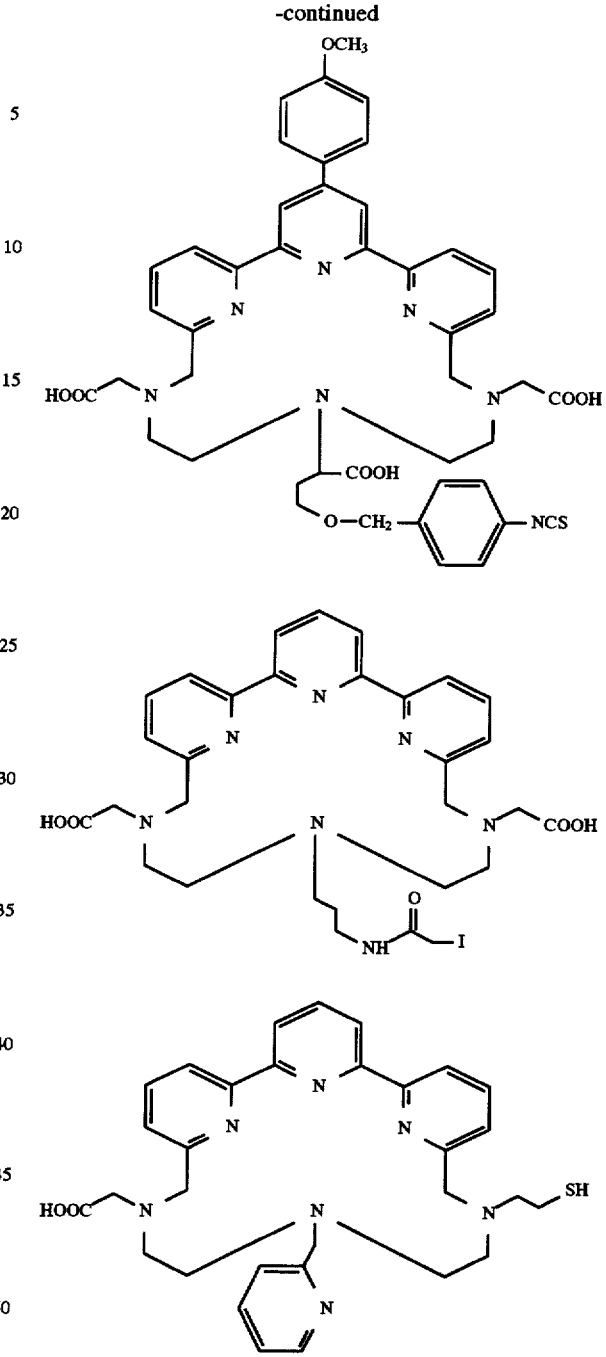

-continued

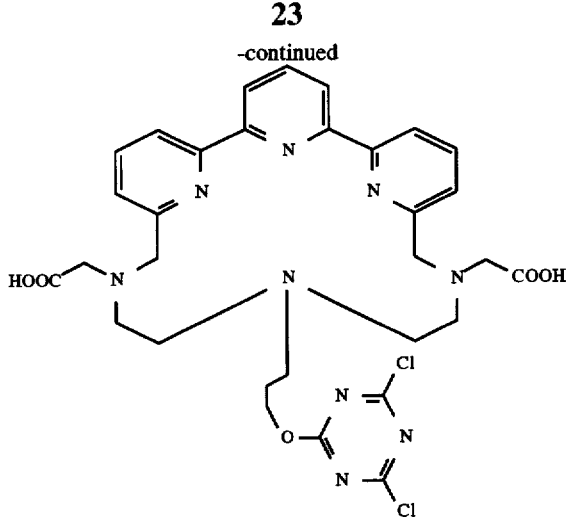

The macrocylic oligo-2,6-pyridine complexing agents of this invention can have multiple metal complexing sites, e.g., oligo-2,6-pyridine sites and additional heteroatom sites.

Suitably substituted oligo-2,6-pyridine moieties can be prepared by techniques known in the art, as for example reviewed by Krohnke in Synthesis, 1 (1976), and used as intermediates in the synthesis of the macrocyclic oligo-2,6-pyridine complexing agents of this invention. Suitable reaction schemes are illustrated in U.S. Pat. No. 4,837,169 and U.S. Pat. No. 4,859,777, the disclosures of which are hereby incorporated herein by reference. A large number of pyridines substituted at the 2- and 6-positions such as, for example, 2,6-dibromopyridine and 2,6-dimthylpyridine as well as at the 4- and 3-, and/or 5-positions such as, for example, 2,4,6-collidine, 2-bromo-5-nitropyridine, and 2,3-lutidine are available commercially, for example, from Aldrich Chemical Company, or can be made according to well known methods illustrated, for example, by R. L. Framk and E. F. Reiner in J. Chem. Soc. (1950), vol 72, pp 4182-3, and can be used as intermediates in the synthesis of the macrocyclic oligo-2,6-pyridine complexing agents of this invention.

The preparation of certain currently preferred compounds of this invention, including compounds 39a, 44, 46a, 49a, 56a, and 57a, below:

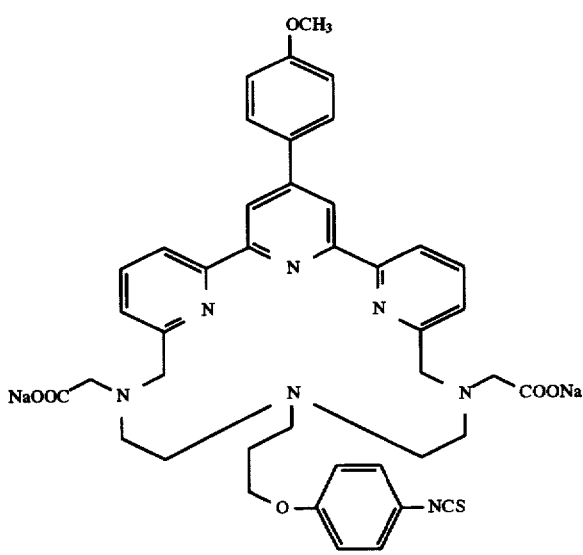

39a

-continued
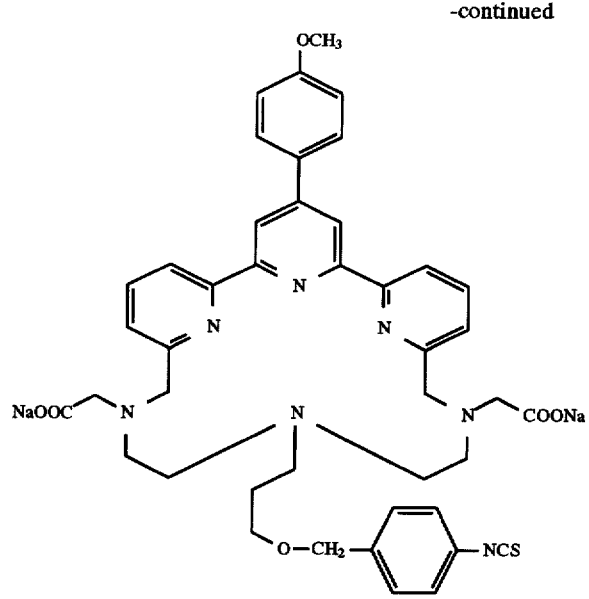
46a
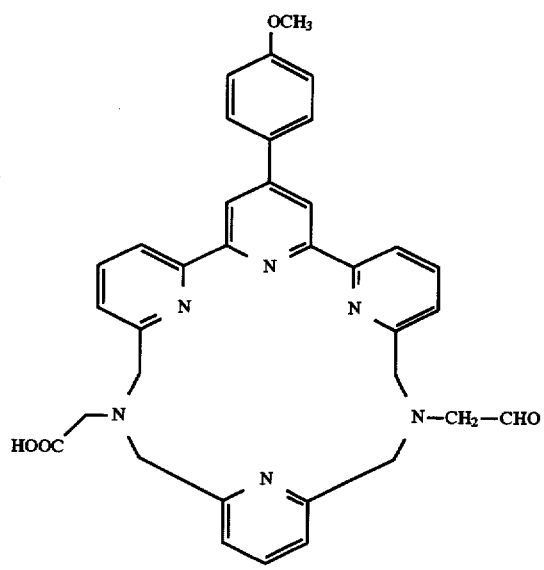
56a
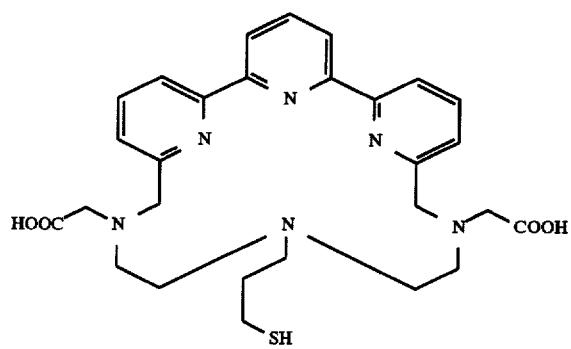
49a

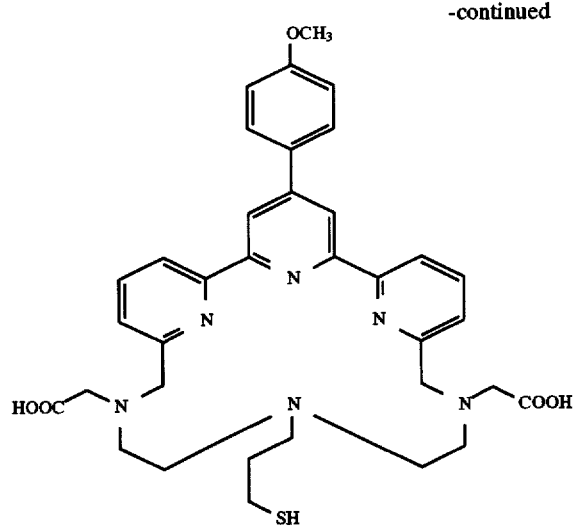
44
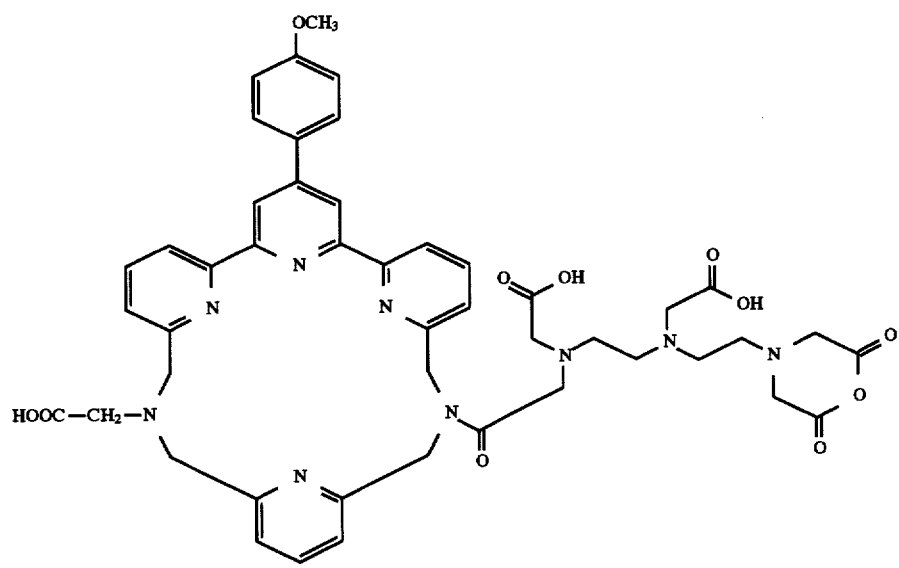
57a
are illustrated in the following reaction schemes.

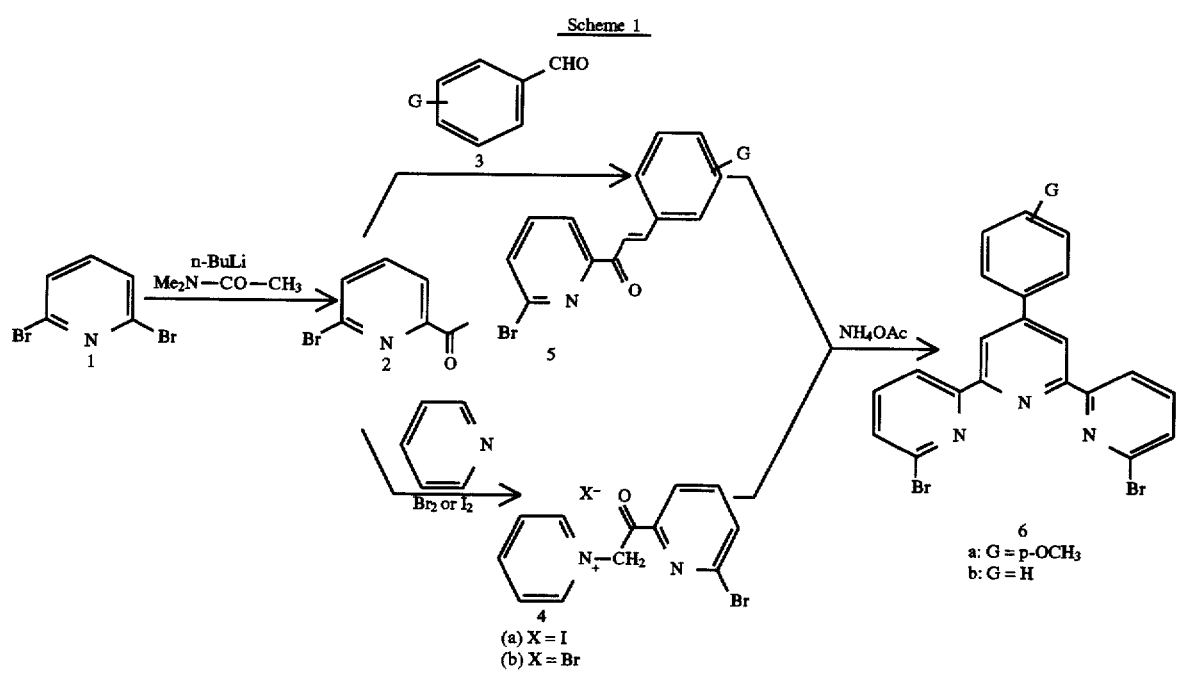
Scheme 1
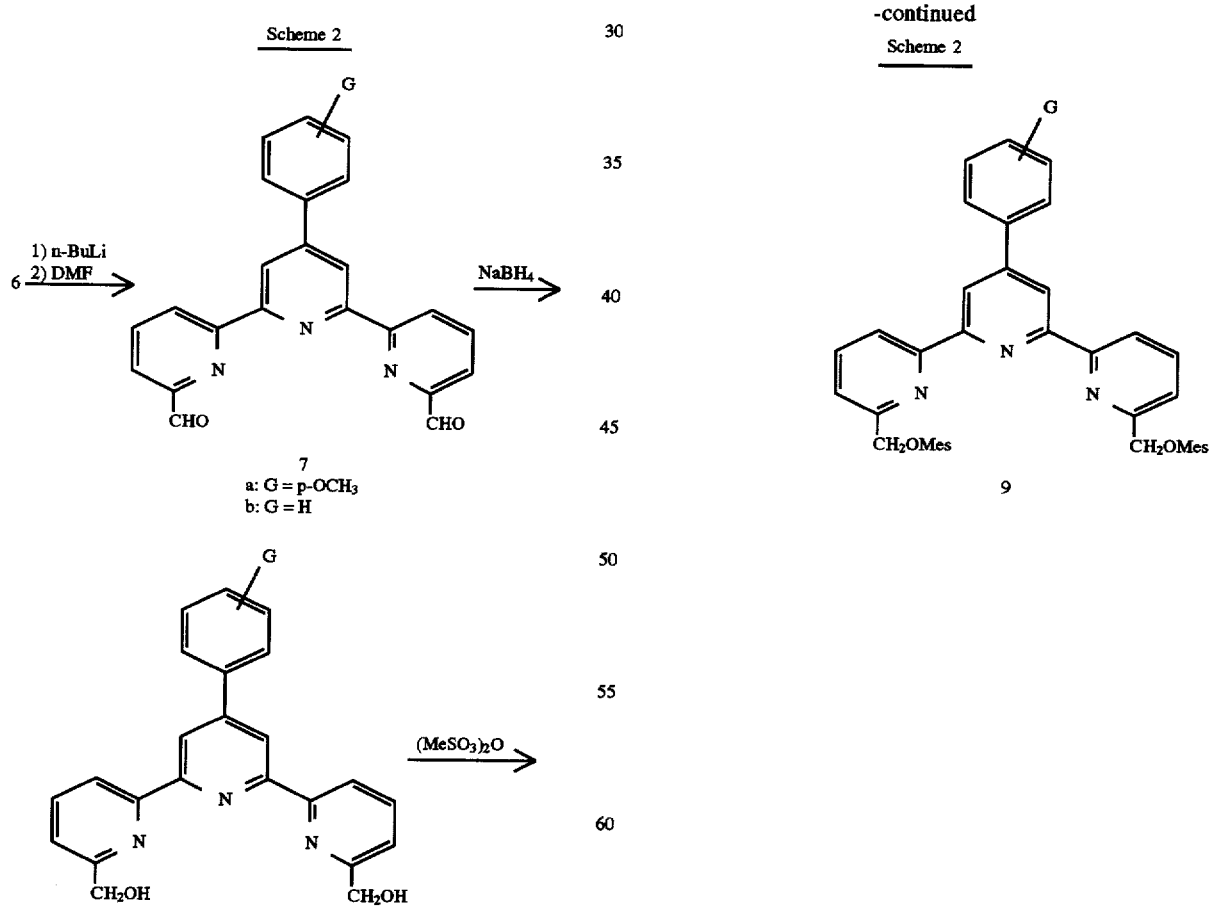
Scheme 2

5,760,191
Scheme 3
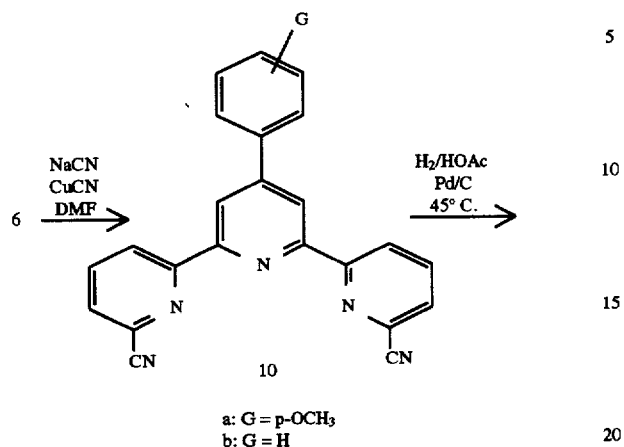
a: G = p-OCH₃
b: G = H
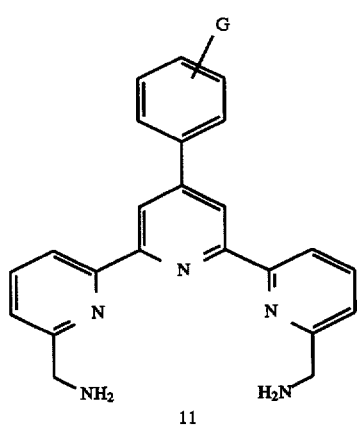
-continued
Scheme 3
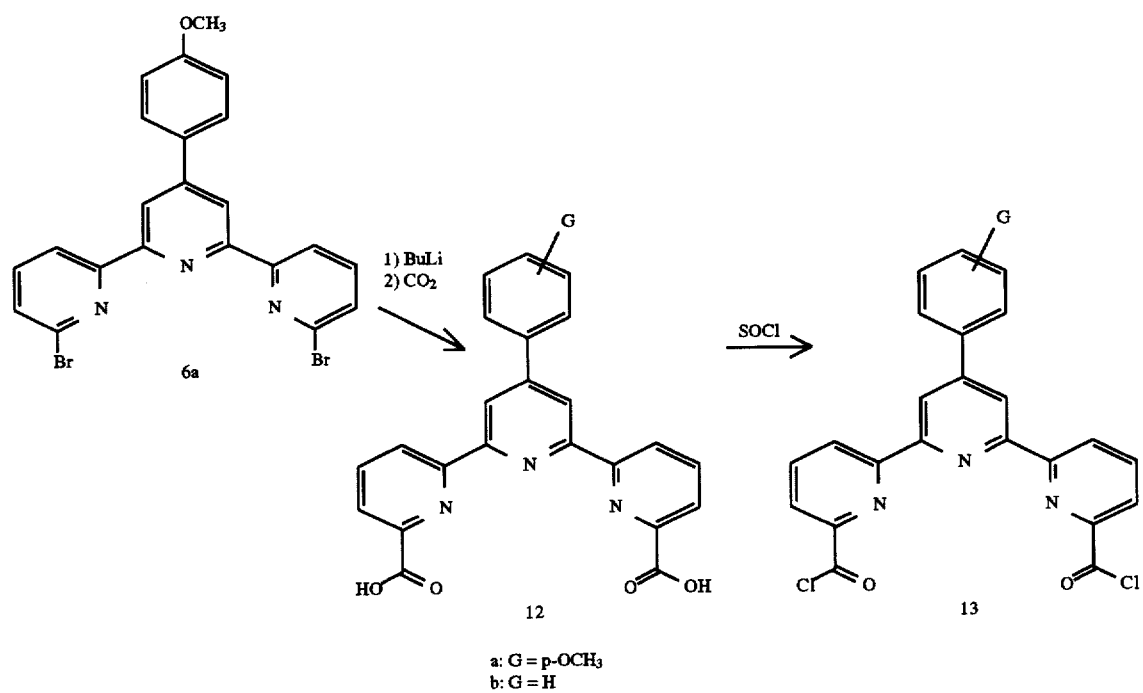
a: G = p-OCH₃
b: G = H
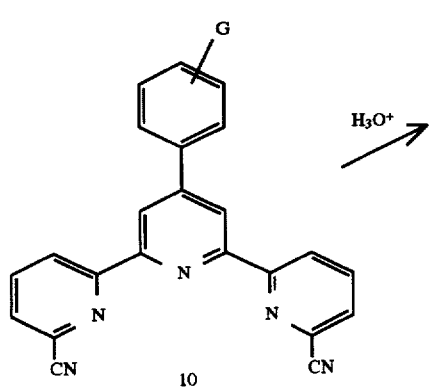

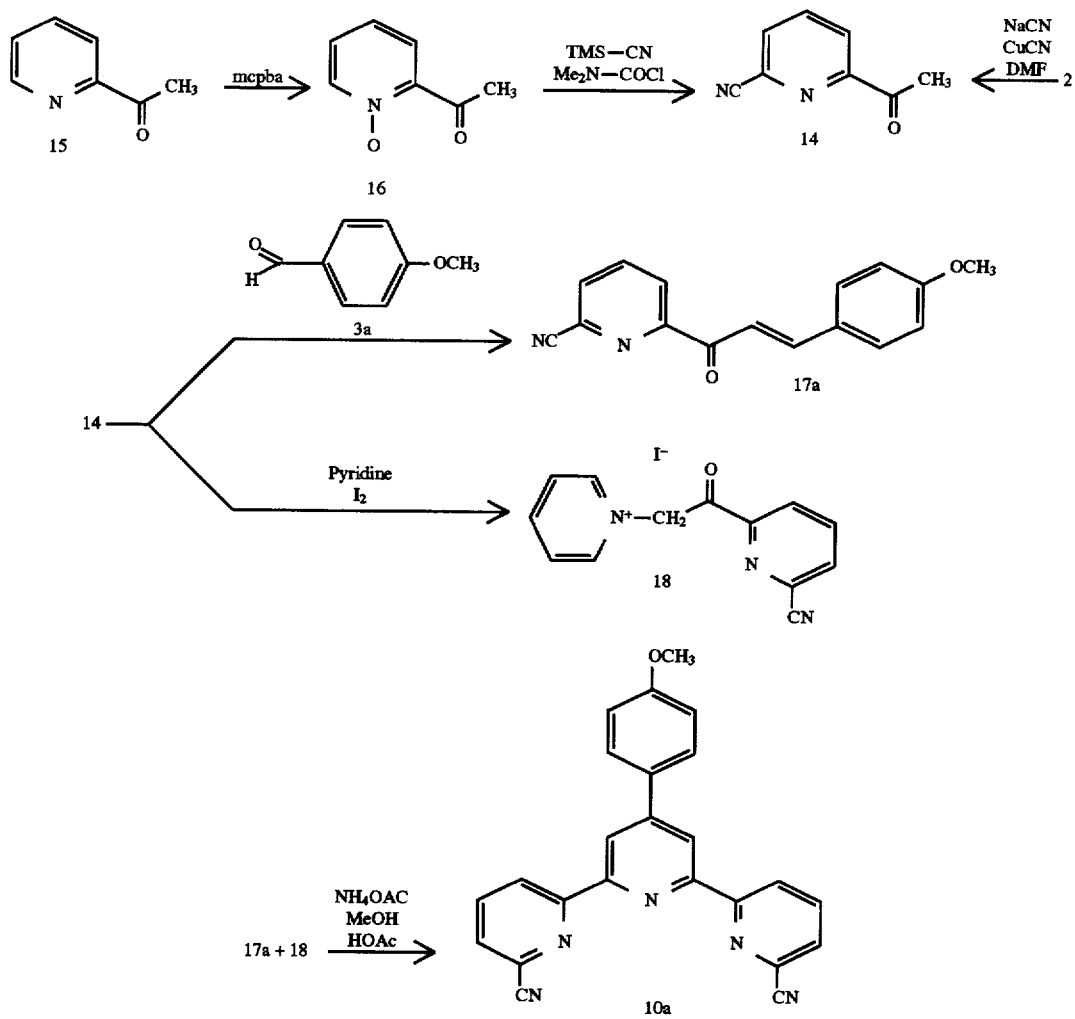
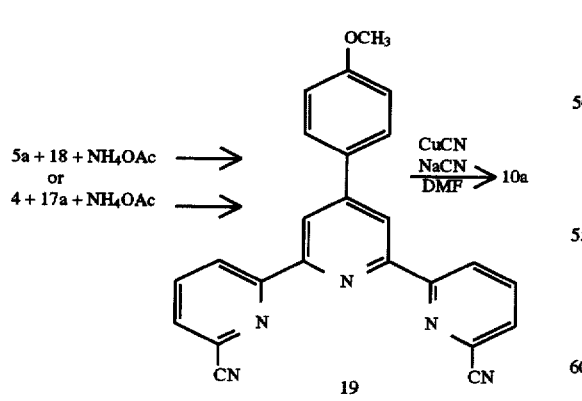
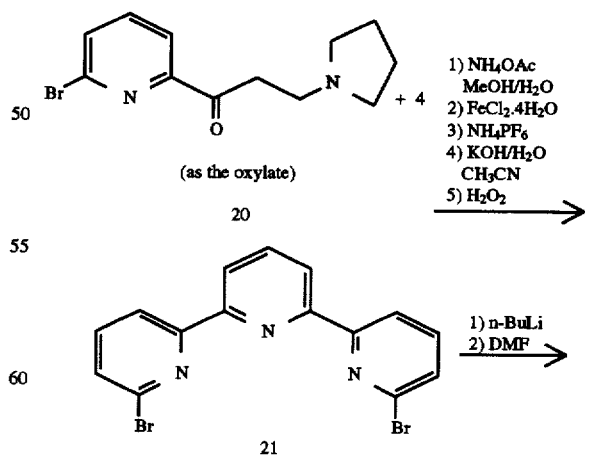

Scheme 7
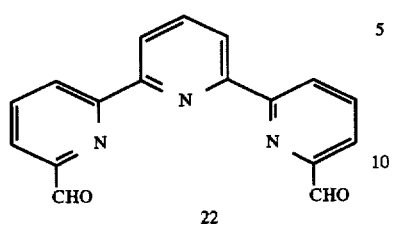
Scheme 8
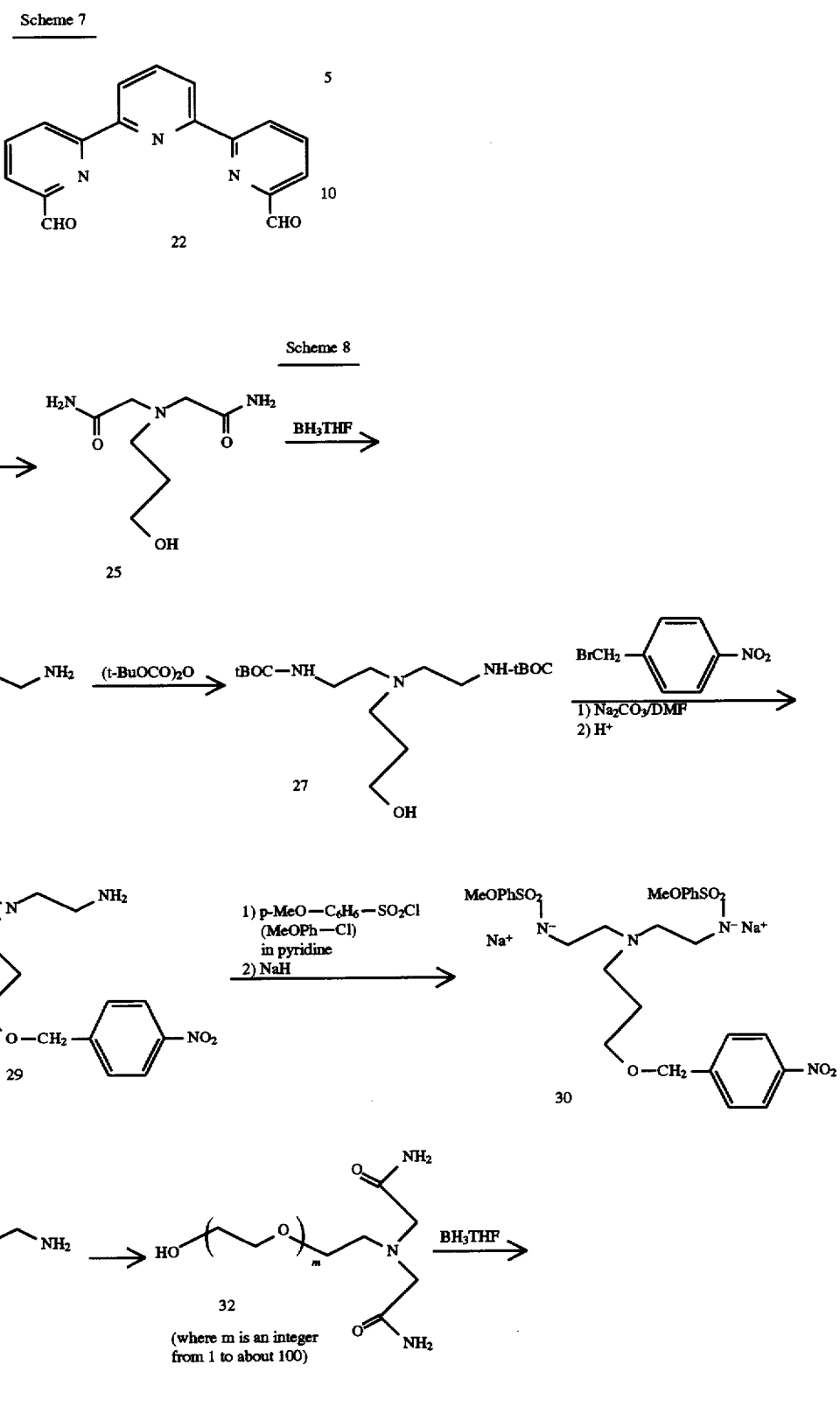

-continued
Scheme 8
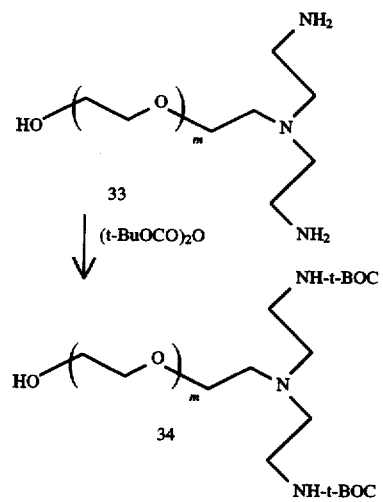
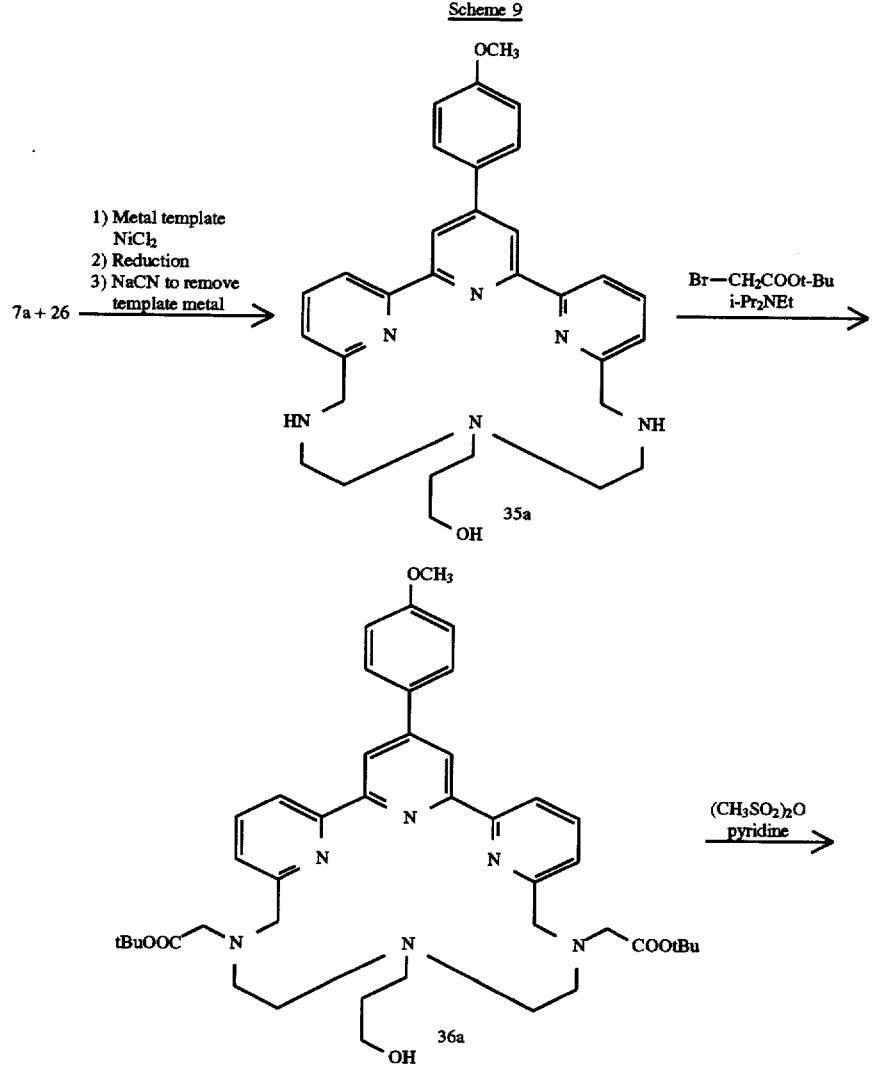

-continued
Scheme 9
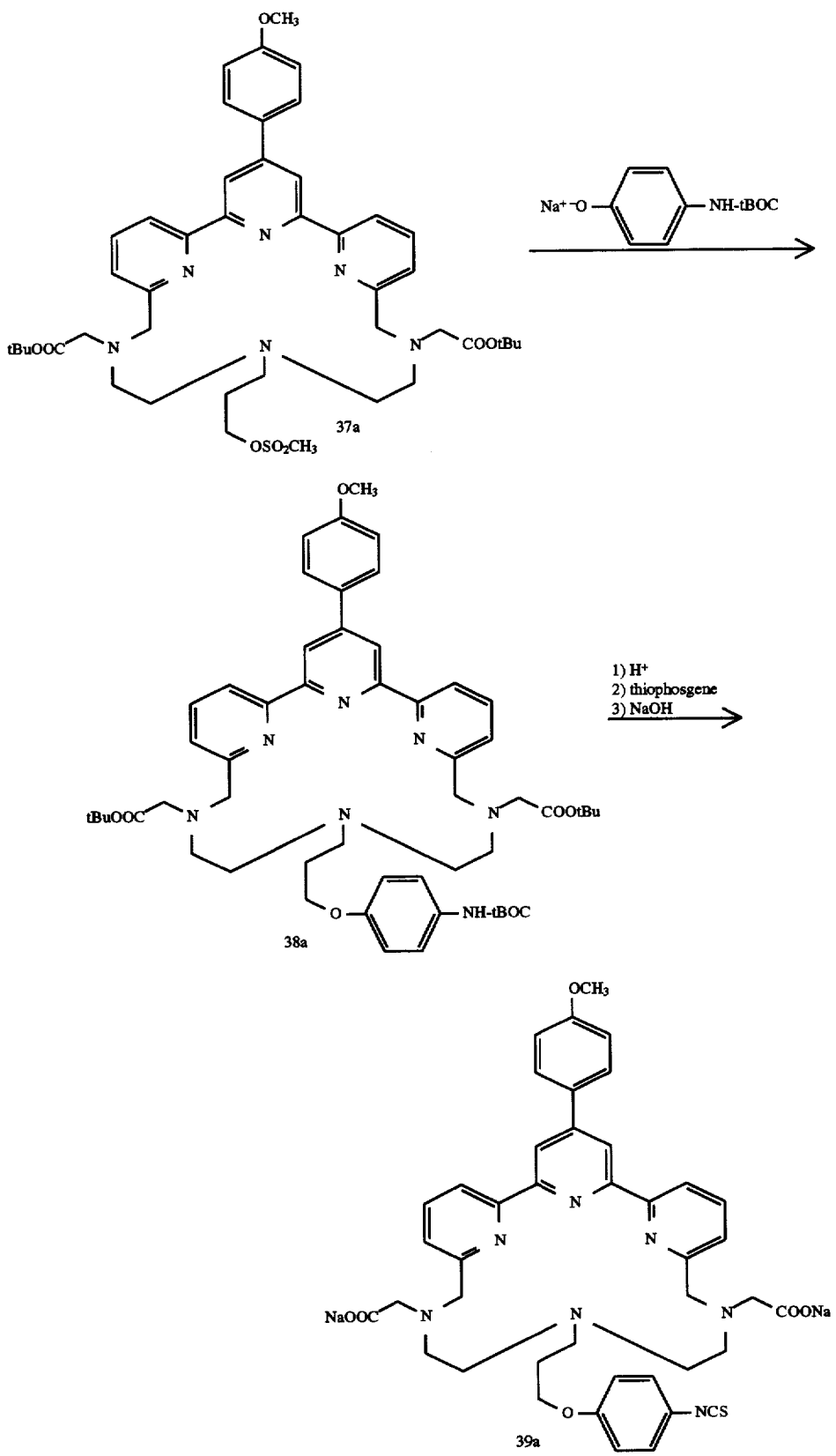

Scheme 10
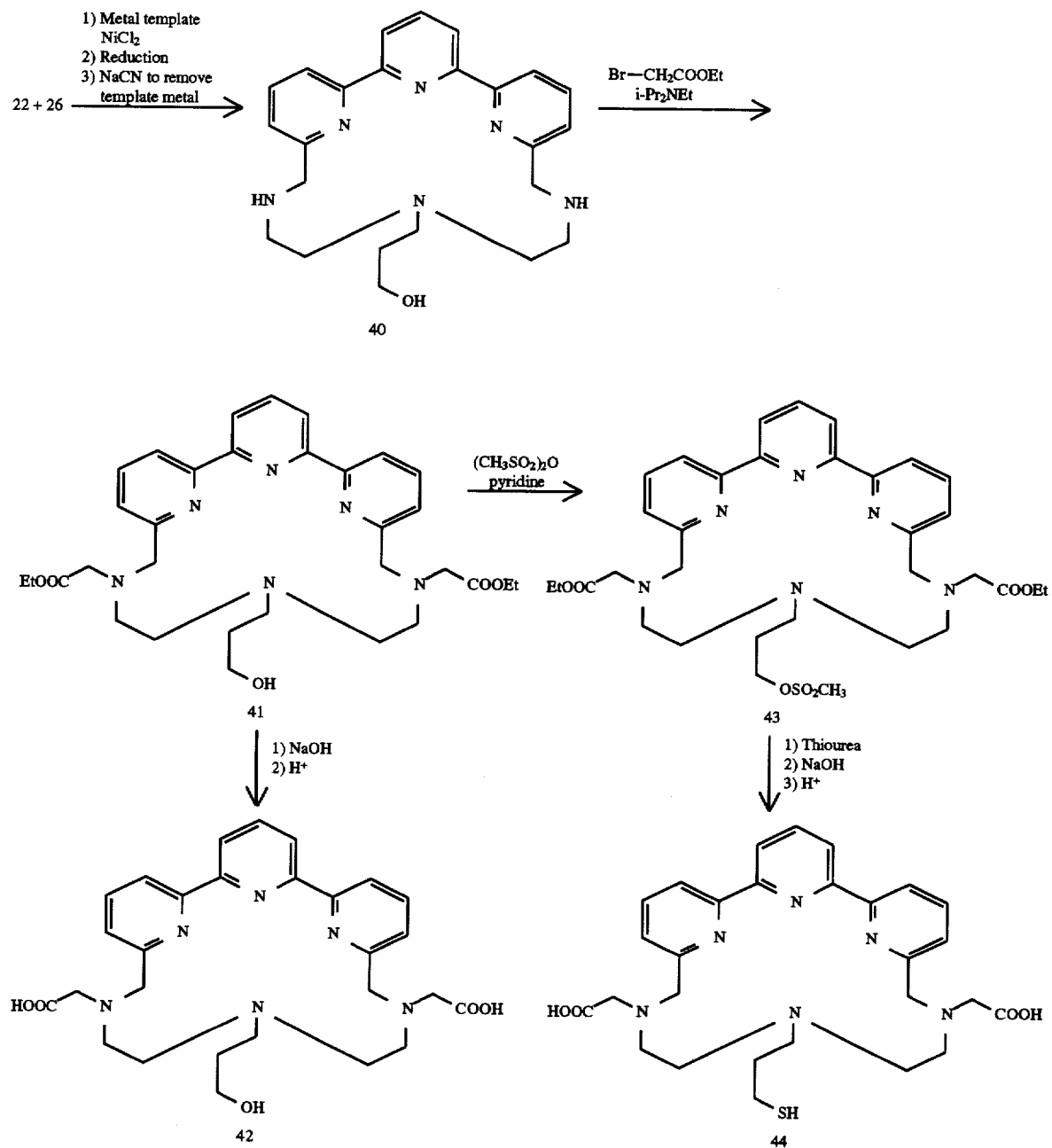

Scheme 11
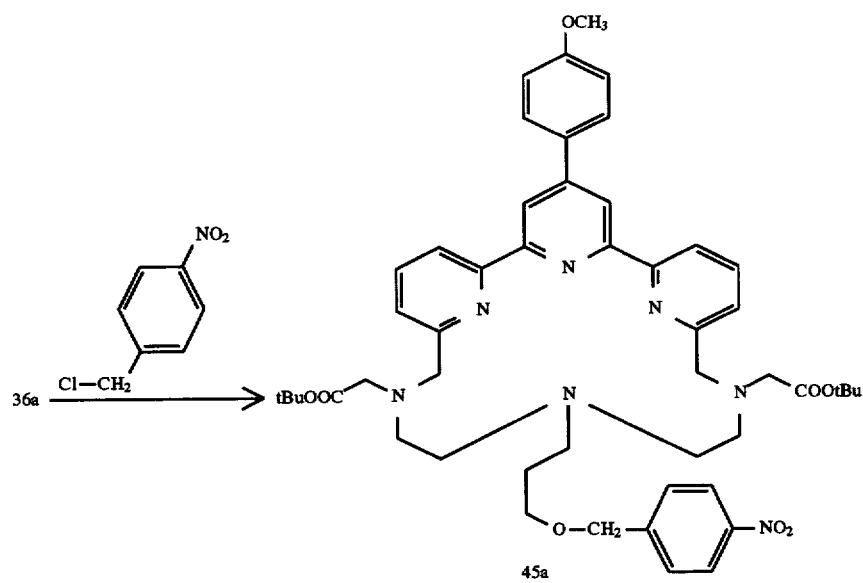
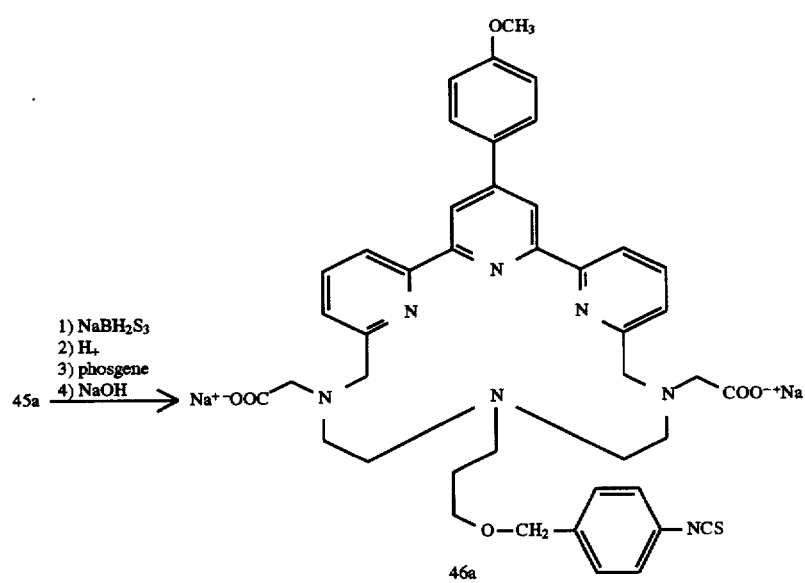

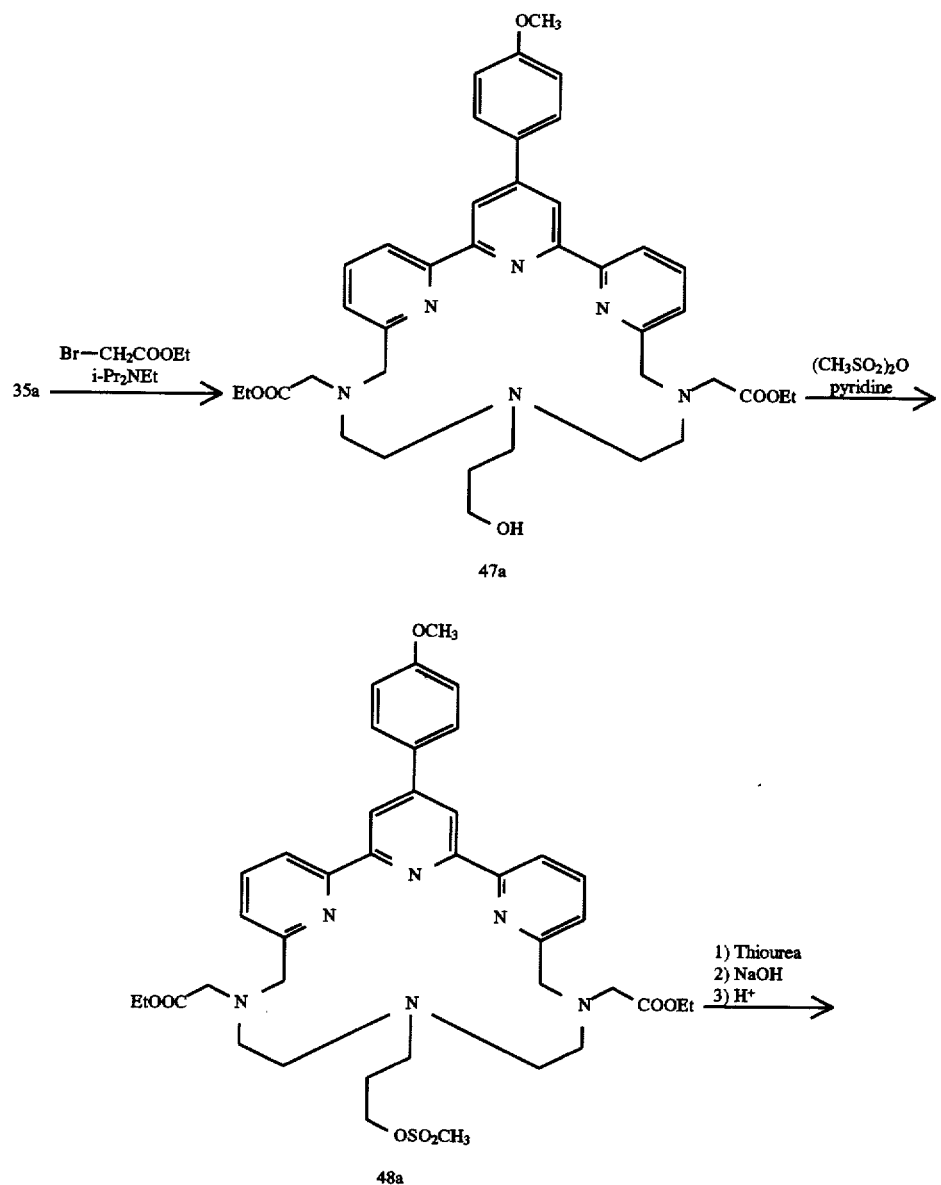

-continued
Scheme 12
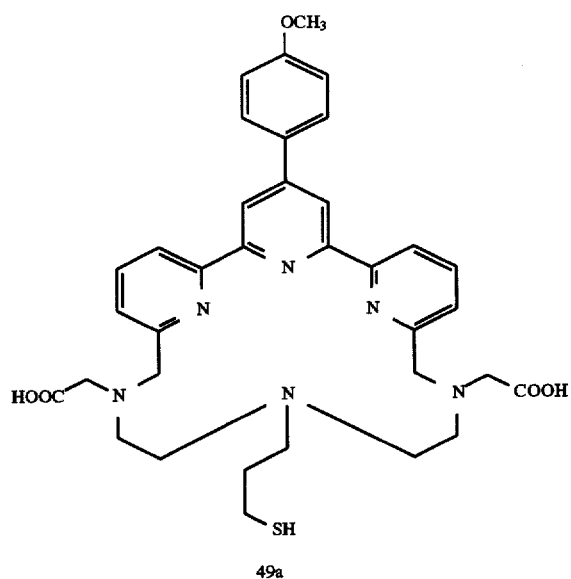
49a
Scheme 13
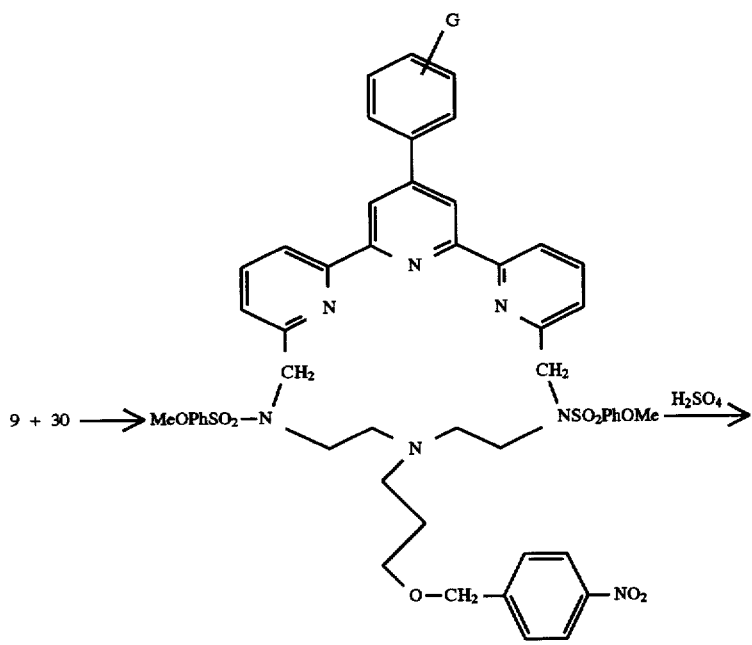
50 a: G = OCH₃
   b: G = H -continued
Scheme 13
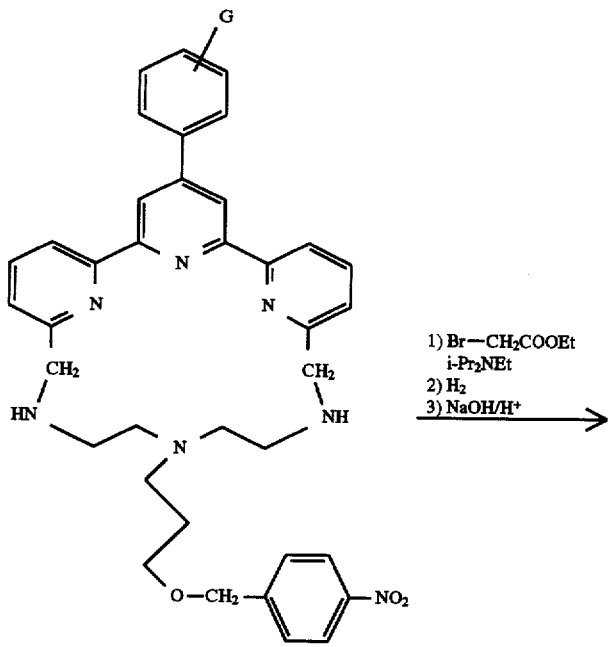
51
1) Br—CH$_2$COOEt
   i-Pr$_2$NEt
2) H$_2$
3) NaOH/H$^+$
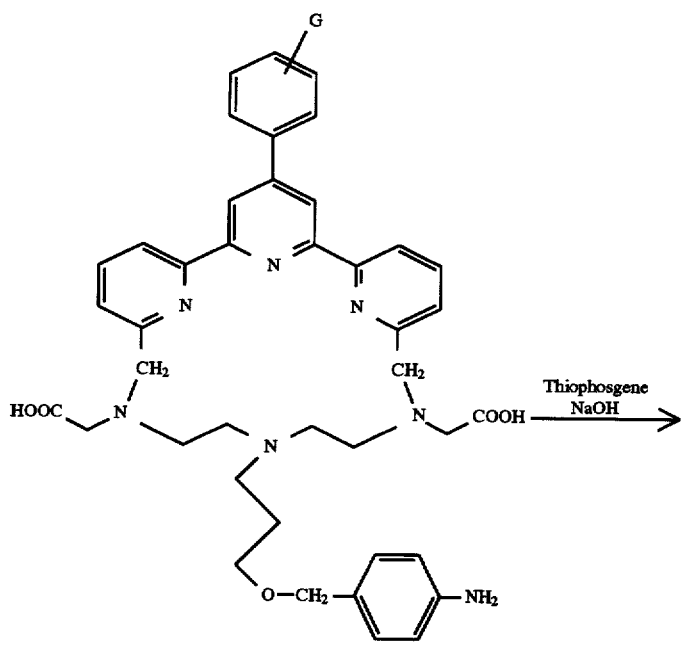
52
Thiophosgene
NaOH -continued
Scheme 13
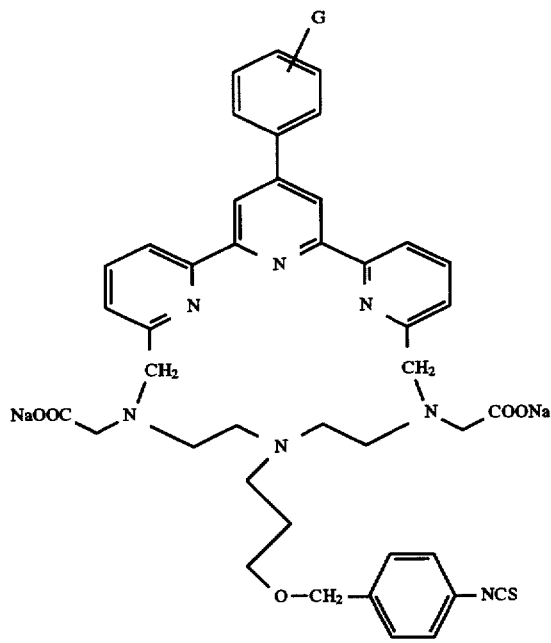
53
Scheme 14
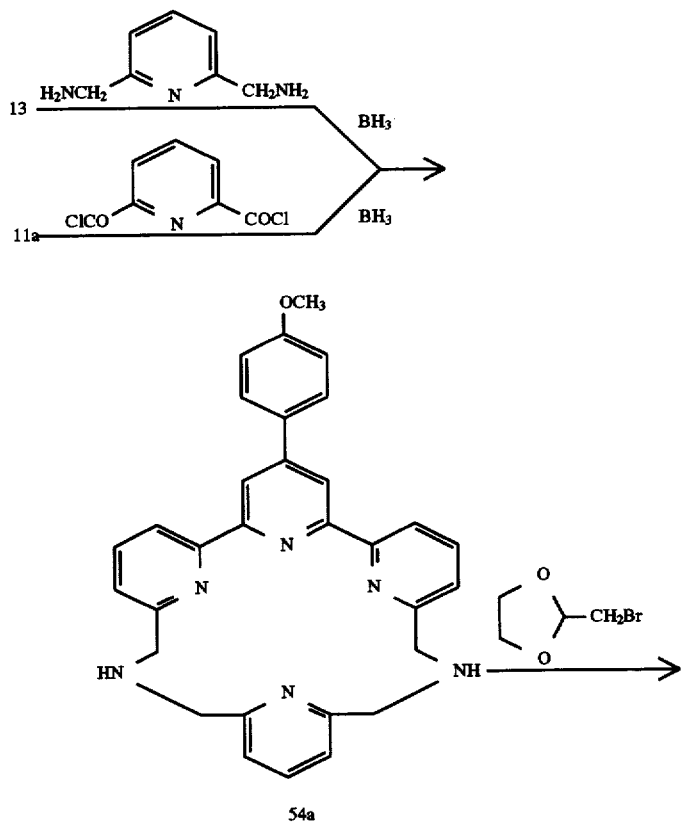
54a -continued
Scheme 14
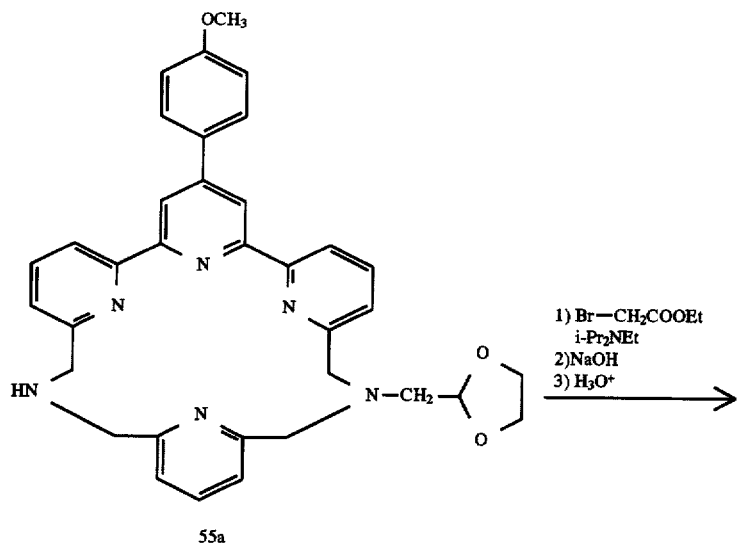
Scheme 15
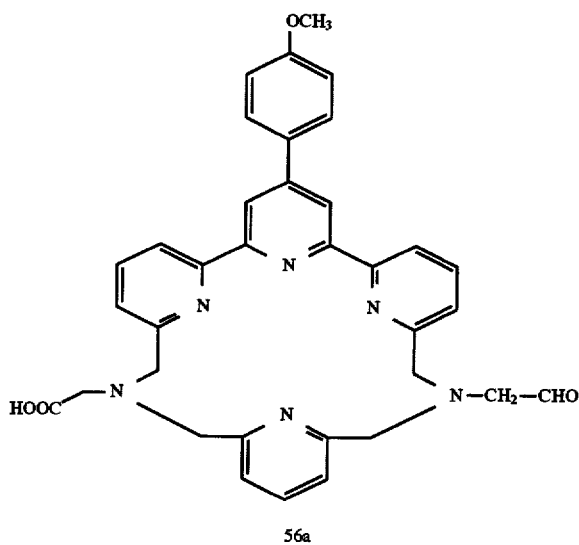
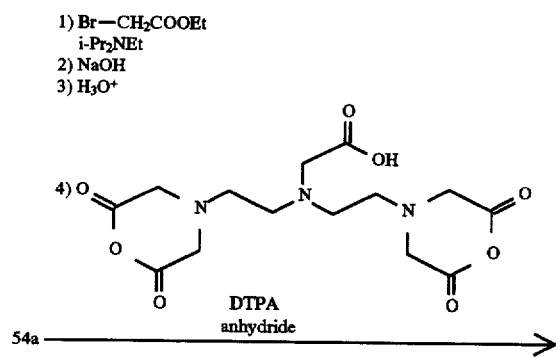

-continued
Scheme 15

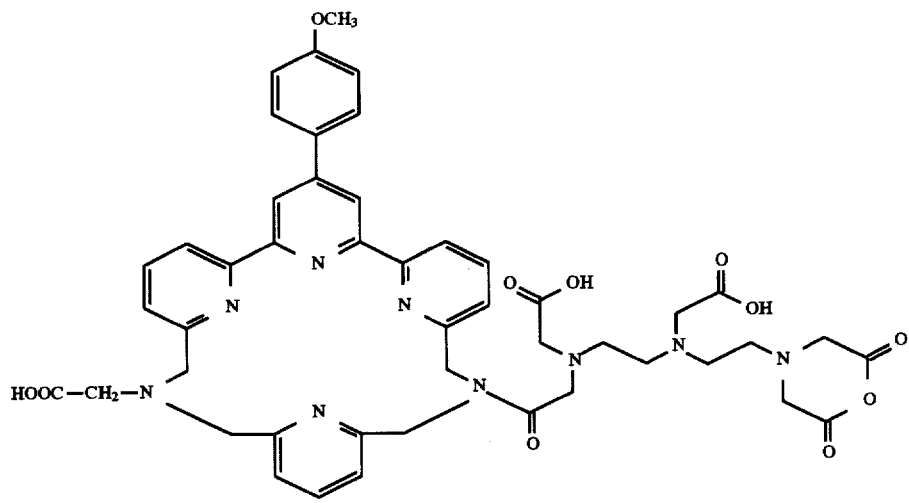

57a

The introduction into the complexing agents of this invention of the requisite protein reactive groups described above can be accomplished by conventional chemical reactions. For example, in the absence of readily nitrated groups (for example, in the absence of phenyl groups) at the 3-, 4-, and 5-positions of the oligo-2,6-pyridine moiety of the macrocycles of this invention, i.e., when each of R and Ri is a non-phenyl group such as hydrogen or an alkyl group, a substituent at one X in Structure I comprising a phenyl group can be converted by nitration to a nitrophenyl group which can be reduced to an aminophenyl group. If desired, the amine of the aminophenyl group can be readily converted to an isocyanate group by reaction with phosgene to produce a carbamoyl chloride group which, upon heating, releases HCl to produce an isocyanate group. Carboxy groups can be added at the amine of the aminophenyl group by treatment of amine with reagents such as glutaric anhydride, followed by suitable selective activation of the amide-linked carboxyl functionality. Cyclic acetal protected aldehydes can be carried through at least one step in the reaction sequence necessary to synthesize the macrocyclic oligo-2,6-pyridine chelators, and then deprotected, for example, by acidic hydrolysis before protein conjugation.

Alternatively, a functional group such as a hydroxyl group can be introduced into a substituent of one X during the macrocyclic ring forming reaction. For example, a 3-hydroxypropyl group can be introduced as a substituent of X when X is a nitrogen. This can be done, for example, with a reagent such as N-(3-hydroxypropyl)-N,N-bis(2-aminoethyl)amine. In this case, reductive amination of this triamine with an oligo-2,6-pyridine containing an aldehyde group at each of the first and the final 6- and $6^{()n-1}$ positions of the oligo-2,6-pyridine (i.e., at each of the 6 and the 6" position of a terpyridine, at each of the 6 and the 6'" position of a quaterpyridine ring, etc.), optionally in the presence of a metal template such as a nickel ion, followed by removal of the metal template ion such as by using excess cyanide ion, and then alkylation of the thus formed secondary amines with groups such as bromoacetic acid or ester groups provides a 3-hydroxypropyl group as a substituent. This hydroxy group can then be converted into a sulfonic acid ester with, for example, methoxybenzenesulfonic acid anhydride or methanesulfonic acid anhydride in pyridine, the thus formed sulfonate can be reacted with sodium azide, and the thus formed azido compound can be reduced to an amino group, i.e., a 3-aminopropyl group. This amino group can react with an aldehyde introduced into a carbohydrate portion of an immunoreactive group under reductive conditions (e.g., in the presence of sodium cyanoborohydride at a pH of about 5 to about 6). In addition, the amine groups introduced as described above can be further modified using, for example, commercially available heterobifunctional crosslinking reagents as described below to introduce sulfhydryl groups and active olefin groups such as maleimide groups into the substituent attached to an X of structure I.

In compounds represented by Structure I wherein one Q comprises a hydroxyl group and R and $R_1$ comprise non-hydroxyl group-containing substituents such as, for example, hydrogen, alkyl, aryl and ether groups, sulfhydryl groups can be introduced, for example, by conversion of a hydroxyl group substituent into a halide using thionyl chloride or to a sulfonate using, for example, methanesulfonic acid anhydride or an aryl sulfonyl chloride; both the halide and the sulfonate groups thus formed can then be reacted with thiourea and the resulting thiouronium salt can be reacted with base to produce a sulfhydryl group. Alternatively, an amine group can be reacted with N-acetyl homocysteine to form an amide bond and simultaneously introduce a sulfhydryl group linked thereto.

The class of macrocyclic oligo-2,6-pyridines conforming to Structure III above wherein R is hydrogen, $R_1$ is a phenyl group containing an alkyl or alkoxy group, and one Q comprises a protein reactive group containing a propyl group which has a heteroatom in the 3-position of said propyl group is particularly advantageous from a synthetic standpoint. For example, the presence of the alkyl or alkoxy group on the dibrominated intermediate (6) provides enhanced solubility in THF, which is a preferred solvent for use in the preparation of the intermediate dialdehyde (7). The presence of the alkyl or alkoxy group also provides enhanced solubility in DMF in the formation and isolation of macrocyclic intermediates such as (35a) and (40).

Thus, in compounds (35a), (40) and related compounds such as (42), the heteroatom at the 3 position of the propyl group is a hydroxyl oxygen. In this class of compounds, such hydroxyl group is readily converted into a variety of protein reactive groups. Those represented in Schemes 9, 10, 11, and 12 above are examples.

Several other synthetic routes can be applied to generate derivatives of compounds (35a) and (40) which contain protein reactive groups connected to the propyl group at the heteroatom 3-position. Compound (42), a derivative of compound (40) is used in the following to illustrate examples of such conversions.

Alcohol (42) can be treated with divinyl sulfone to form the monoaddition compound (59) that provides a vinyl sulfone protein reactive group.

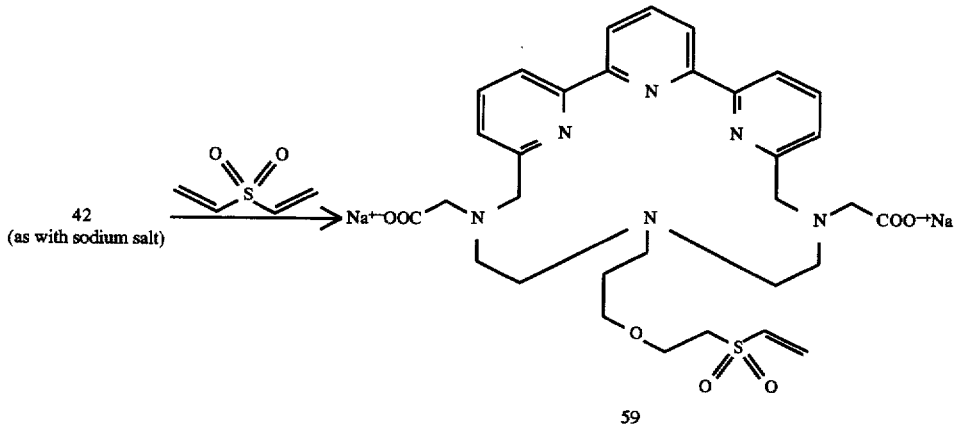

Alternatively, the reaction outlined in Scheme 10 to generate (40) from (26) can be employed, for example, using the poly(ethylene glycol) analog (33) in place of (26) to generate, after subsequent reaction with t-butyl bromoacetate, of the corresponding bis(acetic acid) derivative, (58), from (22). (58) can then be treated with divinyl sulfone to form the vinyl sulfone (59a). The reaction with divinyl sulfone is preferably base catalyzed. In (58 and 59a), m is an integer in the range from 1 to about 100.

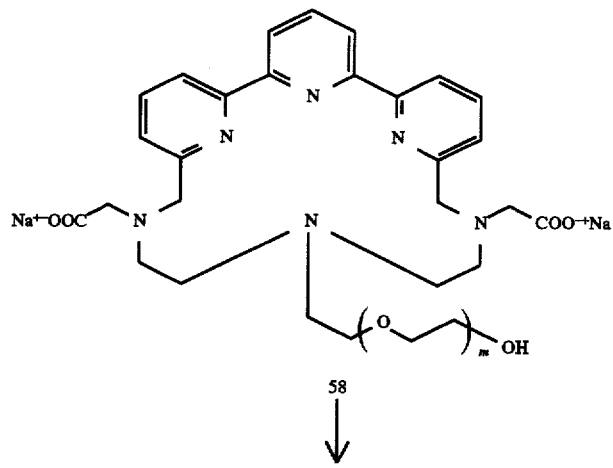

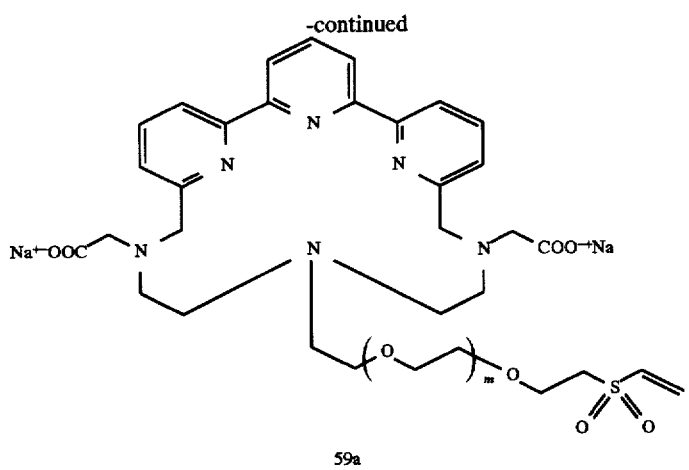

59a

Alcohol (42) can also be treated with an aryl chloroformate such as p-nitrophenyl chloroformate or 2,4,5-trichlorophenyl chloroformate to produce the carbonate (60). Carbonate (60) can react with amine groups on proteins such as amines in lysines and at peptide amine termini. Of course, the incorporation of amine-reactive protein reactive groups into the macrocyclic chelating agents of this invention preferably requires that no amine functionality capable of reacting with the protein reactive group be present elsewhere in the structure of the chelating agent.

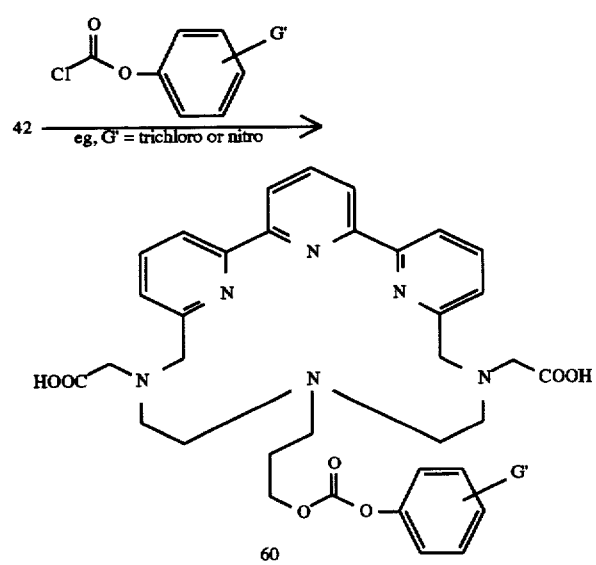

Alternatively, (42) can be reacted directly with cyanuric chloride to produce the cyanurate (61). This dichlorocyanurate can react with amine groups on proteins.

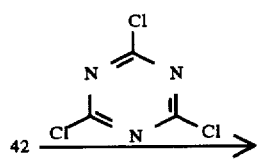

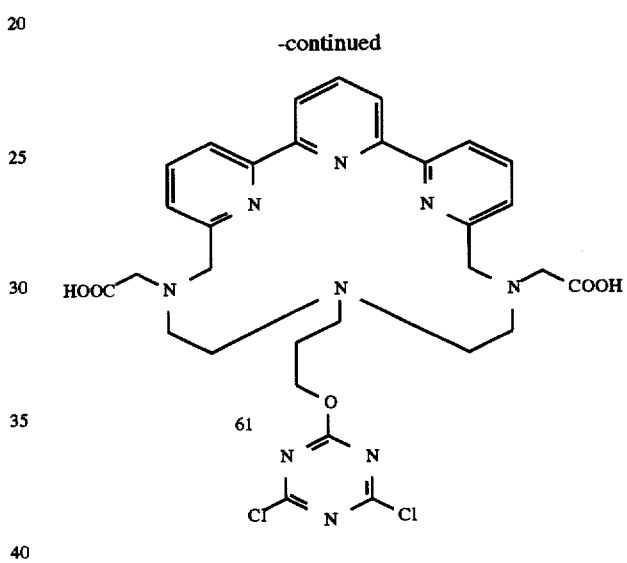

Alternatively, the sodium salt of alcohol (42) can be converted to aldehyde (62) by treatment with, for example, 2-bromomethyl-1,3-dioxolane. Carboxylic acid esters of methyl-1,3-dioxolane formed during the reaction can be saponified to liberated the carboxylic acid group from the ester group, and the aldehyde can be liberated from the cyclic acetal by deprotection with aqueous acid. This aldehyde is suitable for use in reductive amination procedures (e.g., those incorporating the use of sodium cyanoborohydride as the reducing agent at a pH in the range of 4 to 7, preferably about pH 6, in an aqueous system) for the linking of the aldehyde to an amine on a protein.

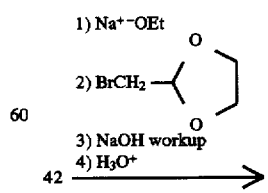

61
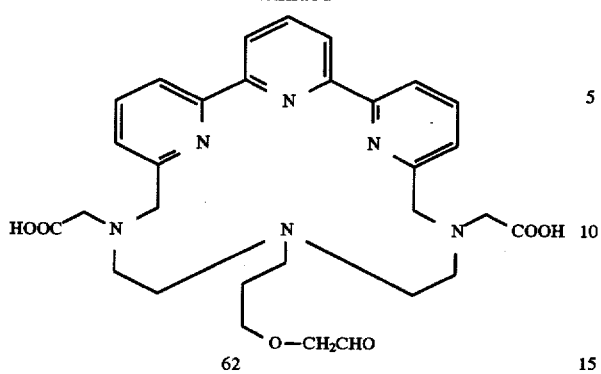
62
Alternatively, alcohol (40) can be converted to the di-t-butyl ester (63) by reaction with t-butyl bromoacetate. This alcohol can then be converted to the sulfonate (64) using methanesulfonic anhydride in pyridine, and the sulfonate can be then converted to amine (65) by treatment with sodium azide followed by reduction with triphenylphosphine.
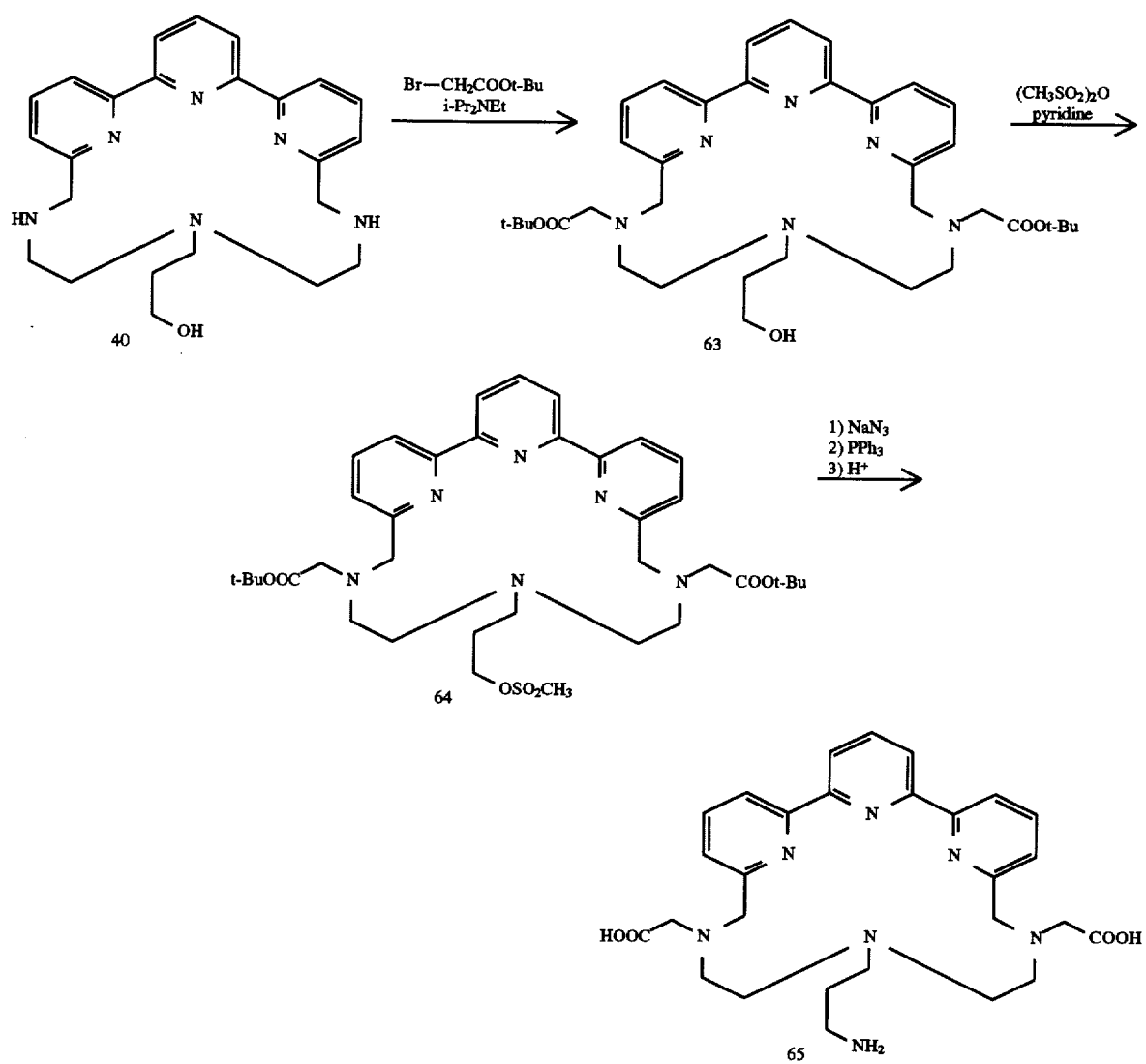

63

Similar chemistry can be applied to alcohol (36a) to produce amine (66).

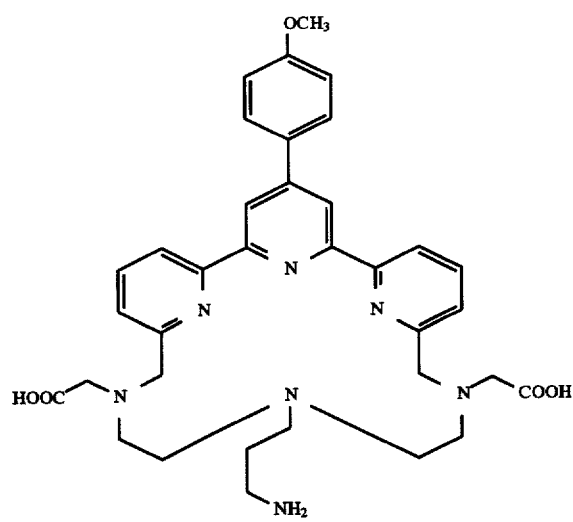

The above aliphatic amines can be attached to proteins in several ways. For example, they are suitable for use in reductive amination procedures (e.g., incorporating the use of sodium cyanoborohydride as the reducing agent at a pH of about 6 in an aqueous system) to couple the amine with an aldehyde functionality that is generated by the action of an oxidizing agent such as sodium periodate on a carbohydrate moiety attached to a protein (such as an antibody). Aldehyde functionality can also be generated on a protein using reagents such as 4-azo-phenylglyoxal (APG, available from Pierce Chemical Co.) which reacts selectively with arginine residues on the protein. These aldehydes can then be reacted with an amine such as (65) or (66), above.

In addition, these amines can be attached to proteins by first being further elaborated with commonly available heterobifunctional reagents (such as are available commercially from Pierce Chemical Company). For example, amine (65) can be treated with 2-iminothiolane to generate (67) or with N-succinimidyl S-acetylthioacetate (SATA) followed by treatment with hydroxylamine to generate (68). These species as well as sulfhydryl species (44) and (49a) contain free sulfhydryl SH groups which can react with maleimide functionality that can be introduced at amine sites in a protein using reagents such as SMCC [N-(4-carboxycyclohexylmethyl)-maleimide N-hydroxysuccinimidate] and the like.

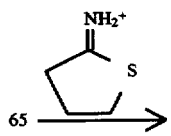

64
-continued

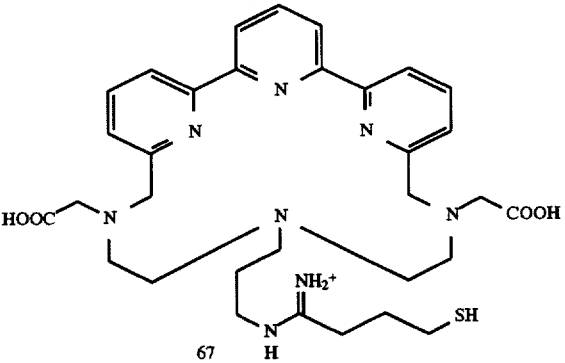

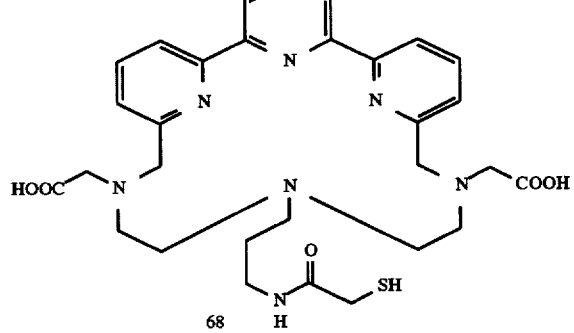

In addition, amines such as (65) can be treated with SMCC [N-(4-carboxycyclohexylmethyl)-maleimide N-hydroxysuccinimidate] to generate maleimide-containing species such as (69). The maleimide functionality can react with free sulfhydryl groups that can be introduced at amine sites in a protein using reagents such as 2-iminothiolane or N-succinimidyl S-acetylthioacetate (SATA) followed by treatment with hydroxylamine. Free sulfhydryl sites can also be generated in a protein by the action of sulfhydryl-containing reducing agents such as dithiothreitol on disulfide bonds which may be present in the protein or desired protein fragment.

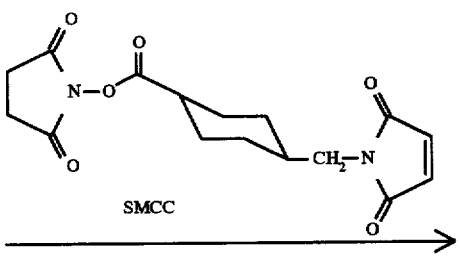

-continued

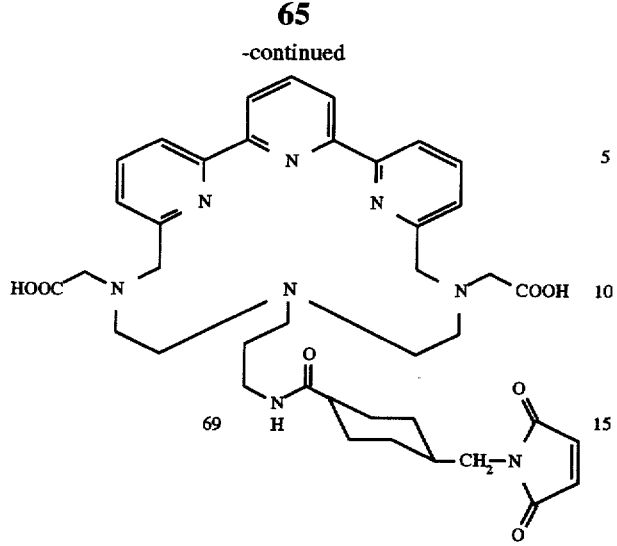

Also within the scope of this invention is the generation of linking chemistries from an aromatic amine such as that defined in (52) as well as amine intermediates generated by acid hydrolysis (H+) in the preparation of isothiocyanates (39a) and (46a). Aryl amine (52) can be treated with aqueous hydrochloric acid and sodium nitrite to form the diazonium salt (70). This material can be coupled to tyrosine moieties on proteins via diazo linkages to the aromatic ring containing the hydroxyl group. This is represented schematically as (71) wherein

represents a protein Such as an antibody moiety containing a tyrosine hydroxy-aromatic ring (such as, for example, a tyrosine in an antibody such as ING-1 as described below).

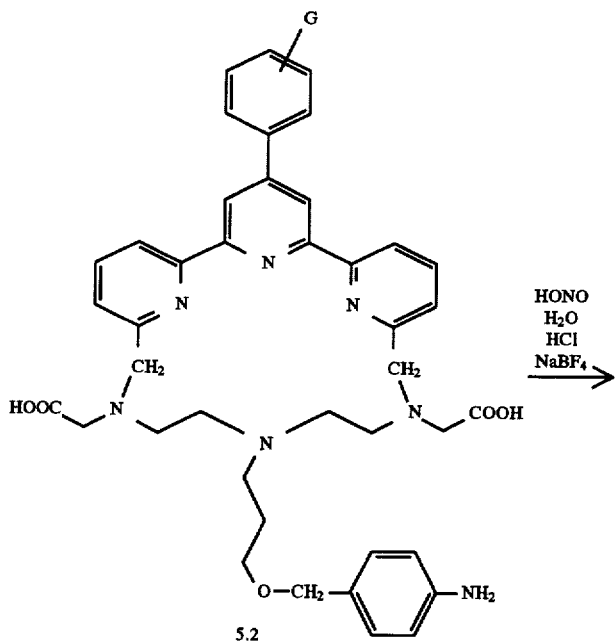

a: G = OCH₃
b: G = H

-continued

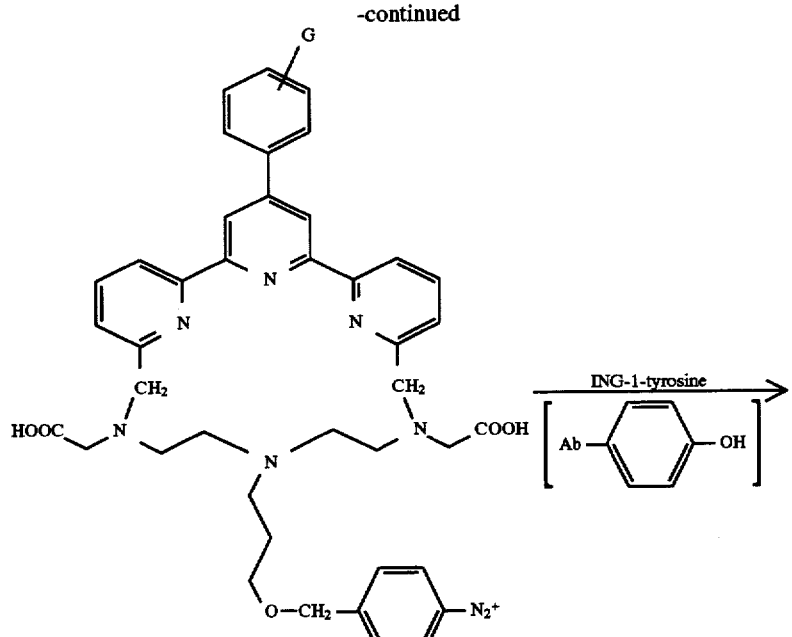

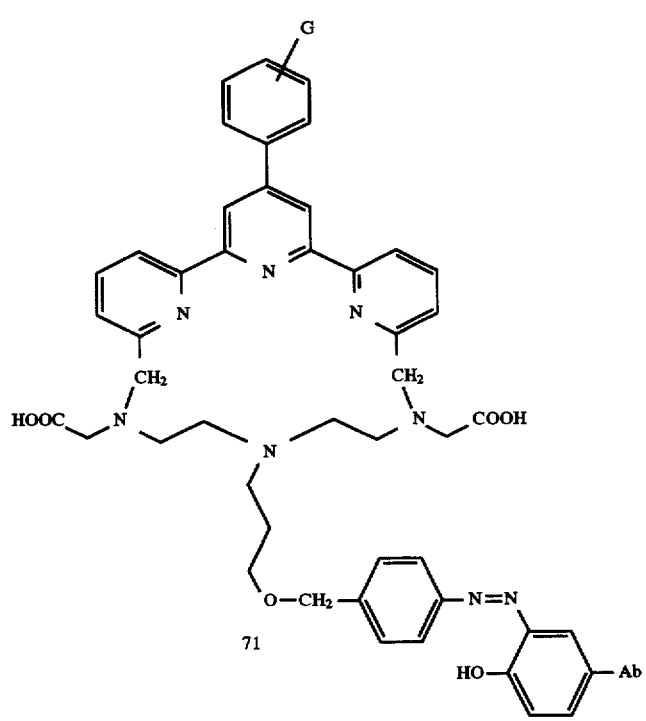

In addition, amine (52) can be treated with excess cyanuric chloride to produce the dichlorocyanuramide (72) and with 2-methoxycyanuric dichloride to produce the chloromethoxycyanuramide (73). Both of these derivatives can be reacted at amine groups such as lysine amines or the terminal amine groups of peptide chains in proteins. Reaction occurs via the displacement of chloride from the triazine ring.

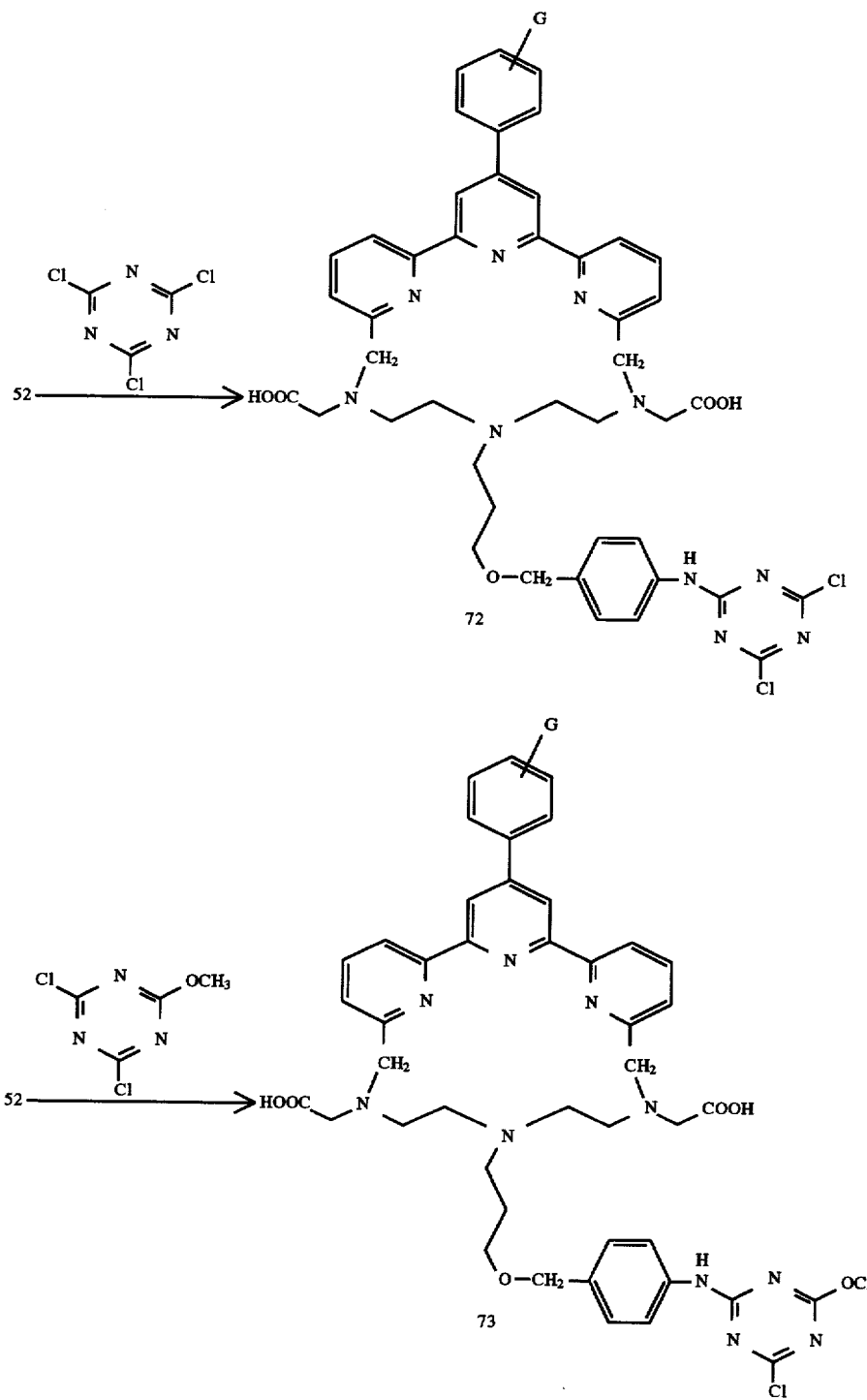

In addition, amine (52) can be reacted with the N-hydroxysuccinimido ester of alpha-iodoacetic acid or with alpha-iodoacetic acid anhydride to produce the iodoacetamide derivative (74). This material can be reacted with proteins containing free sulfhydryl groups such as those utilized in the reactions of maleimide derivative (69) above. Iodoacetamide (74) will also react with amines on proteins, such as the epsilon amine of lysine and the terminal amine of a peptide chain.

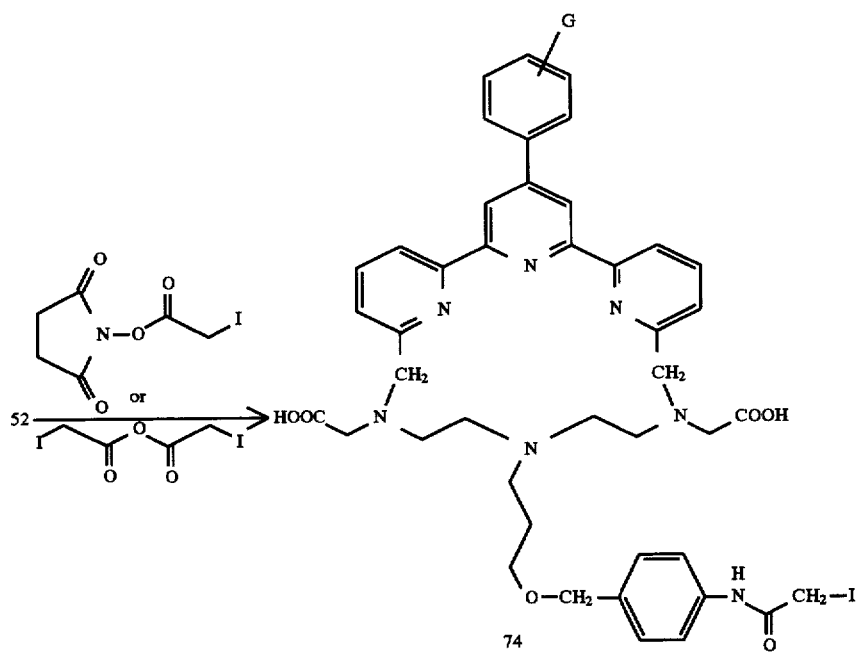

In subsequent reactions with proteins, the carboxylic acid groups of the iminoacetic acid moieties in the products of the above representative reaction schemes can be protonated or can be present as ionic species (represented, for example, as sodium salts). The extent of protonation and of deprotonation of any one species is a function of the pH of the reaction medium which contains both the protein reactive group-containing reagent and the protein. The use of buffer salts such as, for example, phosphate, borate, citrate and acetate buffers to control the pH of the reaction medium is a part of this aspect of the invention.

While the foregoing discussion of synthetic routes useful for the preparation of representative protein reactive groups has been focused on certain preferred terpyridine systems represented by structures (36a) and (42), it will be understood that these chemistries can be applied to the wider variety of compounds defined more generally by structure I as needed to carry out the purposes of this invention.

In one embodiment, this invention also provides metal complexes comprising the novel complexing agents of this invention as described above bound, i.e., chelated, to one or more metal ions. The term 'metal ion' as used herein is intended to include any ion of an element other than hydrogen that has an oxidation state equal to or greater than 1 and which can bind to a complexing agent of this invention through interaction with sites of high electron density in the complexing agent such as at heteroatom sites. The interaction of the metal ion with sites of high electron density in the complexing agent can be in the form of a Lewis acid-base interaction, wherein the oxidation state of metal ion is stabilized by interaction with donated electron density from sites of high electron density of the complexing agent. A metal ion can also interact with sites of high electron density in the complexing agent to form a salt in the form of an ionic association between a positively charged metal ion such as a lanthanide ion or a yttrium ion and a negatively charged substituent on the macrocyclic complexing agent such as a carboxylate anion substituent or a phosphonate anion substituent. A metal ion can also interact with sites of high electron density in the complexing agent to form a covalent bond between the metal which has an oxidation state equal to or greater than 1 such as rhenium or technitium and a heteroatom of the macrocyclic complexing agent such as a sulfur or nitrogen or oxygen atom.

It is frequently desirable that the metal ion be easily complexed to the chelating agent, for example, by merely exposing or mixing an aqueous solution of the chelating agent with a metal salt, preferably in an aqueous solution. Preferably such solution has a pH in the range of about 4 to about 11. The metal ion salt can be any composition containing the metal ion. Salts with a low water solubility are useful, but preferably the salt is a water soluble salt of the metal such as, for example, a halogen or nitrate salt. More preferably such salts are selected so as not to interfere with the binding of the metal ion with the chelating agent. The chelating agent is preferably in aqueous solution at a pH of between about 5 and about 9, more preferably between about 6 and about 8.

The chelating agent can be mixed with buffer salts such as citrate, acetate, phosphate and borate to produce the optimum pH. Preferably, said buffer salts are selected so as not to interfere with the subsequent binding of the metal ion to the chelating agent. A presently preferred buffer is sodium acetate plus acetic acid in water.

In addition to ions of alkali metals such as sodium, potassium, and cesium, and to ions of alkaline earth metals such as magnesium, calcium, and barium, preferred metal ions can be selected from, but are not limited to, ions of elements of groups IIA through VIA.

Preferred metals include those of atomic number 12, 13, 20, the transition elements 21 to 33, 38 to 52, 56, 72 to 84 and 88 and those of the lanthanide series (atomic number 57 to 71). Ions of yttrium and the lanthanides metals are especially preferred.

In another embodiment, the metal chelate of this invention can comprise a fluorescent metal ion. The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. $Eu^{+3}$ is especially preferred.

Metal complexes of this invention comprising a novel complexing agent of this invention as described above chelated to one or more fluorescent metal ions such as, for example, a $Eu^{+3}$ ion can exhibit utility in time delayed fluorescence and assays which involve time delayed fluorescence such as in the detection of fluorescent metal ions such as $Eu^{+3}$. In such an assay, a macrocyclic chelating agent of this invention is exposed to a material such as a solution that contains a fluorescent metal ion such as $Eu^{+3}$ ion for a sufficient amount of time so that a complex is formed between the chelating agent and the Eu ion. The complex is then irradiated with an excitation light such as, for example, a pulse of light having a maximum intensity at a wavelength of about 385 nanometers. The excitation light pulse is then stopped or blocked from further access to the metal complex, an effective time such as about 400 microseconds is allowed to elapse, and emission of light is then detected and measured with a detector capable of determining intensity of light as a function of wavelength. In particular, it is desirable that the wavelength of the emitted light be different from the wavelength of the excitation light, and that the effective time delay be about 400 microseconds or longer so that no interference from ambient fluorescent emitters interferes with the assay. A preferred composition for this type of assay comprises macrocycle (39a) chelated to a $Eu^{+3}$ ion.

In another embodiment, the metal of the metal chelate of this invention can comprise a paramagnetic metal ion which is suitable for use in nuclear magnetic resonance applications which include diagnostic imaging using MRI techniques. The paramagnetic element can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Mn, Gd, and Dy are especially preferred.

In another embodiment, the metal of the metal chelate of this invention can comprise a radionuclide. The radionuclide can be selected, for example, from radioisotopes of Sc, Fe, Pb, Ga, Y, Bi, Lu, Mn, Cu, Cr, Zn, Ge, Mo, Tc, Ru, In, Sn, Sm, Sr, Eu, Dy, Sb, W, Re, Po, Ta and Tl. Preferred radionuclides include $^{44}Sc$, $^{64}Cu$, $^{67}Cu$, $^{111}In$, $^{212}Pb$, $^{68}Ga$, $^{90}Y$, $^{87}Y$, $^{153}Sm$, $^{212}Bi$, $^{99m}Tc$, $^{186}Re$ and $^{188}Re$. Of these, especially preferred is $^{90}Y$.

In some applications, a metal chelate of a mixture of metal ions such as sodium ions and yttrium ions is useful. For example, a solution of a metal complexing (or chelating) agent of this invention such as compound (39a) in a sodium acetate buffer can be treated with a less than stoichiometric quantity of a radionuclide such as $^{90}Y$, and after a sufficient time during which chelation of substantially all of the radionuclide occurs, the subsequent mixture containing $^{90}Y$ bound to metal chelate plus the sodium salt of non-$^{90}Y$-containing metal chelate can be useful without further separation of the individual components, for example, in radioscintigraphic analysis of proteins separated by electrophoresis. In bulk solution, the metal chelate of this aspect of this invention preferably contains a ratio of metal radionuclide ion to chelating agent that is effective in such applications. In preferred embodiments, the mole ratio of metal ion per chelating agent is from about 1:1000 to about 1:1.

In another embodiment, this invention provides a targeting immunoreagent comprising a metal ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

The targeting immunoreagent of this invention includes an immunoreactive group bonded, by a linking group that comprises the residue of a protein reactive group, to the macrocyclic complexing agent. The targeting immunoreagent thus comprises a conjugate of a complexing agent having the structure I above and the immunoreactive group. The complexing agent and the metal can be complexed either before or after the complexing agent is attached to the immunoreactive group.

As used herein the term "immunoreactive group" is meant to include any organic compound which is capable of bonding, covalently or non-covalently, to a chelating agent of this invention and which is found in a living organism or is useful in the diagnosis, treatment or genetic engineering of cellular material or living organisms, and which has a capacity for interaction with another component which may be found in biological fluids or associated with cells to be treated, such as tumor cells. Immunoreactive groups for use in the practice of this invention are those which have a receptor molecule specific to a ligand of interest. Thus, a specific binding reaction involving the reagent can be used for the desired targeting. Examples of such ligand-receptor complexes include, but are not limited to antibody-antigen, avidin-biotin, repressor (inducer)—promoter of operons and sugar-lectin complexes. Additionally, complementary nucleic acids, i.e., a hybridized product of complementary strands, are also considered specific binding materials as the term is used herein.

The immunoreactive group can be selected from a wide variety of naturally occurring or synthetically prepared materials, including, but not limited to enzymes, amino acids, peptides, polypeptides, proteins, lipoproteins, glycoproteins, lipids, phospholipids, hormones, growth factors, steroids, vitamins, polysaccarides, viruses, protozoa, fungi, parasites, rickettsia, molds, and components thereof, blood components, tissue and organ components, pharmaceuticals, haptens, lectins, toxins, nucleic acids (including oligonucleotides), antibodies (monoclonal and polyclonal), anti-antibodies, antibody fragments, antigenic materials (including proteins and carbohydrates), avidin and derivatives thereof, biotin and derivatives thereof, and others known to one skilled in the art. In addition, an immunoreactive group can be any substance which, when presented to an immunocompetent host, will result in the production of a specific antibody capable of binding with that substance, or the antibody so produced, which participates in an antigen-antibody reaction. Preferred immunoreactive groups are antibodies and various immunoreactive fragments thereof (i.e., antibody fragments) as long as they contain at least one reactive site for reaction with the protein reactive group of the chelating agent of Structure I. That site can be inherent to the immunoreactive species or it can be introduced through appropriate chemical modification of the immunoreactive species.

As used herein, the term "antibody fragment" refers to an immunoreactive material which comprises a residue of a whole antibody, which antibody characteristically exhibits an affinity for binding to an antigen. The term "affinity," as used herein, refers to the thermodynamic expression of the strength of interaction or binding between an antibody combining site (or other ligand) and an antigenic determinant (or receptor) and, thus, of the stereochemical compatibility between them. As such, it is the expression of the equilibrium or association constant for an antibody-antigen (or a ligand-receptor) interaction.

Antibody fragments exhibit at least a percentage of the affinity of the whole antibody for binding to the target antigen, the percentage being in the range of 0.001 percent to 1,000 percent, preferably 0.01 percent to 1,000 percent, more preferably 0.1 percent to 1,000 percent, and most preferably 1.0 percent to 1,000 percent, of the relative affinity of the whole antibody for binding to the antigen.

An antibody fragment can be produced from an antibody by a chemical reaction comprising one or more chemical bond cleaving reactions; by a chemical reaction comprising one or more chemical bond forming reactions employing as reactants one or more chemical components selected from the group consisting of amino acids, peptides, carbohydrates, linking groups as defined herein, spacing groups as defined herein, protein reactive groups as defined herein, and antibody fragments such as are produced as decribed herein; and by a molecular biological process, a bacterial process, or by a process comprising genetic engineering of antibody genes.

An antibody fragment can be derived by one or more of the following:

(a) by cleavage of one or more chemical bonds comprising an antibody, said bonds being selected from, for example, carbon-nitrogen bonds, sulfur-sulfur bonds, carbon-carbon bonds, carbon-sulfur bonds, and carbon-oxygen bonds, and wherein the method of said cleavage is selected from:

(i) a catalysed chemical reaction comprising the action of a biochemical catalyst such as an enzyme, for example, papain or pepsin which to those skilled in the art are known to produce antibody fragments commonly referred to as Fab and Fab'2, respectively;

(ii) a catalysed chemical reaction comprising the action of an electrophilic chemical catalyst such as a hydronium ion which, for example, favorably occurs at a pH equal to or less than 7;

(iii) a catalysed chemical reaction comprising the action of a nucleophilic catalyst such as a hydroxide ion which, for example, favorably occurs at a pH equal to or greater than 7; and (iv) a chemical reaction comprising a substitution reaction employing a reagent which is consumed in a stoichiometric manner such as a substitution reaction at a sulfur atom of a disulfide bond by a reagent comprising a sulfhydryl group;

(v) a chemical reaction comprising a reduction reaction such as the reduction of a disulfide bond; and (vi) a chemical reaction comprising an oxidation reaction such as the oxidation of a carbon-oxygen bond of a hydroxyl group or the oxidation of a carbon-carbon bond of a vicinal diol group such as occurs in a carbohydrate moiety by the action of sodium periodate; or (b) by formation of one or more chemical bonds between one or more reactants, such as formation of one or more covalent bonds selected from, for example, carbon-nitrogen bonds (such as, for example, amide bonds, amine bonds, hydrazone bonds, and thiourea bonds), sulfur-sulfur bonds such as disulfide bonds, carbon-carbon bonds, carbon-sulfur bonds, and carbon-oxygen bonds, and employing as reactants in said chemical bond formation one or more reagents comprising amino acids, peptides, carbohydrates, linking groups as defined herein, spacing groups as defined herein, protein reactive groups as defined herein, and antibody fragments such as are produced as described in (a), above; or, (c) by formation of one or more non-covalent bonds between one or more reactants. Such non-covalent bonds comprise hydrophobic interactions such as occur in an aqueous medium between chemical species that independently comprise mutually accessible regions of low polarity such as regions comprising aliphatic and carbocyclic groups, and of hydrogen bond interactions such as occur in the binding of an oligonucletide with a complementary oligonucletide; or (d) by the methods of molecular biology or by genetic engineering of antibody genes, for example, in the genetic engineering of a single chain immunoreactive group or an Fv fragment.

An antibody fragment can be produced as a result of a combination of one or more of the above methods.

In certain embodiments, the immunoreactive group can be an enzyme which has a reactive group for attachment to the chelating agent as a result of reaction with the protein reactive group thereof. Representative enzymes include, but are not limited to, aspartate, aminotransaminase, alanine aminotransaminase, lactate dehydrogenase, creatine phosphokinase, gamma glutamyl transferase, alkaline acid phosphatase, prostatic acid phosphatase, horseradish peroxidase and various esterases.

If desired, the immunoreactive group can be modified or chemically altered to provide reactive groups for attaching to the chelating agent by techniques known to those skilled in the art. Such techniques include the use of linking moieties and chemical modification such as described in WO-A-89/02931 and WO-A-89/2932, which are directed to modification of oligonucleotides, and U.S. Pat. No. 4,719, 182.

Two highly preferred uses for the targeting immunoreagent compositions of this invention are for the diagnostic imaging of tumors and the radiological treatment of tumors. Preferred immunological groups therefore include antibodies (sometimes hereinafter referred to as Ab) to tumor-associated antigens. Specific non-limiting examples include B72.3 and related antibodies (described in U.S. Pat. Nos. 4,522,918 and 4,612,282) which recognize colorectal tumors, 9.2.27 and related anti-melanoma antibodies, D612 and related antibodies which recognize colorectal tumors, UJ13A and related antibodies which recognize small cell lung carcinomas, NRLU-10 and related antibodies which recognize small cell lung carcinomas and colorectal tumors (Pan-carcinoma), 7E11C5 and related antibodies which recognize prostate tumors, CC49 and related antibodies which recognize colorectal tumors, TNT and related antibodies which recognize necrotic tissue, PR1A3 and related antibodies which recognize colon carcinoma, ING-1 and related antibodies, which are described in International Patent Publication WO-A-90/02569, B174, C174 and related antibodies which recognize squamous cell carcinomas, B43 and related antibodies which are reactive with certain lymphomas and leukemias, and anti-HLB and related monoclonal antibodies. A presently especially preferred antibody is ING-1.

Such antibodies and other useful immunological groups described above are large, complex molecules having multiple sites for appendage of the complexing agent. Consequently, the immunoreactive group can have appended to it additional complexing agents via one of the protein reactive groups. Thus, the term immunoreactive group is intended to include immunological groups having complexing agent molecules bonded thereto through one or more protein reactive groups.

The immunoreactive material contains a reactive site that comprises a reactive group that can react or combine with the protein reactive group on the chelating agent as defined in Structure 1 to form a linking group between the immunoreactive material and the chelating agent. Suitable reactive sites on the immunoreactive material include amine sites of lysine; terminal peptide amines; carboxylic acid sites, such as are available in aspartic acid and glutamic acid residues; sulfhydryl sites, such as in cysteine residues; carbohydrate sites and oxidized carbohydrate sites; activated carbon-hydrogen and carbon-carbon bonds which can react through insertion via free radical reaction or nitrene or carbene reaction of an activated residue; sites of oxidation including, for example, a vicinal diol site of a carbohydrate moiety and a serine alcohol, each of which can be oxidized to an aldehyde; sites of reduction, for example a disulfide linkage which can be reduced to form a sulfhydryl group; aromatic sites such as the hydroxyaromatic group of tyrosine; and hydroxyl sites such as the phenolic hydroxyl group of tyrosine, the hydroxyl group of serine, and the hydroxyl group of a carbohydrate moiety.

In one aspect, the phrase "residue of a linking group" as used herein refers to a moiety that remains, results, or is derived from the reaction of a protein reactive group with a reactive site on a protein. The phrase "protein reactive group" as used herein refers to any group which can react with functional groups typically found on proteins. However, it is specifically contemplated that such protein reactive groups can also react with functional groups typically found on relevant nonprotein molecules.

Preferred linking groups are derived from protein reactive groups selected from but not limited to:

(1) a group that will react directly with amine, alcohol, or sulfhydryl groups on the immunoreactive protein or biological molecule containing the reactive group, for example, active halogen containing groups including, for example, chloromethylphenyl groups and chloroacetyl [ClCH$_2$C(=O)—] groups, activated 2-(leaving group substituted)-ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents;

(2) a group that can react readily with modified proteins or biological molecules containing the immunoreactive group, i.e., proteins or biological molecules containing the immunoreactive group modified to contain reactive groups such as those mentioned in (1) above, for example, by oxidation of the protein to an aldehyde or a carboxylic acid, in which case the "linking group" can be derived from protein reactive groups selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl, the alkyl portions of which linking groups contain from 1 to about 20 carbon atoms and the aryl portions of which linking groups contain from about 6 to about 20 carbon atoms; and (3) a group that can be linked to the protein or biological molecule containing the immunoreactive group, or to the modified protein as noted in (1) and (2) above by use of a crosslinking agent. The residues of certain useful crosslinking agents, such as, for example, homobifunctional and heterobifunctional gelatin hardeners, bisepoxides, and bisisocyanates can become a part of a linking group during the crosslinking reaction. Other useful crosslinking agents, however, can facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the ethers of U.S. Pat. No. 4,877,724. With these crosslinking agents, one of the reactants such as the immunoreactive group must have a carboxyl group and the other, such as the complexing agent, must have a reactive amine, alcohol, or sulfhydryl group. In amide bond formation, the crosslinking agent first reacts selectively with the carboxyl group, then is split out during reaction of the thus "activated" carboxyl group with an amine to form an amide linkage between the immunoreactive group and the chelating agent and thus covalently bonding the two moieties. An advantage of this approach is that crosslinking of like molecules is avoided, whereas the reaction of, for example, homo-bifunctional crosslinking agents is nonselective and unwanted crosslinked molecules are obtained.

Useful linking groups are derived from various heterobifunctional cross-linking reagents such as those listed in the Pierce Chemical Company Immunotechnology Catalog—Protein Modification Section, (1991 and 1992). Useful non-limiting examples of such reagents include: Sulfo-SMCC, i.e., Sulfosuccinimidyl 4-(N-maleimidomethyl) cyclohexane-1-carboxylate; Sulfo-SIAB, i.e., Sulfosuccinimidyl (4-iodoacetyl)aminobenzoate; Sulfo-SMPB, i.e., Sulfosuccinimidyl 4-(p-maleimidophenyl)butyrate; 2-IT, i.e., 2-Iminothiolane; and SATA, i.e., N-Succinimidyl S-acetylthioacetate.

In addition to those described above, the linking groups, in whole or in part, can also be comprised of and derived from complementary sequences of nucleotides and residues of nucleotides, both naturally occurring and modified, preferably non-self-associating oligonucleotide sequences. Particularly useful, non-limiting examples of reagents for incorporation of modified nucleotide moieties containing reactive functional groups, such as amine and sulfhydryl groups, into an oligonucleotide sequence are commercially available from, for example, Clontech Laboratories Inc. (Palo Alto Calif.) and include Uni-Link AminoModifier (Catalog #5190), Biotin-ON phosphoramidite (Catalog #5191), N-MNT-C6-AminoModifier (Catalog #5202), AminoModifier II (Catalog #5203), DMT-C6-3'Amine-ON (Catalog #5222), C6-ThiolModifier (Catalog #5211), and the like.

In one aspect, linking groups of this invention are derived from the reaction of a reactive functional group such as an amine or sulfhydryl group as are available in the above Clontech reagents, one or more of which has been incorporated into an oligonucleotide sequence, with, for example, one or more of the previously described protein reactive groups such as heterobifunctional protein reactive groups, one or more of which has been incorporated into, for example, an immunoreactive material as described above.

Respectively complementary individual oligonucleotide sequences are attached to the two components of the conjugate, one sequence to the immunoreactive material and the complementary oligonucleotide sequence to the chelating agent. The hybrid formed between the two complementary oligonucleotide sequences then comprises the linking group between the immunoreactive material and the chelating agent.

If desired, two or more copies of the same oligonucleotide sequence can be linked, for example, in tandem to one immunoreactive material, and a complementary oligonucleotide sequence comprised of multiple chelating agents can be added. The multiple hybrids formed between the two complementary oligonucleotide sequences then comprises the linking group between the immunoreactive group and multiple chelating agents.

An antibody or fragment thereof containing a carbohydrate region can be attached to the complexing agent through the carbohydrate region of the antibody, such as described in U.S. Pat. No. 4,937,183, the disclosure of which is hereby incorporated herein by reference in its entirety. Useful methods for attaching an antibody are also described in U.S. Pat. Nos. 4,671,958; 4,699,784; 4,741,900; and 4,867,973. The term "protein reactive group" as defined herein is intended to include such linkages.

Preferred linking groups also include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups; carbonyl; sulfonyl; sulfinyl; ether; thioether; ester, i.e., carbonyloxy and oxycarbonyl; thioester, i.e., carbonylthio, thiocarbonyl, thiocarbonyloxy, and oxythiocarboxy; amide, i.e., iminocarbonyl and carbonylimino; thioamide, i.e., iminothiocarbonyl and thiocarbonylimino; thio; dithio; phosphate; phosphonate; urelene; thiourelene; urethane, i.e., iminocarbonyloxy,and oxycarbonylimino; an amino acid linkage, i.e., a

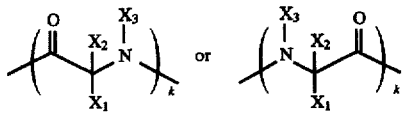

group wherein k=1 and $X_1$, $X_2$, $X_3$ are independently selected from H; alkyl, containing from 1 to 18, preferably 1 to 6 carbon atoms, such as methyl, ethyl and propyl, such alkyl optionally being interrupted by 1 or more heteroatoms such as oxygen, nitrogen and sulfur; substituted or unsubstituted aryl, containing from 6 to 18, preferably 6 to 10 carbon atoms such as phenyl, hydroxyiodophenyl, hydroxyphenyl, fluorophenyl and naphthyl; aralkyl, preferably containing from 7 to 12 carbon atoms, such as benzyl; heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are as described above; or a peptide linkage, i.e., a

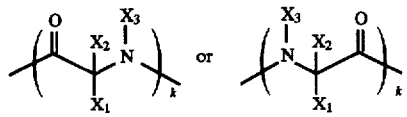

group wherein k>1 and each X independently represents a group as described for $X_1$, $X_2$, $X_3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry as described above. Especially preferred linking groups include amino groups which, when linked to the residue of a chelating agent via an isothiocyanate group on the chelating agent, form thiourea groups.

The linking groups can contain various substituents which do not interfere with the coupling reaction between the chelating agent of this invention and the immunoreactive group. The linking groups can also contain substituents which can otherwise interfere with such reaction, but which during the coupling reaction, are prevented from so doing with suitable protecting groups commonly known in the art and which substituents are regenerated after the coupling reaction by suitable deprotection. The linking groups can also contain substituents that are introduced after the coupling reaction. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms, such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; or a carboxyalkyl group, the alkyl portion of which preferably contains from 1 to 8 carbon atoms.

The products of the reaction of any of these protein reactive group containing chelating agents with immunoreactive materials, preferably with proteins, can be purified by conventional techniques such as diafiltration, HPLC, electrophoresis, and the like. The immunoreactive materials may be subsequently modified with agents such as PEG (polyethylene glycol) reagents as is well known in the art to impart reduced immunogenicity to the modified proteins.

Techniques for performing the covalent binding of the immunoreactive group to the metal complexing agents are known in the art and include simply mixing the materials together, preferably in aqueous solution in the presence of a buffer salt such as sodium borate or sodium phophate, or sodium acetate at a pH of about 4 to about 11, preferably from about 7 to about 10.

The ratio of the complexing agent to the immunoreactive group can vary widely from about 0.5:1 to 10:1 or more. In some embodiments, the mole ratio of complexing agent to immunoreactive groups is from about 1:1 to about 6:1. In some uses of the immunoconjugates of this invention, the bulk ratio of the chelating agent to the immunoreactive group can be an apparent fraction because the immunoconjugate can be used in the presence of unmodified immunoreactive material. For example, a mixture of an unmodified antibody such as ING-1 together with an immunoconjugate comprising a residue of ING-1, a residue of compound 39a, and a radionuclide ion can be useful in an application such as the radioscintigraphic analysis of a tumor in a patient. As such, the bulk ratio of chelating agent to ING-1 in such a mixture can be from about 0.01 to about 6, preferably from about 0.1 to about 3.

The immunoreagents of this invention comprise a metal ion, a complexing agent as described in Structure I above, and an immunoreactive group as described above attached by a linking group to the complexing agent, which linking group comprises the residue of a protein reactive group on the complexing agent. The immunoreagents of this invention can contain a wide range of ratios of metal ion to complexing agent. In preferred embodiments, the mole ratio of metal ion to complexing agent is from about 1:1000 to about 1:1. The ratio of the complexing agent to the immunoreactive group can vary widely from about 0.5:1 to 10:1 or more. In some embodiments, the mole ratio of complexing agent to immunoreactive groups is from about 1:1 to about 6:1.

In another embodiment, this invention provides a targeting radioactive immunoreagent comprising a metal radionuclide ion, a complexing agent, and an immunoreactive group attached through a linking group to said complexing agent, wherein the complexing agent has the structure I as defined above, the immunoreactive group is as described above, and the linking group between the complexing agent and the immunoreactive group comprises the residue of the protein reactive group on the complexing agent as described above. The radionuclide ion can be selected, for example, from Sc, Fe, Pb, Ga, Y, Bi, Mn, Cu, Cr, Zn, Ge, Mo, Tc, Ru, In, Sn, Re, Sr, Sm, Lu, Eu, Dy, Sb, W, Po, Ta and Tl ions. Preferred radionuclides include $^{44}Sc^{+++}$, $^{64}Cu^{++}$, $^{67}Cu^{++}$, $^{111}In^{+++}$, $^{212}Pb^{++}$, $^{68}Ga^{++}$, $^{90}Y^{+++}$, $^{177}Lu^{++}$, $^{186}Re^{++}$, $^{188}Re^{++}$, $^{99}mTc^{++}$, $^{87}Y^{+++}$, and $^{212}Bi^{+++}$ ions. Of these, the most preferred are $^{90}Y^{+++}$ ions.

The metal radionuclide ion and the complexing agent of the targeting immunoreagent are easily complexed by merely mixing an aqueous solution of the immunoreagent containing the complexing agent with a metal radionuclide salt in an aqueous solution preferably having a pH of 4 to 11. The salt can be any water soluble salt of the metal such as a halogen salt. The chelate comprising the immunoreagent containing the complexing agent and the metal ion is generally prepared in aqueous solution at a pH of between about 5 and about 10 and preferably from about 6 to about 9. The complex optionally is formed in the presence of buffers, such as acetate, phosphate and borate, to produce the optimum pH. Preferably, the buffer salts are selected so as not to interfere with the subsequent binding of the metal ion to the chelating agent. A presently preferred buffer is acetate.

The targeting immunoreagent of this invention comprising a radioisotope of a metal ion such as $^{90}Y^{+3}$ (as a non-limiting example) can be used for the therapeutic treatment of tumors, particularly if the immunoreagent is a tumor antigen specific antibody or a fragment of such antibody. In therapeutic applications, the targeting immunoreagent of this invention preferably contains a ratio of metal radionuclide ion to chelating agent that is effective in such therapeutic applications. In preferred embodiments, the mole ratio of metal ion per chelating agent is from about 1:100 to about 1:1.

The targeting immunoreagent of this invention comprising a radioisotope of a metal ion such as $^{111}In^{+3}$ or $^{187}Y^{+3}$ (as non-limiting examples) can be used for the diagnostic imaging of tumors in cancer patients, particularly if the immunoreagent is a tumor antigen specific antibody or a fragment of such antibody. In diagnostic imaging, applications, the targeting immunoreagent of this invention preferably contains a ratio of metal radionuclide ion to chelating agent that is effective in such diagnostic imaging applications. In preferred embodiments, the mole ratio of metal ion per chelating agent is from about 1:10,000 to about 1:1.

In another embodiment, this invention provides a targeting paramagnetic immunoreagent comprising a paramagnetic metal ion as described above, the residue of a complexing agent, and an immunoreactive group as described above attached through a linking group to said complexing agent, wherein the complexing agent has the structure I as defined above and the linking group between the complexing agent and the immunoreactive group comprises the residue of the protein reactive group on the complexing agent as described above.

In another embodiment, this invention provides a targeting fluorescent immunoreagent comprising a flourescent metal ion as described above, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

This invention also provides therapeutic and diagnostic compositions comprising the above-described targeting radioactive immunoreagents.

This invention also provides diagnostic compositions comprising the above-described targeting paramagnetic immunoreagents.

This invention also provides diagnostic compositions comprising the above-described targeting fluorescent immunoreagents.

This invention further provides a method for diagnostic imaging a site in a patient comprising a) administering to the patient an effective amount of the above-described radioactive immunoreagent capable of targeting the site, and b) imagewise activating a radiation-sensitive element or device, such as, for example, a film or electronic sensor, with the radiation emitted from the targeted site.

This invention further provides a method for diagnostic imaging a site in a patient or a site in a specimen from the patient comprising a) administering to the patient or to a site in a specimen from the patient an effective amount of the above-described paramagnetic immunoreagent capable of targeting the site in a pharmaceutically acceptable carrier therefor, and b) imagewise activating a nuclear magnetic resonance detection sensor element or device which is sensitive to a change in one or more nuclear magnetic relaxation properties of an isotope such as a proton at the site of the patient or at the site in a specimen from the patient while said site is exposed to a controlled magnetic field environment such as, for example, a magnetic field in a magnetic resonance imaging instrument, which change is induced by the paramagnetic metal ion of the immunoreagent.

This invention further provides a method for treating a disease site in a patient or a disease site in a specimen from the patient comprising administering to the patient or to a specimen from the patient an effective amount of a therapeutic composition comprising the above-described radioactive immunoreagent capable of targeting the site and a pharmaceutically acceptable carrier therefor.

This invention further provides a method for diagnostic imaging a site in a specimen from a patient comprising a) administering to the specimen an effective amount of a fluorescent composition comprising the above-described fluorescent immunoreagent capable of targeting a site in the specimen, b) irradiating the specimen with light which is absorbed by the metal complex of the immunoreagent, and c) imagewise activating a fluorescence emission sensor element or device, such as, for example, a film or electronic sensor, with the fluorescent light emitted from the targeted site. A preferred method uses time delayed fluorescence detection.

In another embodiment, the targeting immunoreagent of this invention can comprise a fluorescent metal ion.

The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. Eu is especially preferred.

In another embodiment, the targeting immunoreagent of this invention can comprise one or more paramagnetic elements which are suitable for the use in MRI applications.

The paramagnetic element can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Mn, Gd, and Dy are especially preferred.

In another embodiment of this invention, a targeting immunoreagent as described above comprising at least two metal ions in combination with one another in the same formulation is specifically contemplated. For example, the use of a therapeutically effective dose of a radionuclide such as $^{90}Y^{+3}$ together with a diagnostic imaging effective dose of a paramagnetic ion such as $Gd^{+3}$, the ratio of the molar concentration of the diagnostic imaging effective ion to the molar concentration of the radionuclide ion being typically greater than one, in a pharmaceutically effective formulation of said targeting immunoreagent, permits the simultaneous magnetic resonance imaging of at least a portion of the tissue of a host patient during therapeutic treatment of said patient.

In another embodiment of this invention, the use of radioisotopes of iodine is specifically contemplated. For example, if the targeting immunoreagent comprises a substituent that can be chemically substituted by iodine in a covalent bond forming reaction, such as, for example, a substituent containing hydroxyphenyl functionality, such a substituent can be labeled by methods well known in the art with a radioisotope of iodine. The thus covalently linked radioactive iodine species can be used in therapeutic and diagnostic imaging applications as described herein.

In a preferred embodiment, an effective dose of a targeting radioactive immunoreagent as described above in a pharmaceutically acceptable medium is prepared by exposing a composition comprising a residue of an immunoreactive group as described above and a residue of a chelating agent having Structure I as described above linked to the immunoreactive group by a linking group as described above to a composition containing a radioactive metal ion as described above such that the molar amount of said radioactive metal ion is less than the molar amount of the chelating group comprising the targeting immunoreagent in said composition, the duration of the exposure lasting an effective time to permit uptake of said radioactive metal ion into said targeting immunoreagent.

In a preferred embodiment, an effective dose of a targeting immunoreagent as described above in a pharmaceutically acceptable medium is administered to a patient and said targeting immunoreagent is allowed to accumulate at the target site such as at a tumor site in said patient.

In a preferred embodiment, a therapeutically effective dose of a targeting radioactive immunoreagent as described above in a pharmaceutically acceptable medium is administered to a patient or to a tissue from a patient and said targeting radioactive immunoreagent is allowed to accumulate at the target site such as at a tumor site in said patient.

The present invention also comprises one or more targeting radioactive immunoreagents as described above formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The present invention also comprises one or more targeting paramagnetic immunoreagents as described above formulated into compositions together with one or more non-toxic physiologically acceptable carriers, adjuvants or vehicles which are collectively referred to herein as carriers, for parenteral injection, for oral administration in solid or liquid form, for rectal, or topical administration, or the like.

The compositions can be administered to humans and animals either orally, rectally, parenterally (intravenously, by intramuscularly or subcutaneously), intracisternally, intravaginally, intraperitoneally, intravesically, locally (powders, ointments or drops), or as a buccal or nasal spray. It is specifically contemplated that a targeting paramagnetic immunoreagent as described above and targeting radioactive immunoreagent as described above can be administered by the same route. It is also contemplated that a paramagnetic immunoreagent as described above can be administered by a route different from that of a targeting radioactive immunoreagent as described above.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary, pharmaceutically acceptable, excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated as being within the scope of this invention.

Actual dosage levels of active ingredients in the compositions of the present invention may be varied so as to obtain an amount of active ingredient that is effective for imaging or to obtain a desired therapeutic response for a particular composition and method of administration. The selected dosage level therefore depends upon the desired imaging or therapeutic effect, on the route of administration, on the desired duration of treatment and other factors.

The total daily dose of the compounds of this invention administered to a host in single or divided dose may be in amounts, for example, of from about 1 nanomol to about 5 micromols per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

In another embodiment, the present invention is directed to a method of diagnosis comprising the administration of a diagnostic imaging effective amount of the compositions of the present invention as described above to a mammal or to a tissue from said mammal in need of such diagnosis. A method for diagnostic imaging for use in medical procedures in accordance with this invention comprises administering to the body of a test subject in need of a diagnostic image an effective diagnostic image producing amount of the above-described compositions. In this method, an effective diagnostic image producing amount of a radioactive targeting immunoreagent as described above in a pharmaceutically acceptable medium is administered to a patient and said radioactive targeting immunoreagent is allowed to accumulate at the target site such as at a tumor site in said patient. The image pattern can then be visualized, for example, by radioscintigraphy.

Alternatively, a patient or a specimen of a tissue of interest from a patient may be treated with a diagnostic imaging effective amount, i.e., a diagnostic imaging effective dose, of a targeting immunoreagent of this invention comprising a radionuclide as described above. This may be done by administering said dose to the environs of said tissue of interest of said patient or said specimen undergoing such diagnostic imaging, waiting for an effective period of time during which said immunoreagent will bind to sites on cells of said tissue of interest and during which time unbound immunoreagent will be removed from the environs of said tissue by circulation of a fluid such as blood in a patient or such as buffered saline solution in a sample of a tissue from a patient, and then obtaining an image as a function of time of all or part of said tissue of interest. When the image of all or part of said tissue of interest is optimal, a second dose comprising a therapeutically effective amount of targeting radioactive immunoreagent containing the same or a different radionuclide as that employed in the first dose of targeting radioactive immunoreagent is administered to said patient or to said tissue of interest of said patient.

In addition to human patients, the test subjects can include mammalian species such as rabbits, dogs, cats, monkeys, sheep, pigs, horses, bovine animals and the like.

After administration of a composition of the present invention, the subject mammal is maintained for a time period sufficient for the administered composition to be distributed throughout the subject and enter the tissues of the mammal. A sufficient time period is generally from about 1 hour to about 2 weeks or more and, preferably from about 2 hours to about 1 week.

The following examples further illustrate the invention and are not to be construed as limiting of the specification and claims in any way. Specific embodiments of the invention are illustrated in the following examples.

EXAMPLE 1

2-Acetyl-6-bromopyridine, 2

2-Acetyl-6-bromopyridine was synthesized by the method of J. E. Parks, B. E. Wagner, and R. E. Holm, *J. Organometal. Chem* 56, 53–66 (1973) from 2,6-bromopyridine, 1. A 5 L 3-neck flask was charged with 2,6-dibromopyridine (181 g; 0.75 mole) and 2.0 L ether. The suspension was stirred under nitrogen at −60° C. and then n-butyllithium (300 mL; 2.5M) in hexane was added from a pressure equalizing dropping funnel over 20 minutes. The bath was lowered and the near solution was allowed to warm to −50° C. After 15 minutes, the dark yellow solution was re-cooled to −78° C. in a dry ice/ether bath and dimethylacetamide (70 g; 0.86 mole) in 70 mL ether was added at such a rate that the temperature did not exceed −75° C. The addition took about one hour for completion, after which the bath was removed to allow the reaction to warm to −60° C. A solution of ammonium chloride (50 g; 0.93 mole) in 150 mL of H₂O was added dropwise over 10 minutes under nitrogen and the temperature rose to −40° C. The mixture was stirred for 45 minutes and the layers were separated. The aqueous layer was back-extracted with 500 mL ether and the pooled organic layers were washed twice with $H_2O$ and once with saturated salt solution. The organic layer was dried over $MgSO_4$ and, after evaporating to dryness, gave 150 g of yellow oil. This material, after pooling with another run of the same scale, was subjected to Kugelrohr distillation at 80° C./0.1 mm Hg to give 257 g (86%) of a product as a nearly colorless oil that crystallized readily on cooling. The compound exhibited a single spot in a silica gel thin layer chromatography (TLC) analytical system using 90% hexane: 10% ether (vol/vol).

EXAMPLE 2

1-[2-(6-Bromo-2-pyridinyl)-2-oxoethyl]pyridinium iodide, 4a

To a stirred solution of 2-acetyl-6-bromopyridine from example 1 (100 g; 0.5 mole) in 600 mL pyridine was added iodine (127 g; 0.5 mole). The mixture was heated on a steam bath for 45 minutes, and the product crystallized on cooling. The solid was filtered and the light yellow crystalline cake was rinsed twice with methylene chloride. After drying, 183 g of product (90% yield) was obtained. Melting point: 176°–178° C. The product was homogeneous in a silica gel TLC system using 95% acetone: 5% isopropanol (v/v).

EXAMPLE 3

1-[2-(6-Bromo-2-pyridinyl)-2-oxoethyl]pyridinium bromide, 4b

2-Acetyl-6-bromopyridine from example 1 (20.0 g, 100 mmol) was treated with bromine (6.2 mL, 0.12 mol) at reflux in 200 mL of $CHCl_3$ for 45 min. The solution was cooled to room temperature then washed with dilute aqueous $NaHCO_3/Na_2S_2O_3$. The organic phase was dried over $Na_2SO_4$, filtered, and evaporated to give an oil. The oil was dissolved in 200 mL of tetrahydrofuran (THF) and 30 mL of pyridine was added. The resulting solution was refluxed for 30 min. The mixture was cooled and filtered to give 26.1 g of off-white powder (73% yield); mp 256° C. (decomposition; discolors at 245° C.). The nuclear magnetic resonance (NMR) and infrared (IR) spectra were consistent with the assigned structure and the product was homogeneous by TLC.

Analysis for $C_{12}H_{10}Br_2N_2O$: Calculated: C, 40.26; H, 2.82; N, 7.82. Found: C, 40.12; H, 2.85; N, 7.79.

EXAMPLE 4

1-[2-(6-Bromopyridyl)]-3-(4-methoxyphenyl)-2-propenone, (Chalcone 5a)

To a stirred solution of 2-acetyl-6-bromopyridine from example 1 (50 g; 0.25 mole) in 450 mL methanol was added 4-anisaldehyde (48 g; 0.35 mole). The mixture was cooled in a water bath to 20° C. and then a solution of KOH (18 g; 0.28 mole) in 100 mL $H_2O$ was added rapidly. After about 30 seconds, the product began to crystallize and the temperature rose to 35° C. The light yellow mixture was stirred for 30 minutes and then filtered. The cake was rinsed twice with isopropanol, and after drying, gave 68 g (86% yield) of product. M.p.: 106.1°–106.5° C.; silica gel TLC using 90 hexane:10 ethyl acetate (v/v) gave a single spot.

EXAMPLE 5

1-(2-Bromopyridyl)-3-(4-methoxyphenyl)-2-propenone, 5a

Potassium hydroxide (18.2 g, 325 mmol) was dissolved in 100 mL of $H_2O$, and 100 mL of methanol was added. 2-Acetyl-6-bromopyridine from example 1 (65 g, 325 mmol) and (68 g, 650 mmol) of p-anisaldehyde were dissolved together in 400 mL of methanol, and the solution was poured into the KOH solution. Precipitation of product began within a few minutes, and the reaction was allowed to stand at room temperature overnight. The precipitate was collected, washed with isopropanol, and dried to yield 79 g (76%) of the product as a yellow solid, which exhibited a melting temperature of 100°–102° C. Mass spectrum (FDMS): 317 M+ (m/e). An aliquot was purified by column chromatography on Woelm Silica gel eluting with 100% dichloromethane. The NMR and IR spectra were consistent with the assigned structure and the product was homogeneous by TLC.

Anal. for $C_{15}H_{12}BrNO_2$: Calcd: C, 56.63; H, 3.80; N, 4.40. Found: C, 56.66; H, 3.87; N, 4.41.

EXAMPLE 6

6,6"-Dibromo-4'-(4-methoxyphenyl)-2,2':6',2"-terpyridine, 6a

A mixture of the chalcone product of example 4 (64 g; 0.20 mole), the pyridinium iodide product of example 2 (81 g; 0.20 mole) and ammonium acetate (77 g; 1.0 mole) in 600 mL acetic acid was heated at 95° C. for 3 hours and then overnight at 60° C. The reaction mixture was cooled to 15° C. and the crystalline cake was rinsed with $H_2O$ three times. After drying overnight 76.5 g (83%) pale yellow crystalline product was obtained. Mp: 205° C.; silica gel TLC system: 90 hexane:10 ethyl acetate; $H_2O$ determination :(Karl Fisher) found 0.02% $H_2O$.

EXAMPLE 7

6,6"-Dibromo-4'-(4-methoxyphenyl)-2,2':6',2"-terpyridine, 6a

The pyridinium bromide of example 3 (11.3 g, 31.6 mmol) and the chalcone of example 5 (10.0 g, 31.4 mmol) were refluxed in 100 mL of AcOH with 10 g of $NH_4OAc$ for 16 hours. The solution was cooled and filtered, and the solid was washed with AcOH then EtOH to give 13.48 g of white crystals (86%). Mp: 203°–204.5° C.; FDMS: M⁺=495 (m/e). The NMR and IR spectra were consistent with the assigned structure, and the product was homogeneous by thin layer chromatography.

Anal. Calc'd for $C_{22}H_{15}Br_2N_3O$: C, 53.1; H, 3.0; N, 8.5. Found: C, 52.9; H, 3.1; N, 8.4.

EXAMPLE 8

4'-(4-methoxyphenyl)-2,2':6'2"-terpyridine-6,6"-dicarboxaldehyde, 7a

A 3 L flask was charged with 400 mL THF and, while stirring under nitrogen, was cooled in a dry ice/ether bath to −78° C. A solution of n-butyllithium (55 mL; 2.5M) was transferred via nitrogen pump to a pressure equalizing dropping funnel and added to the THF solution. After stirring 15 minutes, the temperature of the mixture was at −78° C. The solid bis-bromide product of example 6 (21 g; 0.042 mole) was then added (Gooch tube) portionwise over an 11 minute period. The temperature did not exceed −75° C. during the addition. Gradually, the suspension changed from brown to brown-green, but solids were still evident after 10 minutes. The bath was lowered and the reaction mixture was allowed to warm to −70° C. over a 10 minute period. The dark green solution was re-cooled to −78° C. and a cold solution (−15° C.) of 20 mL of dimethyl formamide (DMF) in 15 mL of tetrahydrofuran (THF) was added over a three minute period using a nitrogen pump. The temperature rose to −60° C., and, after stirring for 10 minutes, the mixture (at −72° C.) was quenched with an aqueous HCl solution (80 mL HCl diluted to 240 mL in $H_2O$) over a ten minute period. During the acid quench, the color turned dark yellow. The temperature rose to −35° C., and the green-yellow sludge was allowed to stir for 45 minutes with no external cooling. The reaction mixture was then added to 2 L of $H_2O$ and stirred for 2½ hours. The yellow suspension was filtered through coarse filter paper. Then the yellow cake was washed with 400 mL of $H_2O$, and the product was dried overnight in the filter funnel. In several experiments, the recovery of crude crystalline product ranged from 72–79%. A purified sample (crystallized from ethyl acetate) had a melting point of 228°–229° C.; silica gel TLC using 94 toluene:4 methanol:2 isopropylamine (v/v/v) showed a single spot.

EXAMPLE 9

4'-(4-methoxyphenyl)-2,2':6'2"-terpyridine-6,6"-dicarboxaldehyde, 7a

The dibromide of example 7 (7.46 g, 15.5 mmol), in 100 mL of dry THF, was added dropwise to a solution of 28.1 mL of 1.6M n-BuLi in 20 mL of dry THF under $N_2$ over a 12 min period. The temperature was maintained below −75° C. during the addition with a dry ice/acetone bath. The resulting dark green solution was stirred for 10 minutes followed by addition of 7.5 mL of dry DMF over a 2 min period. After 10 min, 90 mL of a 10% HCl solution was added and the resulting solution was stirred for 45 min with continued cooling. The mixture was partitioned between $CHCl_3$ and $H_2O$ (both solvents pre-cooled to 4° C.) in a separatory funnel. The phases were shaken frequently and allowed to stand at ambient temperature for 15–30 minutes, until the color of the organic phase gradually changed from a greenish hue to golden yellow. The organic phase was washed with saturated NaCl solution and then evaporated to leave a cream-colored residue. This material was triturated with $CH_3CN$ to yield the product as an off-white solid (3.53 g, 60%), mp 225°–227° C. Mass spectrum (FDMS): 395 M+ (m/e).

Anal. Calcd for $C_{24}H_{17}N_3O_3$: C, 72.90; H, 4.33; N, 10.63. Found: C, 72.44; H, 4.31; N, 10.46.

EXAMPLE 10

6,6"-Bis(hydroxymethyl)-4'-(4-methoxyphenyl)-2,2':6',2"-terpyridine, 8a

To a stirred suspension of 4'-(4-methoxyphenyl)-2,2':6'2"-terpyridine-6, 6"-dicarboxaldehyde from example 8 (18.5 g; 46.8 mmoles) in 250 mL absolute ethanol at room temperature was added, portionwise, $NaBH_4$ (2.3 g; 60.8 mmoles) over about 10 minutes. Refluxing the mixture for 15 minutes gave a yellow solution, which was stirred for an additional 30 minutes and then diluted with 150 mL $H_2O$. A precipitate developed, and after stirring for a further one and one-half hours, the reaction mixture was filtered. The light tan crystals, after drying, weighed 16 g (86% yield). The crude crystalline product was used without further purification in the next step.

EXAMPLE 11

6,6"-Bis(hydroxymethyl)-4'-(4-methoxyphenyl)-2,2':6',2"-terpyridine, 8a

The crude dialdehyde of example 9 (3.53 g, 8.93 mmol) was refluxed with 1 g of $NaBH_4$ in a mixture of 70 mL of THF and 70 mL of absolute EtOH for 15 min under $N_2$. After concentration in vacuo, the residue was refluxed for 30 min in dilute $NaHCO_3$, cooled, filtered, washed with $H_2O$, then dried to give the desired diol as a white solid (3.35 g, 94.4%) with a melting point of 187°–189° C. Mass spectrum (FDMS) 400 MH+, 399M (m/e). The NMR and IR spectra were consistent with the assigned structure and the product was homogeneous by TLC.

Anal. Calcd for $C_{24}H_{21}N_3O_3$: C, 72.17; H, 5.30; N, 10.52. Found: C, 71.71; H, 5.20; N, 10.37.

EXAMPLE 12

Bismesylate of 6,6"-Bis(hydroxymethyl)-4'-(4-methoxyphenyl)-2,2':6',2"-terpyridine, 9a A suspension of the 6,6"-bis(hydroxymethyl)-41-(4-methoxyphenyl)-2,2':6',2"-terpyridine from example 10 (15.4 g; 38.5 mmoles) in 175 mL $CH_2Cl_2$ and triethylamime (17 mL; 120 mmoles) was stirred and cooled to 8° C. A solution of methanesulfonic anhydride (16.8 g; 96.5 mmoles) in 50 mL $CH_2Cl_2$ was added dropwise over 10 to 15 minutes. The mixture gradually went into solution and, near the end of the addition, a color change from red-orange to yellow-green was observed. A silica gel TLC (toluene:MeOH:isopropylamine:: 92:6:2 v/v/v) taken shortly afterwards showed no starting material and a single spot. The mixture was quenched into 200 mL of ice cold $H_2O$, and the layers were separated. The aqueous layer was extracted three times with 100 mL of $CH_2Cl_2$, and the pooled organic layers were washed with 50 ml of $H_2O$. Filtration of the methylene chloride solution through a pad of $MgSO_4$ and ¾" silica gel gave a near colorless filtrate. The solvent was evaporated, and the crude residue was taken up in 100 mL of ethyl acetate to form a slurry. The slurry was cooled, the white crystals were isolated by filtration and dried overnight to give 17.2 g (82%) of desired material. Mp: 190°–192° C.

EXAMPLE 13

Bismesylate of 6,6"-Bis(hydroxymethyl)-4'-(4-methoxyphenyl)-2,2':6',2"-terpyridine, 9a 6,6"-Bis(hydroxymethyl)-4'-(4-methoxyphenyl)-2,2':6', 2"-terpyridine from example 11 (15.4 g, 38.5 mmol) was suspended in a mixture of 17 mL of $Et_3N$ in 175 mL of $CH_2Cl_2$ with stirring at 8° C. To this suspension, a solution of $(CH_3SO_2)_2O$ (16.8 g, 96.5 mmol) in 50 mL of $CH_2Cl_2$ was added dropwise over a 10 min period. The reaction mixture was shaken with water. The organic layer was dried over $Mg_2SO_4$, filtered, and concentrated nearly to dryness. Addition of EtOAc produced the bismesylate as white crystals which were collected and dried (17.2 g, 80.4%). The NMR and IR spectra were consistent with the assigned structure and the product was homogeneous by TLC.

EXAMPLE 14

6,6'-Dicyano-4'-(4-methoxyphenyl)-2,2':6',2"-terpyridine, 10a

To a solution of 6,6'-dibromo-4'-(4-methoxyphenyl)-2, 2':6',2"-terpyridine from example 6 (30.0 g, 0.06 mole) in anhydrous dimethyl formamide (Aldrich HPLC grade, 240 mL) in a 500 mL 3 neck round bottom flask equipped with a condenser, nitrogen inlet adapter, and a mechanical stirrer (glass rod with teflon blade) was added cuprous cyanide (Aldrich, 21.5 g, 0.24 mole) and sodium cyanide (Aldrich, 11.8 g, 0.24 mole) under efficient stirring and nitrogen flow. The mixture was heated on an oil-bath equipped with a temperature controller for about five hours at 155° to 160° C. The reaction mixture was then filtered at 150° C. to remove hazziness. The filtrate was evaporated to dryness under vacuum at 65° to 70° C. The residue was treated with water (30 mL) and stirred with sodium cyanide solution (20.00 g sodium cyanide into 80 mL of water) for about 3 to 4 hours at about 45° C. The crystalline mass of 6,6"-dicyano-4'-(4-methoxyphenyl)-2,2':6',2"-terpyridine was isolated by filtration, washed with water (250 mL), and then dried under vacuum for 16 hours at 50°–55° C. to yield 22.2 g of tan colored product (95 % of theory). The crude product was recrystallized from methylene chloride (1 g in 90 mL). TLC: (silica gel plate; ethyl acetate:hexane::1:1 v/v) showed a single spot (Rf=0.5 approx.). Infrared spectrum: nitrile band around 2200 cm$^{-1}$; mass spectrum (FAB): M+H=390 m/e; $^1$H NMR (CDCl$_3$): 3.9 (s, 3H, OCH$_3$), 7.1 (d, 2H), 7.77 (d, 2H), 7.87 (d, 2H), 8.03 (t, 2H), 8.79 (s, 2H) and 8.85 ppm (d, 2H).

Elemental analysis as $C_{24}H_{15}N_5O_{1.75}$ H$_2$O: Calc'd: C, 68.50; H, 4.42; N, 16.60. Found: C, 68.51; H, 4.50; N, 16.20.

EXAMPLE 15

2-Acetylpyridine-N-oxide, 16

To a solution of 2-acetyl-pyridine (Aldrich, 0.3 mol) in 150 ml of glacial acetic acid was added with stirring 33 ml of 30% hydrogen peroxide (0.32 mol), and the mixture was allowed to react at 60° to 65° C. for 16 h. An additional 3.3 ml of 30% hydrogen peroxide was added, and the mixture was allowed to react at 70° C. for 2 h. After cooling, the water was removed by evaporation at reduced pressure to leave a crude liquid residue which was taken up in an equal volume of 50:50 ethyl acetate and hexane, and the components were separated by chromatography on 330 g of silica gel. Gradient elution starting with 50:50 ethyl acetate/hexane to 100% ethyl acetate and then to 5% methanol gave 13.48 g (33% yield) of 2-acetyl-pyridine-N-oxide. $^1$H NMR (CDCl$_3$): 2.81 (s, 3H, CH$_3$), 7.34 (m, 2H, H$_4$ and H$_5$), 7.71 (d, 1H, H$_3$), and 8.22 ppm (d, 1H, H$_5$); $^{13}$C NMR (CDCl$_3$): 31.3 (CH$_3$), 125.9, 127.4, 128.6, 141.2, and 195.7 ppm (C=O); mass spectrum (DCI) M$^+$H=138 m/e; IR$_{max}$ (film) 1686 cm$^{-1}$ (C=O).

EXAMPLE 16

2-Acetyl-6-cyanopyridine, 14

To a solution of 2-acetylpyridine-N-oxide (0.098 mol) prepared in example 15 in 200 ml of dry methylene chloride was added N,N-dimethylcarbamoyl chloride (0.1 mol), and the reaction mixture was allowed to react at room temperature under nitrogen for 24 h. An additional aliquot of N,N-dimethylcarbamoyl chloride (0.1 mol) was added, followed by an aliquot of cyanotrimethylsilane (0.22 mol), and the resulting mixture was allowed to react at 20° C. for 2 days. Another 4 mL (0.03 mol) of cyanotrimethylsilane was then added, and the mixture was stirred for an additional 24 h. An aqueous solution (200 ml) of 10% K$_2$CO$_3$ was added to the reaction mixture to produce a mild exotherm, and the resulting mixture was stirred for 45 min. The aqueous layer was extracted with 100 ml methylene chloride twice and the organic layer was dried (K$_2$CO$_3$). After stripping the solvent, 16.9 g of crude material was isolated. This crude residue was chromatographed over Florisil to isolate the desired product plus several by-products whose structures were assigned consistent with spectroscopic data obtained. Thus, gradient elution by the series of solvents gave 2-acetyl-6-cyanopyridine (2.0 g) using 50/50 CH$_2$Cl$_2$/hexane v/v. Also isolated were by-products: 2-[2-(6-cyanopyridyl)]-2-trimethylsiloxypropionitrile (0.81 g) eluting with CH$_2$Cl$_2$; 2-[2-(6-cyanopyridyl)]-2-(N,N-dimethylcarbamoyloxy) propionitrile (1.67 g) eluting with 25:75 EtOAc/CH$_2$Cl$_2$; 2-acetylpyridine cyanohydrin (0.42 g) eluting with 50:50 EtOAc/CH$_2$Cl$_2$; and 2-(1-cyano-1-N,N-dimethylcarbamoyloxy)ethylpyridine-N-oxide (1.8 g) eluting with EtOAc. The desired 2-acetyl-6-cyanopyridine exhibited spectroscopic properties consistent with the assigned structure: $^1$H NMR (CDCl$_3$): 2.75 (s, 3H, CH$_3$), 7.9 (d, 1H), 8.05 (t, 1H), and 8.25 ppm (d, 1H); $^{13}$C NMR (CDCl$_3$): 26.18 (CH$_3$), 117.23 (CN); 125.07, 131.89, 133.72, 138.84, 154.94, and 198.75 ppm (C=O); mass spectrum, (DCI) M$^+$H=147 m/e; IR (CDCl$_3$)$_{max}$ 1709 cm$^{-1}$ (C=O) [2244 cm$^{-1}$, weak, C≡N].

EXAMPLE 17

3-(4-methoxyphenyl)-1-[2-(6-cyanopyridyl)]-2-propenone, 17a.

A mixture of 0.33 g of 2-acetyl-6-cyanopyridine from example 16, 0.28 mL of p-anisaldehyde, 1.9 g of basic alumina (activity grade I), and 6 mL of anhydrous tetrahydrofuran was stirred at room temperature under a nitrogen atmosphere for 24 hrs. The reaction mixture was filtered, and the solid product was rinsed with fresh tetrahydrofuran. The filtrate was evaporated under reduced pressure to yield a yellow solid residue which weighed 0.6 g. The product was purified using silica gel chromatography, eluting with 35% hexane in methylene chloride, to yield 0.4g (72%) of desired material. A sample for combustion analysis was isolated by vacuum sublimation at 130° C./0.01 mm. Melting point: 132.0 to 132.5° C. Mass spectrum: M$^+$=264 m/e; IR (1%KBr): weak absorbance at 2237 cm$^{-1}$ (CN), strong absorbance at 1670 cm$^{-1}$ (unsaturated C=O), and many more absorbances, the seven strongest at 1591, 1566, 1512, 1257, 1217, 1181, and 1042 cm$^{-1}$; $^1$H NMR (CDCl$_3$): 4.87 (s, 3H, —OMe), 6.96 (d, 2H, 2 ortho H's on phenyl), 7.71 (d, 2H, 2 other ortho H's on phenyl), 7.85–8.15 (complex multiplet, 4H, pyridyl & vinyl), and 8.4 ppm (d, 1H); $^{13}$C NMR (CDCl$_3$): 14 lines corresponding to 14 distinct carbons: 56.0, 115.1, 117.4, 126.3, 128.2, 131.4, 131.5, 133.3, 138.8, 146.7, 156.0, 162.8, and 187.7 ppm.

Anal.Calc'd for $C_{16}H_{12}N_2O_2$: C, 72.71%; H, 4.58%; N, 10.60%. Found: C, 72.36%; H, 4.42%; N, 10.53%.

EXAMPLE 18

1-[2-(6-cyano-2-pyridyl)-2-oxoethyl]pyridinium iodide, 18.

To a mixture of 2-acetyl-6-cyanopyridine prepared in example 16 (1.78 mmol) and iodine (1.78 mmol) was added 2.6 ml of pyridine, and the resulting mixture was allowed to react at 100° C. under N$_2$ for 45 min. The reaction mixture was cooled, the product was isolated by filtration, washed with CH$_2$Cl$_2$, and dried under vacuum to yield 0.485 g of pyridinium salt (78%). $^1$H NMR (DMSO-D$_6$): 3.35 (s, exchanges with D$_2$O), 6.5 (s, 2H, —CH$_2$), 8.25 to 8.5 (m, 5H), 8.75 (t, 1H), and 8.97 ppm (~d, 2H); $^{13}$C NMR DMSO-D$_6$: 66.75 (—CH$_2$—), 117.1 (CN), 125.94, 128.19, 132.4 (weak), 133.95, 140.82, 146.71, 146.91, 151.92 (weak), and 190.30 ppm (C=O).

Molecular formula: $C_{13}H_{10}IN_3O$; Calculated: C, 44.46; H, 2.87; N, 11.96; I, 36.14; Found: C, 44.45; H, 2.75; N, 11.84; I, 36.27.

EXAMPLE 19

6,6"-Dicyano-4'-(4-methoxyphenyl)-2,2':6',2"-terpyridine, 10a

Vacuum dried 1-[2-(6-cyano-2-pyridyl)-2-oxoethyl]pyridinium iodide of example 18 (192 mg, 0.55 mmol), 3-(4-methoxyphenyl)-1-[2-(6-cyanopyridyl)]-2-propenone of example 17 (145 mg, 0.55 mmol) and $NH_4OAc$ (212 mg, 2.75 mmol) in 1.5 mL of AcOH (Baker; ultra grade) were heated to 80° C. for 1.5 hours, then for 6.5 hours at 65° C., and then for 16 h at 90° C. Thin layer chromatography (silica gel; 70% hexane, 30% ether, 4% methanol, 1% triethylamine) indicated no starting 3-(4-methoxyphenyl)-1-[2-(6-cyanopyridyl)]-2-propenone remained. The reaction mixture was cooled in ice water; the precipitated crude product (196 mg) was isolated by filtration, and then triturated twice with water. The resulting tan solid (142 mg) exhibited $^1H$ NMR and mass spectral properties identical to the 6,6'-dicyano-4'-(4-methoxyphenyl)-2,2':6',2"-terpyridine prepared in example 14. Mass spectrum (FAB): M+H=390 m/e.

EXAMPLE 20

6,6"-Bis(aminomethyl)-4'-(4-methoxyphenyl)-2,2':6',2"-terpyridine, 11.

6,6"-Dicyano-4'-(4-methoxyphenyl)-2,2':6',2"-terpyridine (1.556 g, 4.0 mmole) prepared in example 14 was dissolved in Ultrex acetic acid (130 mL, Baker) in a Parr hydrogenation bottle by warming to 50° C. for 25 minutes. The solution was sparged with argon for 5 minutes, 10% Pd/C (470 mg) was added under argon, and the reaction mixture was hydrogenated at 45 psi and 45° C. for 19 hours in a Parr hydrogenation apparatus. After venting excess hydrogen and replacing it with argon, the catalyst was removed by filtration using 5 mL of acetic acid as a wash. Most of the solvent was then evaporated under reduced pressure at 35° C. Residual acetic acid was removed by a series of consecutive additions and co-evaporations using 2×30 mL aliquots of toluene, then 2×30 mL aliquots of methylene chloride, and finally 2×30 mL aliquots of ethanol. The product was then dried under vacuum at 30° C. overnight to give 2.3 g (99.5 % recovery) of product as an off-white solid. Thin layer chromatography (silica gel; 85% methylene chloride, 5% methanol, 10% $NH_4OH$, v/v/v) showed the desired product as a spot with an Rf of 0.3 (with some streaking) plus a trace amount of a small spot at the origin. Infrared and mass spectra were in good agreement for the desired product. $^1H$ NMR (DMSO-$D_6$) 3.85 (s, 3H, $OCH_3$), 4.07 (s, 4H, $CH_2$—N), 7.16 (d, 2H), 7.55 (d, 2H), 7.99 (d, 2H), 8.03 (t, 2H), 8.52 (d, 2H) and 8.78 ppm (s, 2H).

An elemental analysis of the crude product was obtained, calculated as $C_{24}H_{23}N_5O \cdot 3CH_3COOH \cdot H_2O$: Calc'd: C, 60.50; H, 6.21; N, 11.75. Found: C, 60.38; H, 6.45; N, 11.20.

EXAMPLE 21

4-(4-methoxyphenyl)-13,21,27,28,29,30-hexaazapentacyclo-[21.3.1.1$^{2,6}$1$^{7,11}$.1$^{15,19}$]-triaconta-1$^{27}$,2,4,6$^{28}$,7,9,11$^{29}$,15,17,19$^{30}$,23,25-dodecaene-14,20-dione.

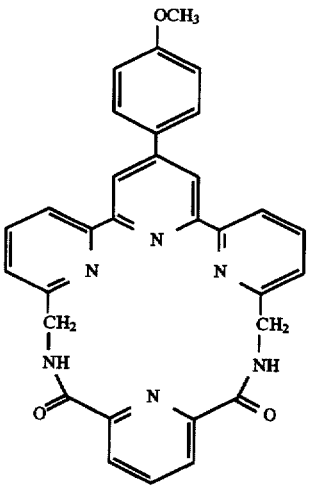

6,6"-Bis(aminomethyl)-4'-(4-methoxyphenyl)-2,2':6',2"-terpyridine (2 mmol) prepared in example 20 was dissolved in a mixture of diisopropylethylamine (517 mg, 4 mmol), anhydrous THF (41 mL), and anhydrous DMF (9 mL) under anhydrous conditions to form Solution A. Pyridine carbonyl dichloride (420.7 mg, 2 mmol) was dissolved in anhydrous THF (50 mL) under anhydrous conditions to form Solution B. Anhydrous THF (300 mL, "Solution" C) was added to a one liter three necked flask equipped with a magnetic stirring bar, a rubber septum, and nitrogen inlet and outlets. Solution A and Solution B were added dropwise to Solution C simultaneously from two 50 mL syringes using a syringe pump at room temperature over a period of 12 hours. The reaction mixture was allowed to stir for three hours at room temperature, the solvent was evaporated, and the residue was dissolved in methylene chloride (250 mL). The methylene chloride solution was washed with water, 0.1N HCl, water, 5% $NaHCO_3$ aqueous solution, water, then dried over anhydrous $Na_2SO_4$, filtered, and evaporated to give a pinkish white crude solid (605 mg). The crude product was purified on a silica gel column (12.0 g; EM, 230–240 mesh), eluting sequentially with methylene chloride (100 mL), 1% methanol/methylene chloride (200 mL), and then 2.5% methanol/methylene chloride (500 mL) to give 158 mg (14.9 %) of desired product. Mass spectrum: (M+H)=529 m/e; $^1H$ NMR (CDCl$_3$) 3.89 (s, 3H), 4.89 (s, 4H), 4.70 (s, 2H), 7.1 (d, 2H), 7.5 (d, 2H), 7.7 (d, 2H), 7.85 (m, 3H), 7.98 (s, 2H), 8.27 (d, 2H) and 8.43 ppm (d, 2H).

EXAMPLE 22

4'-(4-methoxyphenyl)-2,2':6'2"-terpyridine-6,6"-dicarboxylic acid, 12a

A flame dried 3 necked 1 L flask equipped with a mechanical stirrer, pressure equalizing addition funnel, and, attached via silicone rubber tubing, a Gooch tube containing solid 4'-(4-methoxyphenyl)-2,2':6'2"-terpyridine-6,6"-dibromide, 6a, (21.0 g; 42.2 mmole) under nitrogen is charged with 400 mL THF and cooled in a Dry Ice/ether bath to −78° C. A solution of n-butyllithium (40 mL of 2.5M) is

95 transferred via nitrogen pump to the pressure equalizing addition funnel, and is then added to the THF solution. After stirring 15 minutes at −78° C., the solid 4'-(4-methoxyphenyl)-2,2':6'2"-terpyridine-6,6"-dibromide is added portionwise over an 11 minute period from the Gooch tube. The temperature is not allowed to exceed −75° C. during the addition. After the addition, the bath is lowered, and the reaction mixture is allowed to warm slightly to −70° C. over a 10 minute period. The solution is re-cooled to −78° C., and the reaction mixture is transferred via cannula under nitrogen to a jacketed addition funnel cooled to −78° C. This anionic solution is maintained at −78° C. under nitrogen while it is added with stirring to 400 mL of THF saturated with anhydrous carbon dioxide in a 3 L 3 necked flask attached to a silicone oil bubbler. Additional anhydrous carbon dioxide is slowly bubbled into the reaction mixture during the addition while the temperature is carefully controlled to remain below −70° C. After stirring for 60 minutes, the cooling bath is removed and the reaction mixture is carefully quenched with 100 ml of a 1N aqueous HCl solution over a ten minute period. The reaction mixture is allowed to stir and warm to room temperature. The solvent is evaporated under vacuum below 20° C., the crude product is triturated with isopropanol, isolated by filtration, washed with ether and dried under vacuum.

EXAMPLE 23

4'-(4-methoxyphenyl)-2,2':6'2"-terpyridine-6,6"-dicarbonyl chloride, 13

To 1 g of 4'-(4-methoxyphenyl)-2,2':6'2"-terpyridine-6,6"-dicarboxylic acid from example 22 is added a solution of 1 mL of thionyl chloride in 25 mL of methylene chloride. The reaction mixture is heated gently for 1 hour, and the solvent and excess thionyl chloride are removed under reduced pressure. The crude product is triturated with anhydrous heptane and isolated by filtration under nitrogen.

EXAMPLE 24

4-(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,11$^{29}$,15,17,19$^{30}$, 23,25-dodecaene-12, 22-dione.

This material is prepared from 4'-(4-methoxyphenyl)-2,2':6'2"-terpyridine-6,6"-dicarbonyl chloride, 13, and 2,6-bisaminomethylpyridine by the method used in example 21.

EXAMPLE 25

4-(4-methoxyphenyl)-13,21,27,28,29,30-hexaazapentacyclo-[21.3.1. 1$^{26}$.1$^{7,11}$.1$^{15,19}$]-triaconta-1$^{27}$,2,4,6$^{28}$,7,9,11$^{29}$,15,17,19$^{30}$,23,25-dodecaene, 54a.

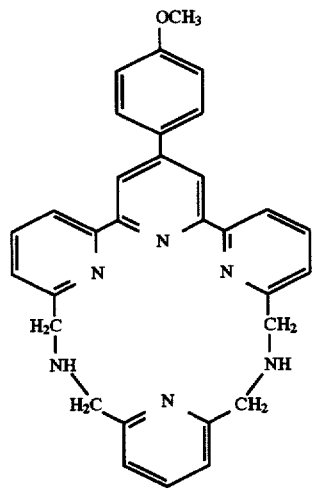

4(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,11$^{29}$,15,17,19$^{30}$,23,25-dodecaene-14,20-dione from example 21 is dissolved in tetrahydrofuran under anhydrous nitrogen and treated with diborane in tetrahydrofuran at room temperature for 24 hours. After quenching with methanol at ice temperature, the solvent is evaporated, the product is taken up in methylene chloride, washed with water, then with saturated sodium bicarbonate solution, dried over sodium sulfate, filtered, and the solvent is evaporated. The desired material is triturated with cold methanol, isolated by filtration, and dried.

EXAMPLE 26

4-(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,11$^{29}$,15,17,19$^{30}$,23,25-dodecaene, 54a This material is prepared using the method of example 25 from 4-(4-methoxyphenyl)-13,21,27,28,29,30-hexaazapentacyclo-[21.3.1.1$^{2,6}$.1$^{7,1}$.1$^{15,19}$]-triaconta-1$^{27}$,2,4,6$^{28}$,7,9,11$^{29}$,15,17,19$^{30}$,23,25-dodecaene-12,22-dione of example 24.

EXAMPLE 27

13-[2-(1,3-dioxolanyl)methyl]-4-(4-methoxyphenyl)
-13,21,27,28,29,30-hexaazapentacyclo-[21.3.1.1$^{2,6}$.1$^{7,11}$.1$^{15,19}$]-triconta-1$^{27}$,2,4,6$^{28}$,7,9,11$^{29}$,15,17,19$^{30}$,23,25-dodecaene, 55a.

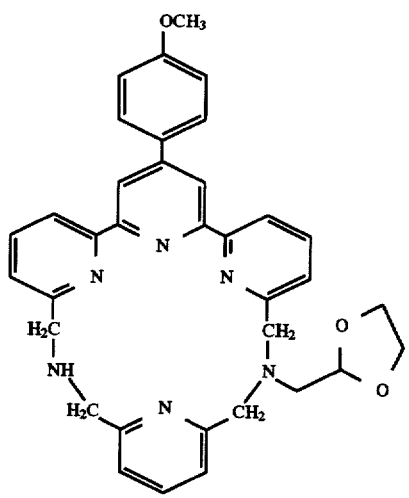

A solution 0.01 mmol of 4-(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,11$^{30}$,23,25-dodecaene prepared in example 25 plus 0.01 mmol of diisopropylethylamine in anhydrous methylene chloride at ambient temperature is treated with 0.01 mmol of 2-bromomethyl-1,3-dioxolane (Aldrich), and the reaction is followed by thin layer chromatography on silica gel using methylene chloride containing 1% methanol. When the 2-bromomethyl-1,3-dioxolane is reacted, the reaction mixture is washed with saturated sodium bicarbonate solution and evaporated. The desired 1:1 adduct is separated from unreacted starting material and 2:1 adduct by chromatography on silica gel using methylene chloride and 1% to 5% gradient of methanol.

EXAMPLE 28

21-Carboxymethyl-13-(2-formylmethyl)-4-(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,11$^{29}$,15,17,19$^{30}$,23,25-dodecaene, 56a.

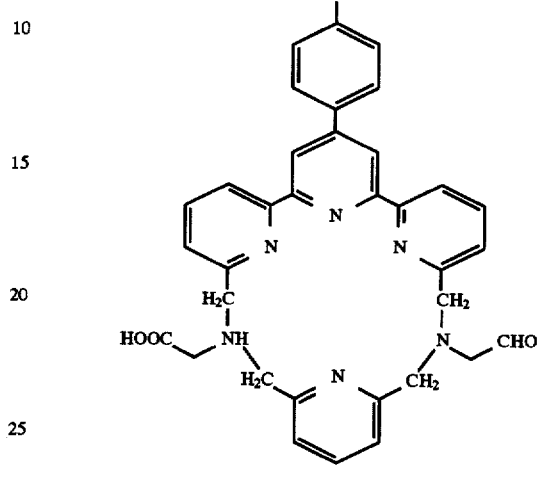

A solution of 1 mmol of 13-[2-(1,3-dioxolanyl)methyl]-4-(4-methoxyphenyl)-13,21,27,28,29,30-hexaazapentacyclo-[21.3.1.1$^{2,6}$.1$^{7,11}$.1$^{15,19}$]-triaconta-1$^{27}$,2,4,6$^{28}$,7,9,1$^{29}$,15,17,19$^{30}$,23,25-dodecaene, 55a, in 50 mL of anhydrous dimethylformamide and 2 mmol of diisopropylethylamine is treated with 1 mmol of bromoacetic acid (Aldrich) at 80° C. for 24 hours. The solvent is evaporated and the residue is taken up in 50 mL of 0.1N HCl at room temperature. After 12 h, the reaction mixture is extracted three times with equal volumes of ether. The pH of the aqueous layer is adjusted to 10 with cold 1N NaOH solution and then extracted three times with equal volumes of ether. After readjusting the pH of the solution to 4 with 1N HCl, the product is further purified by ion exchange chromatography.

EXAMPLE 29

N-(3-Hydroxypropyl)-2,2'-iminodiacetamide, 25.

In a two liter 3 necked flask equipped with a nitrogen inlet and outlet, an addition funnel, a thermometer and a mechanical stirrer, iodoacetamide (200 g, 1.08 mol) was suspended with stirring in anhydrous acetonitrile (700 mL), and the contents of the flask were cooled to 0° C. A mixture of 3-aminopropanol (38.72 g; 0.516 mol) and triethylamine (130.38 g; 1.29 mol dissolved in anhydrous acetonitrile (412 mL) was added to the iodoacetamide suspension at 0° C. over a period of 15 minutes. The reaction mixture was stirred at 0° C. for one hour and then for about 18 hours at room temperature. The precipitate from the reaction mixture was isolated by filtration, dried under suction, and slurry washed with chloroform (2×150 mL). It was then dried at 50° C. under vacuum to yield white crystalline crude product (55 g, 56%). The crude product was recrystallized from boiling methanol (120 mL) plus acetone (120 mL) to yield pure product (52.4 g; 53.7%). Mp: 118°–120° C.; mass spectrum: 190 (strong MH+), 159, 145; $^1$H NMR ($D_2O$) : 1.7 to 1.8 (m, 2H), 2.6 to 2.7 (t, 2H), 3.3 (s, 4H), and 3.6 to 3.7 ppm (t, 2H).

Calculated for $C_7H_{15}N_3O_3$: C, 44.43; H, 7.99; N, 22.21 Found: C, 44.37; H, 7.42; N, 21.72.

EXAMPLE 30

N,N-Bis(2-aminoethyl)propanolamine, 26

Into a two liter three necked round bottom flask equipped with a mechanical stirrer, a nitrogen inlet and outlet, a thermometer and a powder addition funnel, $BH_3$.THF (1 Molar solution, 1200 mL; 1.2 mol) was charged under nitrogen. The flask was cooled to 0° C. and then N-(3-hydroxypropyl)-2,2'-iminodiacetamide, 25, (20.0 g; 0.106 mol) from example 29 was slowly added over a period of one hour. The reaction mixture was then refluxed for 24 h. After cooling to 0° C., methanol (300 mL) was added slowly and stirring was continued at room temperature overnight. HCl gas was then bubbled into the clear reaction mixture. A white, gummy material precipitated. The THF and methanol mixture was decanted to leave behind a sticky residue which was dissolved in methanol. The solvent was then evaporated on a rotavap under vacuum.

The free N,N-bis(2-aminoethyl)propanolamine was liberated by passing the solution of this hydrochloride in methanol through a 2.5 inch column of Biorad Anion Exchange Resin AG 1×8 (20 to 50 mesh; hydroxide form; 500 g). The elution was carried out with methanol (2,500 mL). The crude amine was freeze-dried to yield a light yellow oil (14.0 g, 82%). TLC of the crude amine (silica gel; 20% aqueous ammonium hydroxide/80% isopropanol) showed one major product spot, Rf=0.30, and three faint faster moving spots when visulized with ninhydrin. The crude oil was further purified by distillation (1.6 mm vacuum).

A pure fraction of colorless hygroscopic oil was collected between 125°–130° C. (9.00 g; 52.8 % yield). $^1$H NMR ($CDCl_3$): 2.7 (m, 2H, —$CH_2CH_2OH$), 2.4(s, 5H, 2—$NH_2$ and —OH), 2.5(t, 4H, two —$NH_2CH_2$—), 2.7(t, 2H, —$NCH_2CH_2CH_2OH$), 3.8 (t, 4H, —$NCH_2CH_2NH_2$), and 4.7–4.8 ppm (t, 2H, —$CH_2OH$); IR analysis was consistent with the postulated structure (no C=O stretching band; broad hydroxyl O—H).

Elemental analysis calculated for $C_7H_{19}N_3O.¼H_2O$: Calculated: C, 50.75; H, 11.78; N, 25.37 Found: C, 50.51; H, 11.93; N, 24.79.

EXAMPLE 31

DiBOC derivative of N,N-Bis(2-aminoethyl)-propanolamine, 27

To a solution of N,N'-Bis(2-aminoethyl)propanolamine (2.35 g, 0.01 mol) from example 30 in a mixture of butanol (25 mL) and methanol (10 mL) was added diisopropylethylamine (5.2 g, 0.04 mol) and N,N-dimethylaminopyridine (a few crystals). A solution of di-t-butyl dicarbonate (4.37 g; 0.02 mol) in methylene chloride was then added dropwise over a period of 45 minutes. The reaction mixture was stirred overnight, the solvent was evaporated, and the residual liquid was dissolved in water (30 mL). The aqueous solution was saturated with sodium chloride and extracted with methylene chloride (3×30 mL). The combined extracts were washed with $H_2O$, and the solvent was evaporated to yield a yellowish, oily crude product (7.8 g) which was purified by flash chromatography (silica gel column: 5" diameter×7.5" high). The elution was done in the gradient fashion: (a) 2000 mL of 93% methylene chloride, 4% methanol, 3% triethylamine (TEA); (b) 2000 mL of 93% methylene chloride, 5% methanol, 3% TEA; (c) 3000 mL of 90% methylene chloride, 7% methanol, 3% TEA; and (d) 3000 mL of 87% methylene chloride, 10% methanol, 3% 30 triethylamine. The desired product was eluted with 92% methylene chloride, 5% methanol, 3% TEA (1000 mL) and then 90% methylene chloride, 7% methanol, 3% TEA (1500 mL). These fractions were combined and evaporated to yield a yellowish, thick, oily product (2.9 g; 80%). Thin layer chromatography: (a) Silica gel plate using the solvent system: 92% methylene chloride, 4% methanol, 4% isopropylamine showed a single spot, Rf: 0.4, when visualized with ninhydrin; (b) Silica gel plate using the solvent system: butanol 4, acetic acid 1, water 1 showed three spots: a major spot with an Rf of 0.6 and two very minor impurities with Rf: 0.94 and Rf: 0.16 when visualized with ninhydrin. Mass spectrum: 362 (M+H, strong), 306, 250, 231 (strong), 175; $^1$H NMR ($CDCl_3$): 1.4 to 1.5 (s, 18H, t-butyl), 2.7 (m, 2H), 2.5 to 2.6 (t, 4H), 2.6 to 2.7 (t, 2H), 3.2 (m, 4H), and 4.2 to 4.3 ppm (t, 2H). Elemental analysis calculated as $C_{17}H_{35}N_3O_5.½CH_3OH$: Calculated: C, 55.70; H, 9.81; N, 11.14 Found: C, 55.72; H, 9.05; N, 10.69.

EXAMPLE 32

N,N-Bis(2-aminoethyl)propanolamine, 26, from its DiBOC derivative

The diBOC derivative of N,N-bis(2-aminoethyl)-propanolamine (653 mg; 1.81 mmol) from example 31 was stirred with 50% aqueous HCl in methanol (10 mL) for about 2 hours. The solvents were evaporated and the residue was coevaporated with methanol (4×30 mL) to yield a white solid (400 mg). The solid was dissolved in methanol and passed through Biorad Anion Exchange Resin AG 1×8 (20–50 mesh; Hydroxide form) and using 200 mL of methanol. The solvent was evaporated to yield an oily product. $^1$H NMR ($CDCl_3$): 2.7 (m, 2H), 2.4 (s, 5H, $NH_2$ and —OH), 2.5 (t, 4H), 2.7 (t, 2H), 3.8 (t, 4H), and 4.7 to 30 4.8 ppm (t, 2H).

EXAMPLE 33

18-(4-methoxyphenyl)-6-(3-hydroxypropyl)-3,6,9,25,26,27-hexaazatetracyclo-[19.3.1.1$^{11,15}$,1$^{16,20}$]-heptacosa-11,13,15$^{27}$,16$^{26}$,17,19,21$^{25}$,22,24-nonaene, 35a, by non-template synthesis.

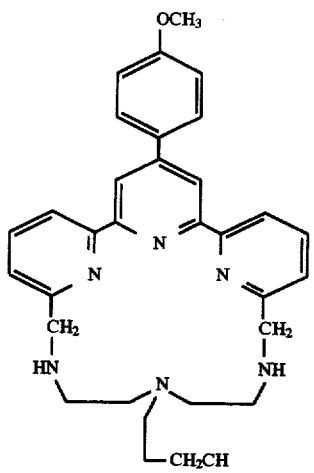

In a 100 mL 3 neck flask equipped with magnetic stirrer, nitrogen inlet and outlets, terpyridine bisaldehyde prepared in example 8 (602 mg; 1.52 mmol) and N,N-bis(2-aminoethyl)propanolamine prepared in example 32 (235 mg; 1.46 mmol) were dissolved in absolute ethanol (13 mL). 3 mL of 0.05 M sodium phosphate buffer, pH 10 5.5, were added and the mixture cooled to 00 C. Freshly prepared sodium cyanoborohydride solution in THF (5.3 mL of 1M solution; 5.3 mmol) was added at 0° C. using a syringe pump over one hour. The reaction mixture was stirred for four more hours at 0° C. and then 16 more hours at room temperature. The reaction mixture was then diluted with methylene chloride, extracted with water, washed with saturated brine solution, dried over anhydrous Na$_2$SO$_4$, filtered, and the solvent was evaporated to yield a pink solid (792 mg). TLC of the crude product (silica gel; 93% methylene chloride, 4% methanol, 3% isopropylamine) showed seven impurities. The crude was purified on a silica gel column (large excess of silica gel; 1:100) by eluting with 2 liters of 93% methylene chloride, 4% methanol, 3% isopropylamine. Fraction No. 7 out of a total eight equal fractions showed the presence of the product by mass spectroscopy; M+=524 m/e).

EXAMPLE 34

18-(4-methoxyphenyl)-6-(3-hydroxypropyl)-3,6,9,25,26,27-hexaazatetracyclo-[19.3.1.1$^{11,15}$,1$^{16,20}$]-heptacosa-11,13,15$^{27}$,16$^{26}$,17,19,21$^{25}$,22,24-nonaene, 35a, by Ni+$^2$ ion template synthesis.

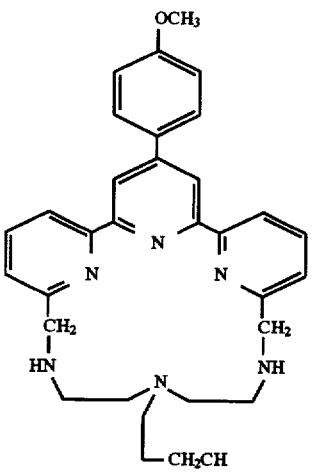

In a 250 mL flask under nitrogen, a mixture of 4'-(4-methoxyphenyl)-2,2':6'2''-terpyridine-6,6''-dicarboxaldehyde, 7a, prepared in example 8 (790 mg, 2 mmol), anhydrous DMF (50 mL) and NiCl$_2$.6H$_2$O (476 mg, 2 mmol) was heated to 7° C., and a solution of N,N-bis(2-aminoethyl)propanolamine from example 32 (322 mg, 2 mmol) in DMF (30 mL) was added in one hour using a syring pump. Thereafter, a 10 mL aliquot of methanol was added, and the reaction mixture was heated for six more hours until the presence of aldehyde could no longer be detected by TLC. The reaction mixture was then cooled to 0° C, and an additional 10 mL of methanol was added, followed by the addition of NaBH$_4$ (455 mg) over a period of one hour. The solution was then stirred over night at room temperature, water (20 mL) was added, and the reaction mixture was stirred for 8 hours. All solvents were then evaporated, the residue was triturated with ether (20 mL), the solid was isolated by filtration, dried on the filter funnel, and then redissolved in water (20 mL). This solution was divided into two equal portions, Portion I and Portion II. Portion I was treated with NaCN (1 g) at 80° C., then extracted with methylene chloride and evaporated to give a brownish solid (410 mg; 78%). Mass spectrum: 547 (M+H), 525, 367 (weak), 340 (weak). A sample for combustion analysis was recrystallized from methanolic HCl and calculated as C$_{31}$H$_{36}$N$_6$O$_2$.3HCl.2CH$_3$OH.H$_2$O: Calculated: C, 55.35; H, 6.90; N, 11.73; Cl, 14.85. Found: C, 53.73; H, 6.27; N, 11.48; Cl, 14.90.

Portion II (3 mL) was treated with NH$_4$PF6 (0.15 g) in water (2 mL). Evaporation and crystallization with methanol gave a solid product. An elemental analysis was calculated for $C_{31}H_{36}N_6O_2(CH_3OH)2.2H_2O$. $PF_6$: Calculated: C, 47.84; H, 5.84; N, 10.14; P, 3.74; F, 13.76; Ni, 7.09; Found: C, 48.34; H, 4.43; N, 9.65; P, 3.86; F, 13.18; Ni, 7.28.

EXAMPLE 35

3,9-Bis(ethoxycarbonylmethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 47a OCH$_3$

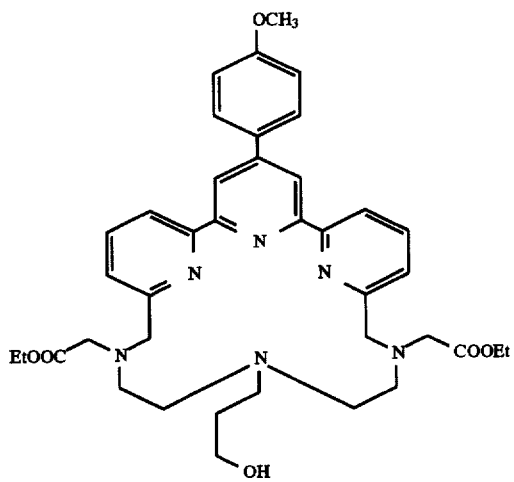

A solution of 18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 35a, prepared in example 34 (1.049 g, 2mmol) and diisopropylethylamine (0.698 g, 5.4 mmol) in 30 mL of methylene chloride was cooled to 0° C. A solution of ethyl bromoacetate (0.902 g, 5.4 mmol) in methylene chloride (20 mL) was added slowly using a syringe pump over a period of one hour. The reaction mixture was then stirred overnight at 0° to 8° C. and washed with water. Then the solvent was evaporated, and the residue was triturated with hexane and dried to give 1.33 g of crude product. A pure 72 mg sample was isolated by silica gel chromatography using 5% aqueous ammonium hydroxide, 5% isopropanol, and 90% acetonitrile. Mass spectrum: 720M+Na (sodium chelate of the desired compound having a molecular weight of 697 for the chelate plus 23 for sodium) 719, 645, 631, and 587; $^1$H NMR (CDCl$_3$) 1.15 (t, 6H), 1.40 (m, 2H), 2.65 to 3.25 (m, 10H), 3.35 (s, 4H), 3.87 (s, 3H), 4.02 (q, 2H), 4.06 (s, 4H), 4.07 (m, 2H), 7.07 (d, 2H), 7.38 (d, 2H), 7.80 (d, 2H), 7.95 (t, 2H), 8.06 (d, 2H) and 8.15 ppm (s, 2H).

Example 36

Disodium 3,9-Bis(carboxymethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-1,13,15$^{27}$,16$^{26}$,17,19,21$^{25}$,22,24-nonaene

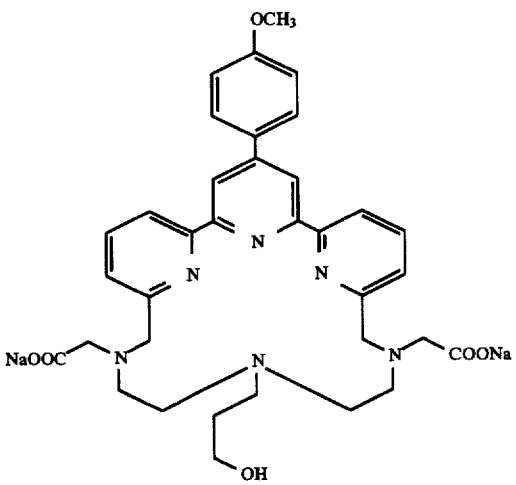

The diester of example 35 (200 mg, 0.287 mmol) dissolved in ethanol (20 mL) was treated with NaOH solution (23.5 mg of NaOH in 0.56 mL of H$_2$O; 0.588 mmol) with stirring for two hours under nitrogen at which time TLC confirmed the absence of the diester. The solvent was evaporated, and the residual solid was dried under vacuum to give 179 mg of a light yellow solid. $^1$H NMR (D$_2$O) 7.56 (s, 2H), 7.35 (d, 2H), 7.10 (m, 4H), 6.55 (d, 2H), 6.32 (d, 2H), 3.97 (s, 3H), 3.25 (s 4H), 3.05 (s, 4H), 3.0 (m, 2H), 2.2 (broadened m, 2H), 1.8 to 2.0 (m, 8H) and 1.35 ppm (m, 2H).

EXAMPLE 37

3,9-Bis(ethoxycarbonylmethyl)-18-(4-methoxyphenyl)-6-(3-methanesulfonyloxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 48a

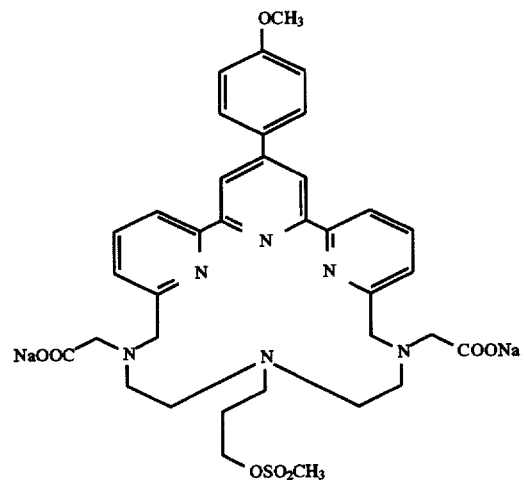

To a stirred mixture of 3,9-bis(ethoxycarbonylmethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 47a, from example 35 (100 mg, 0.14 mmol) and 50 mg of 2,6-lutidine in 20 mL of methylene chloride at 8° C. is added a solution of methanesulfonic acid anhydride (30 mg, 0.17 mmol, Aldrich) in 3 mL of methylene chloride dropwise over a 10 min period. The reaction mixture is then shaken with 50 mL of ice water. The organic layer is separated and dried in an ice-cooled flask over Na$_2$SO$_4$, filtered, and concentrated nearly to dryness below 10° C. EtOAc is then added to precipitate the desired crude product mesylate, which is collected by filtration and used without further purification.

EXAMPLE 38

3,9-Bis(carboxymethyl)-18-(4-methoxyphenyl)-6-(3-sulfhydrylpropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 49a

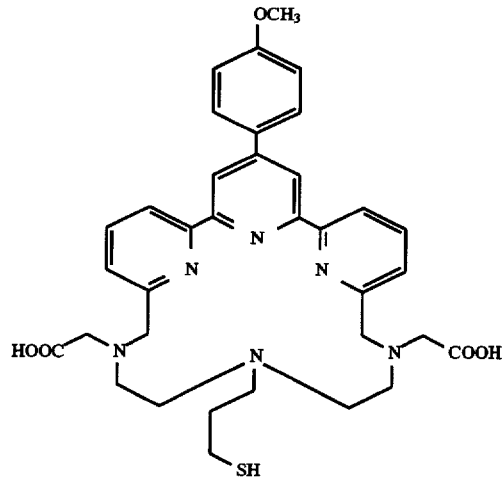

A mixture of the mesylate of example 37 (0.1 mmol) and thiourea (0.1 mmol) in oxygen-free ethanol (50 mL) is heated under argon at reflux for 3 hours. 1 mL of 1N NaOH solution (oxygen-free) is then added, and the reaction mixture is heated for another 2 hours to saponify the esters and the isothiourea methansulfonate. The reaction mixture is cooled to ice temperature and acidified with 1N HCl to provide the desired compound, which can be used without further purification.

EXAMPLE 39

3,9-Bis(t-butoxycarbonylmethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 36a

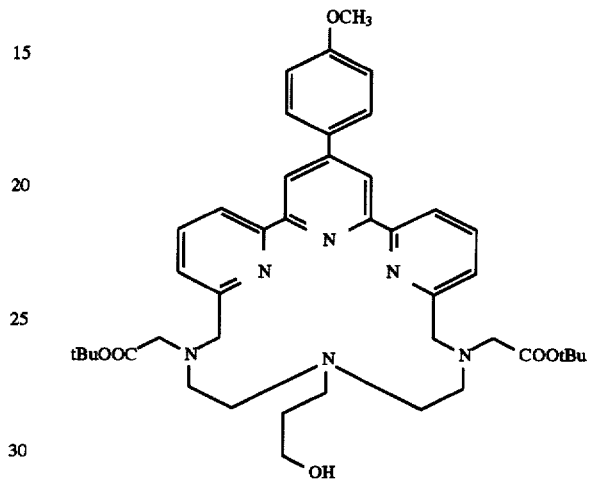

A solution of 18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 35a, prepared in example 34 (1.049 g, 2mmol) and diisopropylethylamine (0.698 g, 5.4 mmol) in 30 mL of methylene chloride is cooled to 0° C. A solution of t-butyl bromoacetate (5.4 mmol) in methylene chloride (20 mL) is added. The reaction mixture is then stirred for 24 hours at room temperature, washed with water, the solvent is evaporated, and the residue is triturated with hexane. The desired product is isolated by filtration and dried under vacuum. A pure sample is isolated by silica gel chromatography using 5% aqueous ammonium hydroxide, 5% isopropanol, and 90% acetonitrile.

EXAMPLE 40

3,9-Bis(t-butoxycarbonylmethyl)-18-(4-methoxyphenyl)-6-(3-methansulfonyloxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 37a

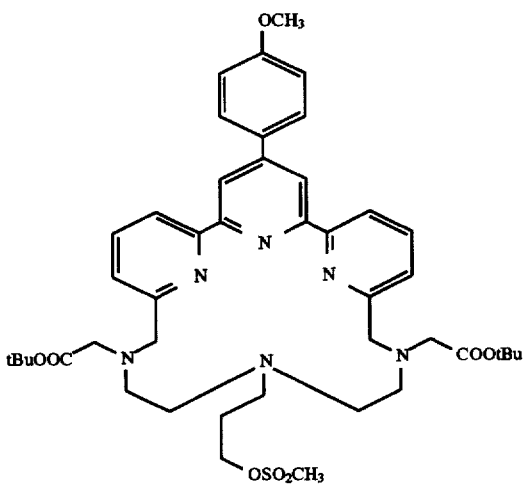

3,9-Bis(t-butoxycarbonylmethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 36a, from example 39 is treated with methanesulfonic acid anhydride and 2,6-lutidine according to the method of example 37 to provide crude 3,9-bis(t-butoxycarbonylmethyl)-18-(4-methoxyphenyl)-6-(3-methansulfonyloxypropyl)-3,6,9,25,26,27-hexaazatetracyclo- [19.3.1.1$^{11,15}$.1$^{16,20}$]-heptacosa-11,13,15$^{27}$,16$^{26}$,17,19,21$^{25}$,22,24-nonaene, 37a.

EXAMPLE 41

3,9-Bis(carboxymethyl)-18-(4-methoxyphenyl)-6-(3-aminopropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene

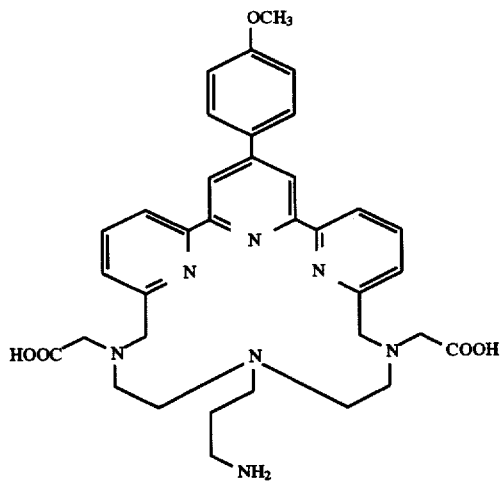

3,9-Bis(t-butoxycarbonylmethyl)-18-(4-methoxyphenyl)-6-(3-methansulfonyloxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 37a, of example 40 (0.1 mmol) in dimethylformamide (20 mL) is treated with sodium azide (0.1 mmol) for 24 hours at room temperature and then with triphenylphosphine (0.1 mmol). After stirring overnight, the solvent is evaporated under vacuum and the residue is treated with 20 mL of 1N HCl and stirred at room temperature for 8 hours. The reaction mixture is then extracted with ether (20 mL), and the aqueous layer is evaporated to provide the desired compound as a hydrochloride salt.

EXAMPLE 42

3,9-Bis(t-butoxycarbonylmethyl)-18-(4-methoxyphenyl)-6-[3-(4-nitrophenylmethyl)oxypropyl]-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 45a

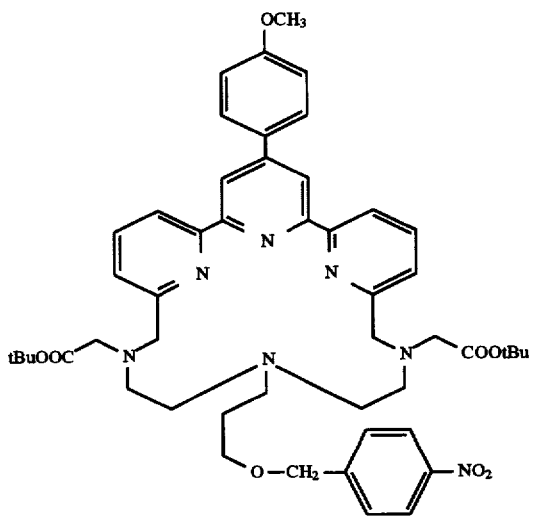

A solution of 3,9-bis(t-butoxycarbonylmethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 36a, of example 39 (0.10 mmol) in 20 mL of DMF is treated with 0.10 mmol of sodium hydride for 3 hours at 30° C. followed by 0.10 mmol of p-nitrobenzyl chloride. The reaction mixture is kept at 40° C. for 6 hours, the solvent is evaporated under vacuum, the residue is triturated with hexane, the crude product is isolated by filtration, washed with water, and dried.

EXAMPLE 43

Disodium 3,9-Bis(carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13,15$^{27}$,16$^{26}$, 17,19,21$^{25}$,22,24-nonaene, 46a

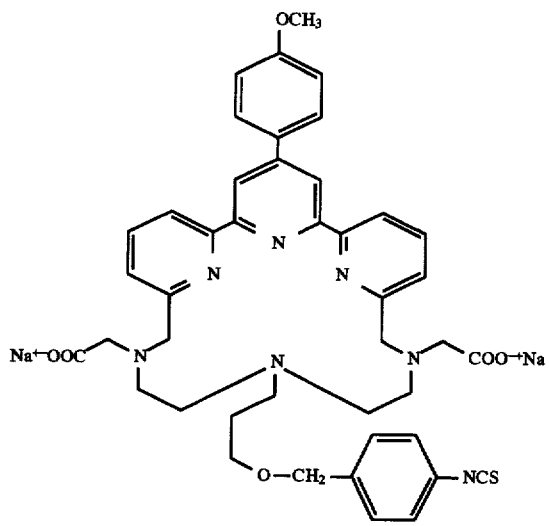

0.1 mmol of 3,9-bis(t-butoxycarbonylmethyl)-18-(4-methoxyphenyl)-6-[3-(4-nitrophenylmethyl)oxypropyl]-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 45a, from example 42 in methanol (50 ml) is treated with sulfated sodium borohydride at room temperature for 4 hours. The reaction mixture is carefully acidified with 1N HCl solution and then is heated to 40° C. for 4 hours. The reaction mixture is cooled in ice, made basic with 1N NaOH solution, and the solvent is evaporated. The crude amino acid disodium salt is then isolated by filtration and washed with ether. The product is then added to 50 mL of methanol and is treated first with thiophosgene (0.1 mmol) in tetrahydrofuran (1:2 v/v) at ambient temperature and then with triethylamine (0.1 mmol). After one hour, the reaction mixture is concentrated to a residue, slurried with dichloromethane, and the product is isolated by filtration.

EXAMPLE 44

3,9-Bis (carboxymethyl)-18-(4-methoxyphenyl)-6-(3-thiomethylcarbonylaminopropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene

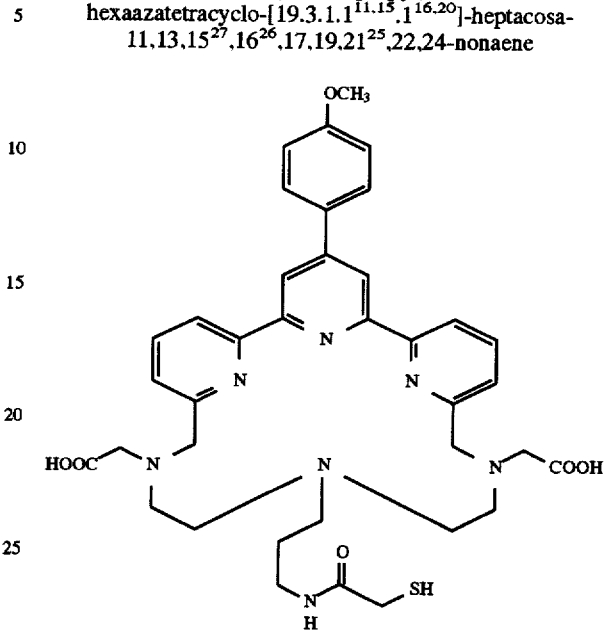

A mixture of 0.10 mmol of 3,9-bis(carboxymethyl)-18-(4-methoxyphenyl)-6-(3-aminopropyl)-3,6,9,25,26,27-hexaazatetracyclo-[19.3.1.1$^{11,15}$.1$^{16,20}$-heptacosa-11,13,15$^{27}$,16$^{26}$,17,19,21$^{25}$,22,24-nonaene of example 41 and 0.3 mmol of diisopropylethylamine in 25 mL of deoxygenated DMF is treated under argon with 0.10 mmol of N-succinimidyl-S-acetylthioacetate (SATA; Pierce Chemical Company) for 6 hours at room temperature. An aliquot of 0.3 mmol of NaOH in 5 mL of oxygen-free water is added, and the solvent is removed under high vacuum. The residue is triturated in cold deoxygenated ethyl acetate and the solid is isolated by filtration. This material is taken up in 0.1N water and treated with hydroxylamine hydrochloride (0.1 mmol) for two hours at room temperature. The solvent is removed under high vacuum, the residue is triturated with cold oxygen-free isopropyl alcohol and isolated by filtration. The product is kept under argon until used.

EXAMPLE 45

Preparation of Antibody-Maleimide with Sulfo-SMCC (ING-1-Maleimide)

A solution of 36 nmoles of sulfosuccinimidyl 4-(N-maleimidomethyl)cyclohexane-1-carboxylate (sulfo-SMCC; Pierce Chemical Company) in PBS is added to a sample of 6 nmoles of ING-1, a chimeric antibody, in phosphate buffer at pH 7. The resulting mixture is allowed to stand for 30 minutes with occasional mixing at room temperature. The reaction mixture is diluted with phosphate buffered saline, added to a prewashed PD-10 column (Pharmacia), and is eluted with PBS to afford ING-1-maleimide. This material is stored on ice until used.

EXAMPLE 46

Conjugation of 3,9-bis(carboxymethyl)-18-(4-methoxyphenyl)-6-(3-thiomethylcarbonylaminopropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene to ING-1-maleimide A sample (50 nmoles) of 3,9-bis(carboxymethyl)-18-(4-methoxyphenyl)-6-(3-thiomethylcarbonylaminopropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene from example 44 is added under argon to an oxygen-free solution of maleimide-derivatized ING-1 (5 nmoles) prepared according to example 45. After a brief mixing, the solution is rapidly concentrated by centrifugation in a Centricon-100 device to a concentration of approximately 3.0 mg/mL of protein. The reaction then is allowed to proceed for 4 hours at room temperature. The antibody-chelate conjugate is transfered to a Centricon-30® concentrator and diluted with PBS. After concentrating the protein down to a volume of approximately 500 uL by centrifugation, the material is again diluted with PBS to 3.0 mL and recentrifuged. This procedure, which separates low molecular weight products from the retained antibody-chelate conjugate is repeated 4 times. Finally, the material in the Centricon-30® is concentrated to approximately 1.0 mg/mL protein in solution. The conjugate is sterile filtered through a 0.22 u filter and stored at 4° C. until use.

EXAMPLE 47

Conjugation of 3,9-Bis(carboxymethyl)-18-(4-methoxyphenyl)-6-(3-sulfhydrylpropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 49a, to ING-1-maleimide 3,9-Bis(carboxymethyl)-18-(4-methoxyphenyl)-6-(3-sulfhydrylpropyl)-3,6,9,25,26,27-hexaazatetracyclo-[19.3.1.1$^{11,15}$.1$^{16,20}$]-heptacosa-11,13,15$^{27}$,16$^{26}$,17,19,21$^{25}$, 22,24-nonaene, 49a, of example 38 is conjugated to ING-1-maleimide of example 45 by the method of example 46.

EXAMPLE 48

Conjugation of disodium 3,9-bis(carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 46a, to ING-1 antibody.

ING-1 antibody (50 nmoles) is allowed to react with disodium 3,9-bis(carboxymethyl)-18-(4-methoxyphenyl)-6-13-(4-isothiocyanatophenylmethyl)-oxypropyl]-3,6,9,25,26,27-hexaazatetracyclo-[19.3.1.1$^{11,15}$.1$^{16,20}$]-heptacosa-11,13,15$^{27}$,16$^{26}$,17,19,21$^{25}$,22,24-nonaene, 46a, of example 43 (250 nmoles in 1.0M carbonate, 150 mM sodium chloride buffer, pH 9.3 in an acid washed, conical, glass reaction vial.

The solution is stirred briefly to mix the reactants and then left in the dark at room temperature. After 16 hours, the ING-1/chelate conjugate is separated from unconjugated chelate by applying the reaction mixture to a PD-10 chromatography column which is pre-washed and equilibrated with 50 mM sodium acetate buffer containing 150 mM sodium chloride at pH 5.6. The pure ING-1/disodium 3,9-bis(carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13, 15$^{27}$,16$^{26}$, 17,19,21$^{25}$,22,24-nonaene conjugate is eluted off the column with 2.5 mL of that same buffer, and concentrated on a Centricon-10 concentration device.

EXAMPLE 49

Radiolabeling of ING-1/disodium 3,9-bis (carboxymethyl)-18-(4-methoxyphenyl)-6-[3-(4-isothiocyanatophenylmethyl)-oxypropyl]-3,6,9,25, 26,27-hexaazatetracyclo-[19.3.1.1$^{11,15}$.1$^{16,20}$]-heptacosa-11,13,15$^{27}$,16$^{26}$, 17,19,21$^{25}$,22,24-nonaene conjugate with $^{90}$Y A volume of radioactive Yttrium chloride ($^{90}$Y in 0.04M hydrochloric acid at a specific activity of >500 Ci/g; Amersham-Mediphysics) is neutralized using two volumes of 0.5M sodium acetate pH 6.0. The neutralized $^{90}$Y (1.0 mCi) is added to 1.0 mL of ING-1/disodium 3,9-bis (carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13, 15$^{27}$,16$^{26}$,17,19,21$^{25}$,22,24-nonaene conjugate of example 47 (1 mg/mL) in 50 mM sodium acetate buffer containing 150 mM sodium chloride at pH 5.6. The labeling is allowed to proceed for one hour, and then the reaction mixture is loaded onto a PD-10 chromatography column which is pre-washed and equilibrated in a buffer containing 50 mM sodium phosphate with 150 mM sodium chloride pH 7.4 (PBS). The sample is eluted from the column with 1.5 mL of PBS. Fractions of radiolabeled ING-1/disodium 3,9-bis (carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13, 15$^{27}$,16$^{26}$, 17,19,21$^{25}$,22,24-nonaene conjugate (0.5 mL) are collected, assayed for radioactivity, and pooled. The labeling efficiency is determined by removing 1.0 uL of the sample and spotting it on to a Gelman ITLC-SG strip. The strip is developed in a glass beaker containing 0.1M sodium citrate, pH 6.0, for a few minutes until the solvent front has reached three-quarters of the way to the top of the paper. The strip is inserted into a System 200 Imaging Scanner (Bioscan) which has been optimized for $^{90}$Y and is controlled by a Compaq 386/20e computer. In this system, free $^{90}$Y migrates at the solvent front while the ING-1/disodium 3,9-bis (carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13, 15$^{27}$,16$^{26}$,17,19,21$^{25}$,22,24-nonaene conjugate containing $^{90}$Y remains at the origin. Using this system, more than 98% of the total $^{90}$Y radioactivity is found associated with ING-1/disodium 3,9-bis(carboxymethyl)-18-(4-methoxyphenyl)-6-[3-(4-isothiocyanatophenylmethyl)-oxypropyl]-3,6,9,25,26,27-hexaazatetracyclo-[19.3.1.1$^{11,15}$.1$^{16,20}$]-heptacosa-11,13,15$^{27}$,16$^{26}$, 17,19,21$^{25}$, 22,24-nonaene conjugate at the origin.

EXAMPLE 50

Antibody protein concentration

The concentrations of ING-1 for use in the conjugate reactions are determined by the BioRad protein assay (BioRad Catalog # 500-0001) using bovine immunoglobulin as the protein standard.

EXAMPLE 51

Immunoreactivity assay by Flow Cytometry

Conjugates of antibody and chelates such as those of ING-1 in examples 46, 47, 48 and 49 are examined for their ability to bind to antigens on the surface of a human tumor cell line to which the antibody had been raised. The immunoreactivity of the conjugates is compared by flow cytometry with a standard preparation of the antibody before being subjected to modification. Target HT-29 cells (a human adenocarcinoma cell line obtained from the American Type Tissue Collection: ATTC) are grown to confluency in tissue culture flasks using McCoy's media supplemented with 10% fetal calf serum. The cells are harvested by scraping the flask walls with a cell scraper. Cells from many separate flasks are pooled, centrifuged to a pellet, resuspended at $5 \times 10^5$/mL in a solution of ice-cold 50mM sodium phosphate with 150 mM sodium chloride buffer, pH 7.4, (PBS) supplemented with 0.1% bovine serum albumin (Sigma) and 0.02% sodium azide (Flow buffer). The cells are washed in this same buffer and then counted. An antibody standard curve is constructed by diluting a stock solution of ING-1 with an irrelevant (non-binding), isotype-matched control antibody, [human $IgG_1$], to give a number of samples ranging in ING-1 content from 10% to 100%. The standard curve is made in flow buffer so that each sample contains 1.0 mg/mL of protein. Samples from the standard curve and ING-1-chelate conjugate unknowns are then incubated with $5 \times 10^5$ HT29 cells at 4° C. for 1 hour.

After extensive washing to remove unbound antibody, the cells are resuspended in 100 uL flow buffer and incubated at 4° C. for 1 hour with goat-anti-human antibody labelled with fluorescene isothiocyanate. After further washing in flow buffer, the samples are analyzed by flow cytometry on a Coulter EPICS 753 flow cytometer. Fluorescein isothiocyanate (FITC) and propidium iodide (PI) are excited using the 488 nm emission line of an argon laser. The output is set at 500 mw in light regulation mode. Single cells are identified by 90 degree and forward angle light scatter. Analysis windows are applied to these parameters to separate single cells from aggregates and cell debris. Fluorescence from FITC and propidium are separated with a 550nm long pass dichroic filter and collected through a 530 nm band pass filter (for FITC), and a 635 nm band pass filter (for PI). Light scatter parameters are collected as integrated pulses, and fluorescence is collected as log integrated pulses. Dead cells are excluded from the assay by placing an analysis window on cells negative for PI uptake. The mean fluorescence per sample (weighted average from 2500 cells) is calculated for each histogram. FITC calibration beads are analysed in each experiment to establish a fluorescence standard curve. The average fluorescence intensity for each sample is then expressed as the average FITC equivalents per cell. Immunoreactivity is calculated by comparing the average fluorescence intensity of the ING-1-chelate conjugate with values from the standard curve.

EXAMPLE 52

Immunoreactivity assay by ELISA

The antigen to which the antibody, ING-1, binds is prepared from LS174T or HT-29 cells (available from ATTC) by scraping confluent monolayers of cells from the walls of culture flasks with a cell scraper. The cells from many flasks are combined and a sample is taken and counted to estimate the total number of cells harvested. At all times the cells are kept on ice. Following centrifugation of the cells at 1500 rpm for 10 minutes at 4° C., the cells are washed once in 25 mL ice-cold 50mM sodium phosphate buffer, pH 7.4, supplemented with 150 mM sodium chloride (PBS), pelleted under the same conditions and transfered in 10 mL PBS to an ice-cold glass mortar. The cells are homogenized at 4° C.using a motor-driven pestle and then centrifuged at 3000×g for 5 minutes. The antigen-rich supernatant is removed from the other cell debris and subjected to further centrifugation at 100,000×g for one hour at 4° C. The pellet (antigen fraction) from this final step is suspended in 100 uL of PBS for every million cells harvested. Following an estimate of the protein concentration (BioRad BCA protein assay using bovine immunoglobulin as the protein standard), the antigen is stored at −20° C. until use.

Each well of a 96-well Costar microtiter plate is coated with antigen by adding 100 uL/well of cell lysate (10 mg/mL) prepared as above. The microtitre plates are allowed to dry overnight in a 37° C. incubator. After washing the plates five times with 0.05% Tween-20 (Sigma), they are blotted dry. The wells of each plate are blocked by adding 125 uL/well of a 1% BSA (bovine serum albumin, Sigma) solution in PBS and incubated for 1 hour at room temperature. The plates are washed five times with 0.05% Tween-20. Samples (50 uL/well in duplicate) of ING-1-chelate conjugate and standard ING-1 antibody solutions are prepared at a range of concentrations in 1% BSA in PBS. Biotinylated ING-1 (1.0 mg/mL in 0.1% BSA) is added to each well (50 uL/well) and the plates are then incubated for 2 hours at room temperature. Following five washes with 0.05% Tween-20, the plates are blotted dry and incubated at room temperature for one hour with dilute (1:2000 in 0.1% BSA) streptavidin-alkaline phosphatase (Tago). After a further five washes, color is developed in each well upon the addition of 100 uL per well of phosphatase substrate reagent (Sigma). After one hour at room temperature, the color is read using a 405 nm filter in a Titertek Multiscan microplate reader.

EXAMPLE 53

SDS PAGE gel electrophoresis

A sample of ING-1-chelate conjugate from example 47 is subjected to electrophoresis on Novex 8%-16% reduced and native polyacrylamide gels using SDS buffers to estimate the apparent molecular weight and the degree of heterogeneity of the preparation. Using standards of known molecular weight run on the same gel, a standard curve is constructed of the distance traveled versus the log of the molecular weight. From this standard curve, the relative molecular weights of the bands associated with each conjugate preparation are determined.

EXAMPLE 54

Determination of antibody aggregate formation by size-exclusion HPLC

A 30 cm×7.5 mm TSK-G3000SW size-exclusion HPLC column (Supelco), fitted with a guard column of the same material, is equilibrated with 12 column volumes of 10 mM sodium phosphate buffer, pH 6.0, supplemented with 150 mM sodium chloride, using a Waters 600E HPLC system with a flow rate of 1.0 mL per minute at 400–600 PSI. A sample (25 uL) of BioRad gel filtration protein standards is injected onto the column. The retention time of each standard is monitored by a Waters 490 UV detector set at 280 nm. Following the recovery of the final standard, the column is washed with a further 10 volumes of 10 mM sodium phosphate buffer, pH 6.0, supplemented with 150 mM sodium chloride. Samples (50 uL) of native ING-1 antibody and of ING-1-chelate from example 47 at 200 ug/mL are separately injected onto the column and their retention times recorded. From the areas of the retained peaks and the retention time, the amount of aggregated material in the ING-1-chelate conjugate sample is calculated.

EXAMPLE 55

$Eu^{+3}$ chelate of disodium 3,9-bis(carboxymethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17,19, 21$^{25}$,22,24-nonaene A 0.01N sodium acetate aqueous solution at pH-6 containing disodium 3,9-bis(carboxymethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13, 15$^{27}$,16$^{26}$,17,19, 21$^{25}$,22,24-nonaene of example 36 was treated with $EuCl_3$, and the progress of the reaction was followed by UV spectroscopy. Uptake of Eu by the chelate was complete within 5 minutes.

EXAMPLE 56

Time delayed fluorescence of the Eu+3 chelate of 3,9-bis(carboxymethyl)-18-(4-methoxyphenyl)-6-(3-hydroxypropyl)-3,6,9,25,26,27-hexaazatetracyclo-[19.3.1.1$^{11,15}$.1$^{16,20}$]-heptacosa-11,13,15$^{27}$,16$^{26}$,17, 19,21$^{25}$,22,24-nonaene A solution of the Eu chelate of example 55 at 3 umol/mL in water was irradiated at 385 nm in a Perkin Elmer LS50 Spectrofluorometer, and emission was monitored after a 400 microsecond time delay. The wavelength of maximum emission intensity was observed at 618 nm, with other less intense emission maxima at 685, 690 and 705 nm. Fluorescence emission could be detected at 618 nm at concentrations as low as 0.1 nm/mL of complex.

The invention has been described in detail with particular reference to certain preferred embodiments thereof, but it will be understood that variations and modifications can be made within the spirit and scope of the invention.

What is claimed is:
1. A compound having the structure:

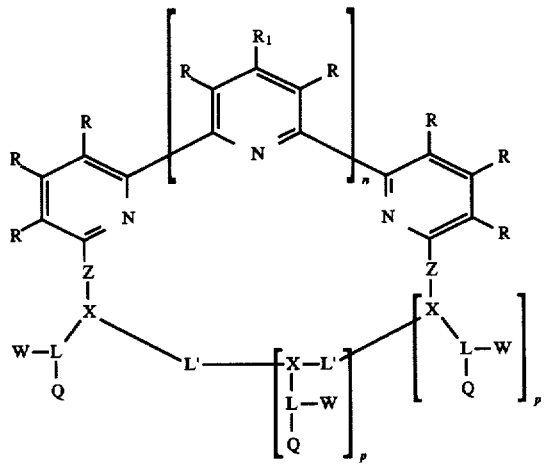

wherein
each R and $R_1$ is independently selected from hydrogen, alkyl containing from 1 to 20 carbon atoms, alkoxy, hydroxyalkyl, alkoxyalkyl, hydroxyalkyloxy, alkoxyalkyloxy, alkylthio, alkylthioalkyl, alkylthioalkyloxy, hydroxyalkylhio, hydroxyalkylthioalkyl, hydroxyalkylthioalkyloxy, N,N-dialkylaminjo, N-(hydroxyalkyl)-N-alkylamino, N,N-bis(hydroxyalkyl) amino, N,N-dialkylaminoalkyl, N-(hydroxyalkyl)-N-alkylaminoalkyl, N,N-bis (hydroxyalkyl)aminoalkyl, alkylformamido, formamidoalkyl, aryl containing from 6 to 24 carbon atoms, alkylaryl, alkoxyaryl, hydroxyalkylaryl, alkoxyalkylaryl, hydroxyalkyloxyaryl, alkoxyalkyloxyaryl, alkylthioaryl, hydroxyalkylthioaryl, hydroxyalkylthioalkylaryl, hydroxyalkythioalkyloxyaryl, aralkyl, aralkyloxy, alkoxyaralkyl, alkoxyaralkyloxy, aryloxy, alkylaryloxy, alkoxyaryloxy, and heterocyclyl containing one or more rings comprised of 5 or 6 ring carbons and ring heteroatoms selected from among O, N, S and P;

each Q is independently selected from hydrogen, alkyl, hydroxyl, carboxyl, carboxyalkyl, hydroxyalkyl, alkythioalkyl, sulfhydryl, thioalkyl, alkoxy, alkylthio, alkylamino, aminoalkyl, aminoalkylaminoalkyl, hydroxyalkylaminoalkyl, hydroxylaminoalkyl, hydroxamido, aryl, including substituted aryl, aryloxy, heterocyclyl, carbonyliminodiacetic acid, methyleneiminodiacetic acid, methylenethioethyleneiminodiacetic acid, carboxyalkylthioalky, a residue of ethylenediaminetetraacetic acid (EDTA), a residue of diethylenetriaminepentaacetic acid (DTPA), hydrazinylidenediacetic acid, and a salt of any of the foregoing acids;

each Z is independently selected from a heteroatom with a valence of two, a heteroatom with a valence of three, an alkylene group, an alkylene group bonded to a heteroatom having a valence of two, and an alkylene group bonded to a heteroatom having a valence of three;

each X is independently selected from nitrogen and a residue of an alkylene group;

each W is independently selected from hydrogen and a substituent that comprises a protein reactive group;

each L' is independently selected from a chemical bond and an intra-ring linking group;

each L is independently selected from a residue of an alkylene group and an extra-ring linking group;

n is 1, 2, 3 or 4; and each p is independently 0, 1, 2, 3 or 4;

provided that only one W is a protein reactive group; the L bonded to the W that is a protein reactive group contains 1, 2 or 3 carbon atoms and connects X to a heteroatom capable of participating in the chelation of a metal ion; and when X is a nitrogen and a heteroatom of Z is bonded to X, the heteroatom of Z is also nitrogen.

2. The compound of claim 1 wherein n is 1.

3. The compound of claim 1 wherein the protein reactive group is selected from the group consisting of amino; aminoalkyl; aminoaryl; alkylamino; arylamino; hydrazino; alkylhydrazino; arylhydrazino; carbazido; semicarbazido; thiocarbazido; hydrazidoalkyloxy; azidocarbonylalkyloxy; aryloxycarbonyloxyalkyloxy; triazines; aryloxycarbonyl (polyoxyalkyl)oxy; thiosemicarbazido; sulfhydryl; sulfhydrylalkyl; sulfhydrylaryl; hydroxy; carboxy; carboxyalkyl; carboxyaryl; active halogen containing groups; 2-leaving group-substituted ethylsulfonyl and ethylcarbonyl; vinylsulfonyl; vinyl sulfonylalkyloxy; vinyl sulfonylalkylpoly (oxyalkyl)oxy; vinylcarbonyl; oxiranyl; isocyanato; isothiocyanato; aldehydo; aziridinyl; succinimidoxycarbonyl; activated acyl groups; anhydride groups; thioester groups; active carbonates; sulfonic acid esters; phosphoramidates; cyanuric monochlorides and dichlorides.

4. The compound of claim 1 wherein the protein reactive group is selected from the group consisting of chloromethylphenyl, chloromethylcarbonyl, iodomethylcarbonyl, 2-chloroethylsulfonyl, 2-chloroethylcarbonyl, carboxylic acid halide groups, alkylhydrazino, arylhydrazino, semicarbazido, thiocarbazido, thiosemicarbazido, isocyanato and isothiocyanato, vinyl sulfonylalkyloxy, vinyl sulfonylalkyl (polyoxyalkyl)oxy, amidatoalkyloxy, hydrazidoalkyloxy, azidocarbonylalkyloxy, aryloxycarbonyloxyalkyloxy, aryloxycarbonyl(polyoxyalkyl)oxy, 4,6-dichloro-2-triazinyloxy, dichlorotriazinyl-(polyoxyalkyl)oxy, 4-alkoxy-6-chloro-2-triazinyloxy, 4-alkoxy-6-chloro-2-triazinyl (polyoxyalkyl)oxy, formylalkyl, aminoalkyl, thioalkyimidoaminoalkyloxy, active esters, active anhydrides, nitrophenylcarbonates, arylcarbonatoaryl, alkylcarbonatoaryl, arylcarbonatoalkyl, alkylcarbonatoalkyl, mixed anhydrides, thioalkylcarbonylaminoalkyloxy, succinimidoxycarbonyl, maleimidoalkylcarbonylaminoalkyloxy, azido, 4,6-dichloro-2-triazinylamino, 4,6-dichloro-2-triazinyloxyalkyl, 4,6-dichloro-2-triazinyloxyaryl, 4,6-dichlorotriazinyl-2-oxy (polyalkyloxy), iodoalkylcarbonylamino, alkylamino, arylamino, amidatoalkylamino, and amidatoarylalkylamino.

5. The compound of claim 1 wherein the protein reactive group is selected from the group consisting of sulfhydryl, amino, arylcarbonatoalkyl, active esters, isothiocyanato and thiosemicarbazido.

6. The compound of claim 1 wherein L is an extra-ring trivalent linking group.

7. The compound of claim 1 wherein L' is an extra-ring divalent linking group.

8. A metal chelate comprising the compound of claim 1 and one or more metal ions.

9. The chelate of claim 8 wherein the metal ion is a radionuclide.

10. The chelate of claim 8 wherein the metal ion is a paramagnetic metal ion.

11. The chelate of claim 9 wherein the radionuclide ion is selected from the group consisting of Sc, Fe, Pb, Ga, Y, Bi, Lu, Mn, Cu, Cr, Zn, Ge, Mo, Tc, Ru, In, Sn, Sm, Sr, Eu, Dy, Sb, W, Re, Po, Ta and Tl ions.

12. The chelate claim 11 wherein the radionuclide ion is selected from the group consisting of $^{44}Sc$, $^{111}In$, $^{212}Pb$, $^{68}Ga$, 90y, $^{177}Lu$, $^{186}Re$, $^{188}Re$, $^{64}CU$, $^{67}Cu$, $^{99}mTc$, $^{87}Y$ and $^{212}Bi$ ions.

13. The chelate of claim 10 wherein the paramagnetic metal ion is an ion of a metal of atomic number 21-29, 42, 44, or 57-71.

14. The chelate of claim 13 wherein the paramagnetic metal ion is an ion of a metal of atomic number 57-71.

15. The chelate of claim 13 wherein the paramagnetic metal ion is an ion of a metal selected from the group consisting of Cr, V, Mn, Fe, Co, Ni, Cu, La, Ce, Pr, Nd, Pm, Sm, Eu, Gd, Tb, Dy, Ho, Er, Tm, Yb, and Lu.

16. The chelate of claim 15 wherein the paramagnetic metal ion is selected from the group consisting of $Cr^{+3}$, $Cr^{+2}$, $V^{30\ 2}$, $Mn^{+3}$, $Mn^{+2}$, $Fe^{+3}$, $Fe^{+2}$, $Co^{+2}$, $Gd^{+3}$, and $Dy^{+3}$.

17. The chelate of claim 8 wherein n is 1.

* * * * *